United States Patent
Bengtsson et al.

(10) Patent No.: US 11,504,368 B2
(45) Date of Patent: Nov. 22, 2022

(54) 2,6-DIAMINO-3,4-DIHYDROPYRIMIDIN-4-ONE DERIVATIVES AND USE THEREOF IN THERAPY

(71) Applicant: THOMAS HELLEDAYS STIFTELSE FÖR MEDICINSK FORSKNING, Stockholm (SE)

(72) Inventors: Christoffer Bengtsson, Bromma (SE); Sanjay Borhade, Lund (SE); Martin Haraldsson, Täby (SE); Thomas Helleday, Stocksund (SE); Martin Henriksson, Bromma (SE); Evert Homan, Sollentuna (SE); Cynthia Paulin, Bandhagen (SE); Lars Sandberg, Enskede (SE); Martin Scobie, Uppsala (SE); Pål Stenmark, Järfälla (SE); Karl Vallin, Stockholm (SE)

(73) Assignee: THOMAS HELLEDAYS STIFTELSE FÖR MEDICINSK FORSKNING, Stockholm (SE)

( * ) Notice: Subject to any disclaimer, the term of this patent is extended or adjusted under 35 U.S.C. 154(b) by 10 days.

(21) Appl. No.: 17/043,771

(22) PCT Filed: Apr. 17, 2019

(86) PCT No.: PCT/EP2019/059919
§ 371 (c)(1),
(2) Date: Sep. 30, 2020

(87) PCT Pub. No.: WO2019/201991
PCT Pub. Date: Oct. 24, 2019

(65) Prior Publication Data
US 2021/0052587 A1  Feb. 25, 2021

(30) Foreign Application Priority Data

Apr. 18, 2018 (GB) ..................................... 1806349

(51) Int. Cl.
*C07D 401/12* (2006.01)
*C07D 401/14* (2006.01)
*A61K 31/506* (2006.01)
*A61P 35/00* (2006.01)

(52) U.S. Cl.
CPC ............ *A61K 31/506* (2013.01); *A61P 35/00* (2018.01); *C07D 401/12* (2013.01); *C07D 401/14* (2013.01)

(58) Field of Classification Search
CPC ........................... C07D 401/12; C07D 401/14
See application file for complete search history.

(56) References Cited

FOREIGN PATENT DOCUMENTS

| WO | 2014150688 A1 | 9/2014 |
| WO | 2017023894 A1 | 2/2017 |
| WO | 2017106352 A1 | 6/2017 |
| WO | 2017156362 A1 | 9/2017 |

OTHER PUBLICATIONS

International Search Report and Written Opinion for corresponding International Application No. PCT/EP2019/059919 dated Jun. 4, 2019.
Christensen et al., "Mitochondrial Methylenetetrahydrofolate Dehydrogenase, Methenyltetrahydrofolate Cyclohydrolase, andFormyltetrahydrofolate Synthetases," Vitamins and Hormones, vol. 79, 2008 Elsevier Inc., ISSN 0083-6729, DOI: 10.1016/S0083-6729(08)00414-7.
Eadsforth et al.,"Acinetobacter baumannii FoID ligand complexes—potent inhibitors of folate metabolism and a re-evaluation of the structure of L V374571," the FEBS Journal, 279 (2012) 4350-4360 © 2012 The Authors Journal compilation.
Eadsforth et al.,"Characterization of 2,4-Diamino-6-oxo-1,6-dihydropyrimidin-5-yl, Ureido Based Inhibitors of Trypanosoma brucei FoID and Testing for Antiparasitic Activity," J Med Chem 2015, 58, 7938-7948, DOI: 10.1021/acs.imedchem.5b00687.
Glauser, "Targeting the one-carbon metabolism protein MTHFD2 for cancer therapy:exploiting the unique redox status of cancer cells," 2016. Poster presented at the American Association for Cancer Research Annual Meeting, Apr. 16-20, 2016, New Orleans, LA.
Gu et al., "miR-92a Inhibits Proliferation and Induces Apoptosis by Regulating Methylenetetrahydrofolate Dehydrogenase 2 (MTHFD2) Expression in Acute Myeloid Leukemia," Oncology Research, vol. 25, pp. 1069-1079; 2017, DOI: https://doi.org/10.3727/096504016X14829256525028.
Gustafsson et al.,"The folate-coupled enzymeMTHFD2 is a nuclear protein and promotes cell proliferation," Scientific Reports; 5: 15029 | DOI: 10.1038/srep15029; Oct. 13, 2015.

(Continued)

*Primary Examiner* — Brian E McDowell
(74) *Attorney, Agent, or Firm* — Renner, Otto, Boisselle & Sklar, LLP

(57) ABSTRACT

A compound of formula (I) or a pharmaceutically acceptable salt thereof. The compound is useful in therapy, e.g. for the treatment of cancers, inflammation, autoimmune diseases and graft-versus host diseases (e.g. in transplantation patients). A pharmaceutical composition comprising the compound or its salt and a method for preparing the compound.

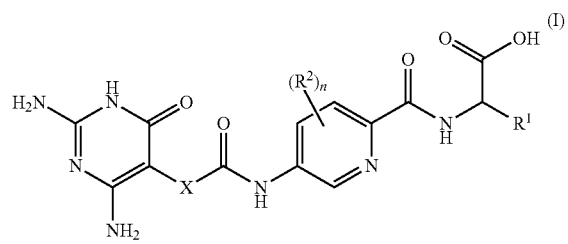

15 Claims, 2 Drawing Sheets

(56) References Cited

OTHER PUBLICATIONS

Gustafsson et al.,"Crystal Structure of the Emerging Cancer Target MTHFD2 in Complex with a Substrate-Based Inhibitor," Nov. 29, 2016, DOI: 10.1158/0008-5472.CAN-16-1476.

Jain et al., Metabolite Profiling Identifies a Key Role for Glycine in Rapid Cancer Cell Proliferation; Science 336, 1040 (2012); DOI: 10.1126/science.1218595.

Ju et al., "Modulation of Redox Homeostasis by Inhibition of MTHFD2 in Colorectal Cancer: Mechanisms and Therapeutic Implications," JNCI J Natl Cancer Inst (2019) 111(6): djy160; doi: 10.1093/jnci/djy160.

Lehtinen et al., "High-throughput RNAi screening for novel modulators of vimentin expression identifies MTHFD2 as a regulator of breast cancer cell migration and invasion," Oncotarget; Jan. 2013, vol. 4, No. 1; 48-63.

Li et al., "Drugs for Autoimmune Inflammatory Diseases: From Small MoleculeCompounds to Anti-TNF Biologies," Frontiers in Pharmacology; Jul. 12, 2017, vol. 8; Article 460; DOI: 10.3389/fphar.2017.00460.

Liu et al.,"Increased MTHFD2 expression is associated with poor prognosis in breast cancer," May 29, 2014,Tumor Biol.,DOI 10.1007/s13277-014-2111-x.

Liu et al., "Methylenetetrahydrofolate dehydrogenase 2 overexpression is associated with tumor aggressiveness and poor prognosis in hepatocellular carcinoma," Elsevier, Digestive and Liver Disease 48 (2016) 953-960.

Nilsson et al., "Metabolic enzyme expression highlights a key role for MTHFD2 and the mitochondrial folate pathway in cancer," Nature Communications, Jan. 23, 2014. 5:3128 | DOI: 10.1038/ncomms4128 |www.nature.com/naturecommunications.

Pikman et al., "Targeting MTH FD2 in acute myeloid leukemia," JEM, Jun. 20, 2016, vol. 213 No. 7 1285-1306 www.jem.org/cgi/doi/10.1084/jem.20151574.

Tonkinson et al., "The Anti proliferative and Cell Cycle Effects of 5,6, 7,8-Tetrahydro-N5,N 10-Carbonylfolic Acid, an Inhibitor of Methylenetetrahydrofolate Dehydrogenase, Are Potentiated by Hypoxanthine-," The Journal of Pharmacology and Experimental Therapeutics, vol. 287, No. 1, 315-321, May 14, 1998.

2,6-DIAMINO-3,4-DIHYDROPYRIMIDIN-4-ONE DERIVATIVES AND USE THEREOF IN THERAPY

This application is a national phase of International Application No. PCT/EP2019/059919 filed Apr. 17, 2019 and published in the English language, which claims priority to British Application No. GB 1806349.5 filed Apr. 18, 2018, both of which are hereby incorporated herein by reference.

FIELD OF THE INVENTION

The present invention relates to novel compounds and pharmaceutically acceptable salts and/or prodrugs thereof. The invention also relates to pharmaceutical formulations comprising these compounds, and to the use of such compounds and formulations in the treatment of diseases and disorders where modulation of methylenetetrahydrofolate dehydrogenase/cyclohydrolase 2 (MTHFD2) activity exerts a therapeutic effect. In particular, the present invention relates to the treatment of cell proliferation disorders, such as cancer, inflammation and autoimmune disorders.

BACKGROUND OF THE INVENTION

The listing or discussion of an apparently prior-published document in this specification should not necessarily be taken as an acknowledgement that the document is part of the state of the art or is common general knowledge.

Cancer is a group of diseases involving abnormal cell growth with the potential to invade or spread to other parts of the body. Such diseases share several characteristics with autoimmune and inflammatory disorders, which are disorders in which the cell proliferation machinery in cells causes the immune system to start reacting against its own tissues.

Cancer and other proliferative diseases have an increased demand for energy and building blocks to sustain rapid proliferation. The one-carbon (1-C) folate pathway supports this demand by generating 1-C units from serine, which are used for de novo purine synthesis, thymidine and glutathione production, and epigenetic modifications of DNA. Folic acid derivatives act as carriers for transfer of the 1-C Units between the enzymes involved in the metabolic transformations. One such enzyme is MTHFD2, a bifunctional enzyme localized to the mitochondria, which catalyzes two reactions in the mitochondrial 1-C pathway. The dehydrogenase step converts the substrate methylenetetrahydrofolate to methenyltetrahydrofolate, upon generation of NAD(P)H from NAD(P)+. The subsequent cyclohydrolase step generates N10-formyl-tetrahydrofolate from methenyltetrahydrofolate by a hydrolytic ring cleavage reaction (see Christensen and Mackenzie (2008) *Vitam. Horm.* 79, 393-410). MTHFD2 is highly upregulated across many cancers relative to normal tissues (see Jain et al. (2012) *Science* 336, 1040-1044), and genetic silencing of MTHFD2 slows proliferation across a number of cancer cell lines independent of tissue of origin (see Nilsson et al. (2014) *Nat. Commun.* 5, 3128). Lehtinen et al. have shown that MTHFD2 is overexpressed in breast cancer, associates with poor clinical characteristics and promotes cellular features connected with metastatic disease, thus implicating MTHFD2 as a potential target to block breast cancer cell migration and invasion (Lehtinen et al. (2013) *Oncotarget* 4, 48-63). Liu et al. reported enhanced expression of MTHFD2 in breast cancer tissue from patients, and MTHFD2 expression correlated with tumor size, histological grade, lymph node metastasis, and distant metastases. Furthermore, patients with MTHFD2-expressing tumors had a significantly poorer prognosis than those with absence of or low MTHFD2 expression (Liu et al. (2014) *Tumor Biol.* 35, 8685-8690).

Gustafsson Sheppard et al. demonstrated that MTHFD2 also is present in the nucleus of cancer cells and localizes to DNA synthesis sites, suggesting a possible role in DNA replication (Gustafsson Sheppard et al. (2015) *Sci. Rep.* 5, 15029). In hepatocellular carcinoma, MTHFD2 overexpression was associated with tumor aggressiveness, poor prognosis and cellular features connected to metastatic disease (Liu et al. (2016) *Dig. Liver Dis.* 48, 953-960). Koufaris et al. reported that suppression of MTHFD2 in MCF-7 breast cancer cells increased glycolysis, dependency on exogenous glycine, and sensitivity to folate depletion (Koufaris et al. (2016) *J. Proteome Res.* 15, 2618-2625).

Inhibition of MCF-7 breast cancer cell proliferation by MTHFD2 silencing with shRNA was also confirmed by Glasauer et al., while normal control cells (HACAT) were much less affected, implying a potentially large therapeutic window (Glasauer et al. (2016) AACR Poster 3790). Similarly, Pikman et al. found that knockdown of MTHFD2 in AML cells with shRNA decreased growth, induced differentiation, and impaired colony formation in primary AML blasts. In human xenograft and MLL-AF9 mouse leukemia models, MTHFD2 suppression with shRNA decreased leukemia burden and prolonged survival (Pikman et al. (2016) *J. Exp. Med.* 213, 1285-1306).

The suggested utility of MTHFD2 inhibitors for the treatment of AML was further supported by data from Gu et al. who reported that microRNA-92a may act as a tumor suppressor in AML cell lines by directly downregulating MTHFD2 expression (Gu et al. (2017) *Oncol. Res.* 25, 1069-1079). The crystal structure of human MTHFD2 in complex with a small-molecule inhibitor was published by Gustafsson et al., indicating that MTHFD2 is a drugable target (Gustafsson et al. (2017) *Cancer Res.* 77, 937-948).

Current treatments for cancer are not effective for all patients with a diagnosed disease. This also includes a large proportion of patients that experience adverse effects from treatments with current standard of care therapy or where resistance to therapy exist already at start of treatment or is developed over time.

Indeed, although the finding of oncogenes, improved diagnosis and development of new anticancer treatments have prolonged the survival of cancer patients, there is still a high medical need to find more effective and less toxic treatments for e.g. leukemia, brain, breast, colon, kidney, liver, lung, ovarian, pancreatic, prostate and skin cancer.

There is therefore a clear need for alternative treatments for cancers which may overcome present limitations.

Similarly, the treatment of autoimmune conditions, such as rheumatoid arthritis (RA), is not effective for all patients with diagnosed disease. This includes a large proportion of patients that experience adverse side-effects from treatments with biological agents, as represented by the therapy with TNF-α inhibitors, or from treatment with methotrexate and COX-2 inhibitors (Li et al. (2017) *Front. Pharmacol.* 8, 460). The cause and pathology of autoimmune and (hyper) inflammatory conditions, including multiple sclerosis (MS), inflammatory bowel disease (IBD) and the majority of less prevalent autoimmune conditions, are far from understood and many patients suffer from a disease that current treatments do not have the capacity to treat or ameliorate.

In autoimmune conditions and after organ transplantation, it is vital to eliminate the activated auto-reactive lymphocytes while preferably preserving their normal counterparts. Inhibiting MTHFD2 activity will kill the activated lymphocytes and thus reduce destructive inflammation. It should therefore be a promising novel therapy for autoimmunity and organ rejection, either as monotherapy or in combination with other drugs (e.g. cortisone) that are currently on the market.

Previous findings suggest that targeting of MTHFD2 by small molecule inhibitors could be a highly effective and safe therapeutic strategy to reduce cancer cell growth and survival. Accordingly, there have been ongoing efforts to find MTHFD2 inhibitors useful as therapeutic agents.

WO 2017/156362 describes therapeutic and diagnostic methods related to the targeting of the one-carbon metabolic pathway in T cells. The use of small-molecule MTHFD2 inhibitors is claimed but no examples are provided.

WO 2017/106352 describes inhibitors of MTHFD2 based on a caffeine-derived core and uses thereof.

International patent application WO 2017/023894 describes indole derivatives as MTHFD2 inhibitors and uses thereof.

Gustafsson et al. (Cancer Res. (2017) 77, 937-948) describe the MTHFD1 inhibitor LY345899 as an MTHFD2 inhibitor.

International patent application WO 2014/150688 describes methods of treatment, diagnosis, and determining prognosis of subjects with cancer, generally comprising determining levels of glycine metabolism or a mitochondrial 1-carbon (1-C) pathway enzyme, e.g. SHMT2, MTHFD1L, or MTHFD2, and optionally administering an antifolate or an agent that inhibits a mitochondrial 1-carbon (1-C) pathway enzyme, e.g. SHMT2 or MTHFD2.

Fu et al. (Nat. Commun. (2017) 8, 1529) describe carolacton as a nanomolar inhibitor of human MTHFD2.

Ju et al. (J. Nat. Cancer Inst (2019) 111, 1-13) describe how the mixed MTHFD1/MTHFD2 inhibitor LY345899 statistically significantly suppresses tumor growth and decreases tumor weight in colorectal cancer patient-derived xenograft mouse models.

SUMMARY OF THE INVENTION

The present inventors have unexpectedly found that certain novel compounds having a 2,6-diamino-3,4-dihydropyrimidin-4-one moiety linked to a substituted pyridine ring via a urea or acetamide linker are effective inhibitors of MTHFD2. Such compounds provide new treatments for diseases and disorders such as cancers, inflammation, autoimmune diseases and graft-versus host diseases (e.g. in transplantation patients), based on immunomodulatory effects that can be achieved by inhibition of the MTHFD2 enzyme.

Therefore, in a first aspect of the invention, there is provided a compound of formula I

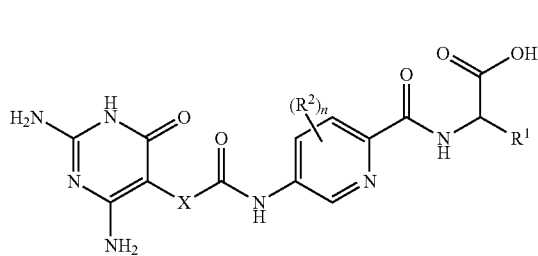

I or a pharmaceutically-acceptable salt thereof, wherein:
$R^1$ represents
(i) $C_{1-6}$ alkyl, $C_{2-6}$ alkenyl or $C_{2-6}$ alkynyl each optionally substituted by one or more groups independently selected from oxy and $A^1$, (ii) aryl optionally substituted by one or more groups independently selected from oxy and $A^2$,
(iii) heteroaryl optionally substituted by one or more groups independently selected from oxy and $A^3$,
(iv) heterocyclyl optionally substituted by one or more groups independently selected from oxy and $A^4$, or
(v) —(CH$_2$)$_2$C(O)-G;
each $R^2$ independently represents
(i) halo, —NO$_2$, —CN, —R$^{1a}$, —OR$^{1b}$, —S(O)$_p$R$^{1c}$, —S(O)$_q$(R$^{1d}$)(R$^{1e}$), —N(R$^{1f}$)S(O)$_r$R$^{1g}$, —N(R$^{1h}$)(R$^{1i}$), —C(O)OR$^{1j}$, or —C(O)N(R$^{1k}$)(R$^{1l}$),
(ii) aryl optionally substituted by one or more groups independently selected from oxy and $A^5$,
(iii) heteroaryl optionally substituted by one or more groups independently selected from oxy and $A^6$, or
(iv) heterocyclyl optionally substituted by one or more groups independently selected from oxy and $A^7$;
n represents an integer of from 0 to 3;
X represents —N(R$^3$)— or —C(R$^4$)$_2$—;
$R^3$ represents H or $C_{1-3}$ alkyl optionally substituted by one or more fluoro;
each $R^4$ independently represents H, fluoro or $C_{1-3}$ alkyl optionally substituted by one or more fluoro;
G represents —OH, or a mono- or poly-glutamic acid group;
each of $A^1$ to $A^7$ independently represents
(i) halo, —NO$_2$, —CN, —R$^{2a}$, —OR$^{2b}$, —S(O)$_p$R$^{2c}$, —S(O)$_q$N(R$^{2d}$)(R$^{2e}$), —N(R$^{2f}$)S(O)$_r$R$^{2g}$, —N(R$^{2h}$)(R$^{2i}$), —C(O)OR$^{2j}$, or —C(O)N(R$^{2k}$)(R$^{2l}$),
(ii) aryl optionally substituted by one or more groups independently selected from oxy and $B^1$,
(iii) heteroaryl optionally substituted by one or more groups independently selected from oxy and $B^2$, or
(iv) heterocyclyl optionally substituted by one or more groups independently selected from oxy and $B^3$;
each $R^{1a}$ and $R^{2a}$ independently represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $D^1$;
(ii) aryl optionally substituted by one or more groups independently selected from oxy and $D^2$,
(iii) heteroaryl optionally substituted by one or more groups independently selected from oxy and $D^3$, or
(iv) heterocyclyl optionally substituted by one or more groups independently selected from oxy and $D^4$;
each $R^{1b}$ to $R^{1l}$ and $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $D^1$;
(ii) aryl optionally substituted by one or more groups independently selected from oxy and $D^2$,
(iii) heteroaryl optionally substituted by one or more groups independently selected from oxy and $D^3$, or
(iv) heterocyclyl optionally substituted by one or more groups independently selected from oxy and $D^4$;
each of $B^1$ to $B^3$ independently represents
(i) halo, —NO$_2$, —CN, —R$^{3a}$, —OR$^{3b}$, —S(O)$_p$R$^{3c}$, —S(O)$_q$N(R$^{3d}$)(R$^{3e}$), —N(R$^{3f}$)S(O)$_r$R$^{3g}$, —N(R$^{3h}$)(R$^{3i}$), —C(O)OR$^{3j}$, or —C(O)N(R$^{3k}$)(R$^{3l}$),
(ii) aryl optionally substituted by one or more groups independently selected from oxy and $E^1$,
(iii) heteroaryl optionally substituted by one or more groups independently selected from oxy and $E^2$, or
(iv) heterocyclyl optionally substituted by one or more groups independently selected from oxy and $E^3$;

each $D^1$ independently represents
  (i) halo, —$NO_2$, —CN, —$OR^{4b}$, —$S(O)_pR^{4c}$, —$S(O)_qN(R^{4d})(R^{4e})$, —$N(R^{4f})S(O)_rR^{4g}$, —$N(R^{4h})(R^{4i})$, —$C(O)OR^{4j}$, or —$C(O)N(R^{4k})(R^{4l})$,
  (ii) aryl optionally substituted by one or more groups independently selected from oxy and $E^4$,
  (iii) heteroaryl optionally substituted by one or more groups independently selected from oxy and $E^5$, or
  (iv) heterocyclyl optionally substituted by one or more groups independently selected from oxy and $E^6$;

each $D^2$ to $D^4$ independently represents
  (i) halo, —$NO_2$, —CN, —$R^{4a}$, —$OR^{4b}$, —$S(O)_pR^{4c}$, —$S(O)_qN(R^{4d})(R^{4e})$, —$N(R^{4f})S(O)_rR^{4g}$, —$N(R^{4h})(R^{4i})$, —$C(O)OR^{4j}$, or —$C(O)N(R^{4k})(R^{4l})$,
  (ii) aryl optionally substituted by one or more groups independently selected from oxy and $E^4$,
  (iii) heteroaryl optionally substituted by one or more groups independently selected from oxy and $E^5$, or
  (iv) heterocyclyl optionally substituted by one or more groups independently selected from oxy and $E^6$;

each $R^{3a}$ and $R^{4a}$ independently represents $C_{1-3}$ alkyl optionally substituted with one or more fluoro;

each $R^{3b}$ to $R^{3l}$, and $R^{4b}$ to $R^{4l}$ independently represents H or $C_{1-3}$ alkyl optionally substituted with one or more fluoro;

each $E^1$ to $E^6$ independently represents halo, —$NO_2$, —CN, —$R^{5a}$, —$OR^{5b}$, —$S(O)_pR^{5c}$, —$S(O)_qN(R^{5d})(R^{5e})$, —$N(R^{5f})S(O)_rR^{5g}$, —$N(R^{5h})(R^{5i})$, —$C(O)OR^{5j}$, or —$C(O)N(R^{5k})(R^{5l})$;

each $R^{5a}$ independently represents $C_{1-3}$ alkyl optionally substituted with one or more fluoro;

each $R^{5b}$ to $R^{5l}$ independently represents H or $C_{1-3}$ alkyl optionally substituted with one or more fluoro; and each p, q and r independently represents 0, 1 or 2, which compounds (including pharmaceutically acceptable salts thereof) may be referred to herein as the "compounds of the invention".

In a further aspect, a process for the preparation of a compound of formula I is provided. In some embodiments, the process comprises: hydrolysis of a corresponding ester of formula II

II wherein $R^1$, $R^2$, X and n are as defined herein and $Z^1$ represents
  (a) $C_{1-6}$ alkyl optionally substituted with one or more phenyl, or
  (b) phenyl,
under conditions known to those skilled in the art, such as in the presence of aqueous hydroxide ions.

In some embodiments, for compounds comprising one or more additional carboxylic acid moieties, the process comprises: hydrolysis of a compound of formula I', or a compound of formula II' wherein the one or more additional carboxylic acid moieties present in a corresponding compound of formula I or II, as defined herein, are instead present as group(s) of formula —$C(O)OZ^2$, wherein each $Z^2$ independently represents (a) $C_{1-6}$ alkyl optionally substituted with one or more phenyl, or
  (b) phenyl,
under conditions known to those skilled in the art, such as in the presence of aqueous hydroxide ions.

In some embodiments, for compounds wherein X represents —$N(R^4)$—, the process comprises: reaction of a compound of formula IV

IV or a suitably protected derivative thereof, wherein $R^1$, $R^2$ and n are as defined herein, with a compound of formula V

V wherein each of $LG^1$ and $LG^2$ represents a suitable leaving group, and a compound of formula VI

VI wherein $R^3$ is as defined herein,
or a suitable salt thereof, under conditions known to those skilled in the art, such as in the presence of a suitable solvent and optionally a suitable base.

In some embodiments, the process comprises: reaction of a compound of formula VII

VII or a suitably protected derivative thereof, wherein $R^2$, X and n are as defined herein, with a compound of formula VIII

VIII wherein $R^1$ is as defined herein, under conditions known to those skilled in the art.

In some embodiments, for compounds wherein X represents —$C(R^4)_2$—, reaction of a compound of formula IX

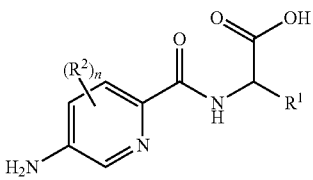

or a suitably protected derivative thereof, wherein $R^1$, $R^2$ and n are as defined herein, with a compound of formula X

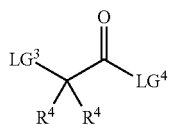

wherein each R is as defined herein and each of LG and LG independently represents a suitable leaving group, and a compound of formula XI

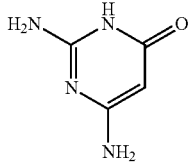

or a suitably protected derivative thereof, under conditions known to those skilled in the art.

A further aspect is a compound of formula II

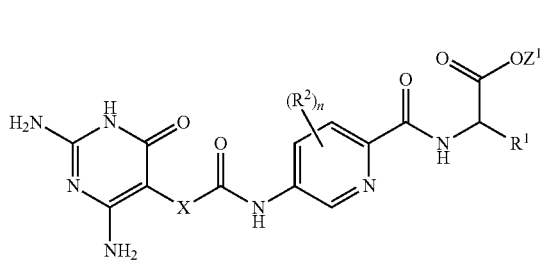

wherein $R^1$, $R^2$, X and n are as defined herein and $Z^1$ represents (a) $C_{1-6}$ alkyl optionally substituted with one or more phenyl, or (b) phenyl.

Further aspects and embodiments are as described herein below.

DETAILED DESCRIPTION OF THE INVENTION

Figure 1A:
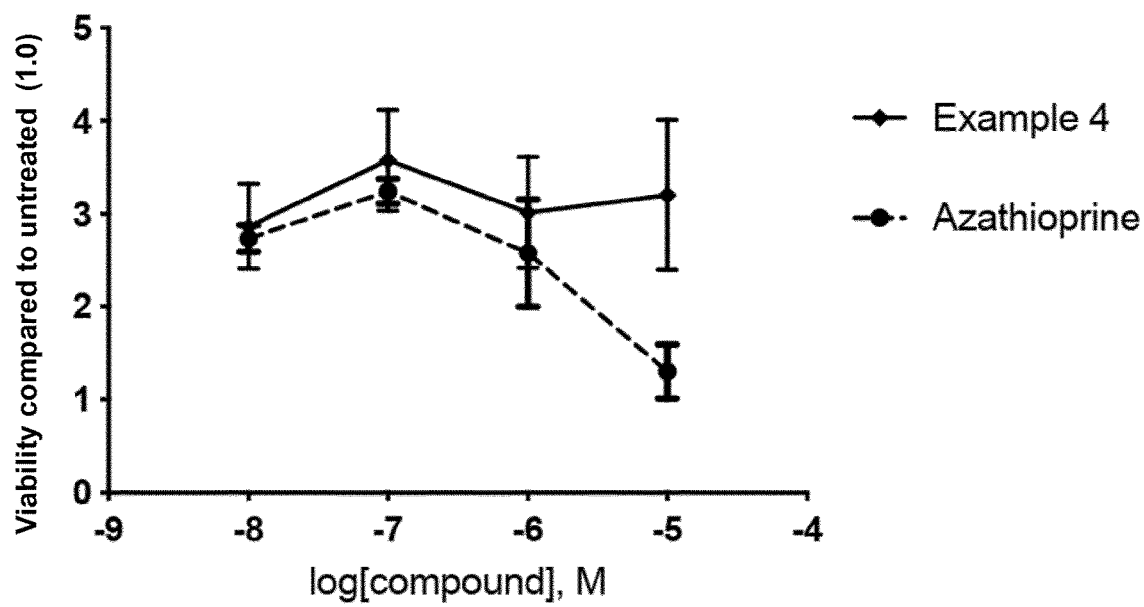
FIG. 1 is a semilogarithmic graph showing the viability, compared to untreated cells, of (A) resting T cells or (B) activated T cells upon 7 days of treatment with either Example 4 (solid lines) or azathioprine (dashed lines) at various concentrations (in M).

For the avoidance of doubt, the skilled person will understand that references herein to compounds of particular aspects of the invention (such as the first aspect of the invention, i.e. referring to compounds of formula I as defined in the first aspect of the invention) will include references to all embodiments and particular features thereof, which embodiments and particular features may be taken in combination to form further embodiments and features of the invention.

Unless indicated otherwise, all technical and scientific terms used herein will have their common meaning as understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include those formed by reaction with corresponding acids, thus protonating the compound of the invention, to form carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, so methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalene-disulphonate salts), or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed by reaction with corresponding bases, thus removing one or more proton from compounds of the invention, to form salts with alkali metals (such as Na and K salts, including mono- and di-Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

More particular pharmaceutically acceptable salts that may be mentioned include halide salts, such as hydrochloride (HCl) salts.

For the avoidance of doubt, pharmaceutically acceptable salts that may be mentioned include all such salts approved for pharmaceutical use.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline (i.e. solid) forms, such forms may include hydrates/solvates, which are included in the scope of the invention.

For the avoidance of doubt, compounds of the invention may also exist in solution (i.e. in solution in a suitable solvent). For example, compounds of the invention may exist in aqueous solution, in which case compounds of the invention may also exist in the form of hydrates thereof.

Compounds of the invention may contain double bonds and, unless otherwise indicated, may thus exist as E (entgegen) and Z (zusammen) geometric isomers about each individual double bond. Unless otherwise specified, all such isomers and mixtures thereof are included within the scope of the invention.

Compounds of the invention may also exhibit tautomerism. All tautomeric forms and mixtures thereof are included within the scope of the invention (particularly those of sufficient stability to allow for isolation thereof).

Compounds of the invention may also contain one or more asymmetric carbon atoms and may therefore exhibit optical isomerism and/or diastereoisomerism (i.e. existing in enantiomeric or diastereomeric forms). Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired enantiomer or diastereoisomer may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution; for example, with a homochiral acid followed by separation of the diastereomeric derivatives by conventional means such as chromatography), or by reaction with an appropriate chiral reagent or chiral catalyst, all of which methods and processes may be performed under conditions known to the skilled person. Unless otherwise specified, all stereoisomers and mixtures thereof are included within the scope of the invention.

For the avoidance of doubt, the skilled person will understand that where a particular group is depicted herein as being bound to a ring system via a floating bond (i.e. a bond not shown as being bound to a particular atom within the ring), the relevant group may be bound to any suitable atom within the relevant ring system (i.e. the ring within which the floating bond terminates).

Unless otherwise specified, $C_{1-z}$ alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{4-z}$ partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl. When there is a sufficient number of carbon atoms, such groups may also be multicyclic (e.g. bicyclic or tricyclic) and/or spirocyclic. For the avoidance of doubt, particular alkyl groups that may be mentioned include straight chain (i.e. not branched and/or cyclic) alkyl groups. Other alkyl groups that may be mentioned include straight chain and branched (i.e. non-cyclic) alkyl groups.

Unless otherwise specified, $C_{2-z}$ alkenyl groups (where z is the upper limit of the range) defined herein may be straight-chain or, when there is a sufficient number (i.e. a minimum of three) of carbon atoms, be branched-chain, and/or cyclic (so forming a $C_{4-z}$ cycloalkenyl group). When there is a sufficient number (i.e. a minimum of five) of carbon atoms, such groups may also be part cyclic. For example, part cyclic alkenyl groups (which may also be referred to as "part cycloalkenyl" groups) that may be mentioned include cyclopentenylmethyl and cyclohexenylmethyl. When there is a sufficient number of carbon atoms, such groups may also be multi cyclic (e.g. bicyclic or tricyclic) or spirocyclic. For the avoidance of doubt, particular alkenyl groups that may be mentioned include straight chain (i.e. not branched and/or cyclic) alkenyl groups. Other alkenyl groups that may be mentioned include straight chain and branched (i.e. non-cyclic) alkenyl groups.

Unless otherwise specified, $C_{2-z}$ alkynyl groups (where z is the upper limit of the range) defined herein may be straight-chain or, when there is a sufficient number (i.e. a minimum of four) of carbon atoms, be branched-chain. For the avoidance of doubt, particular alkynyl groups that may be mentioned include straight chain (i.e. not branched and/or cyclic) alkynyl groups. Other alkynyl groups that may be mentioned include straight chain and branched (i.e. non-cyclic) alkynyl groups.

For the avoidance of doubt, unless otherwise specified, groups referred to herein as "alkyl", "alkenyl" and/or "alkynyl" will be taken as referring to the highest degree of unsaturation in a bond present in such groups. For example, such a group having a carbon-carbon double bond and, in the same group, a carbon-carbon triple bond will be referred to as "alkynyl". Alternatively, it may be particularly specified that that such groups will comprise only the degree of unsaturation specified (i.e. in one or more bond therein, as appropriate; e.g. in one bond therein).

For the avoidance of doubt, alkyl, alkenyl and alkynyl groups as described herein may also act as linker groups (i.e. groups joining two or more parts of the compound as described), in which case such groups may also be referred to as "alkylene", "alkenylene" and/or "alkynylene" groups, respectively.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulfur (e.g. oxygen, nitrogen and sulfur, such as oxygen and nitrogen).

As used herein, the term heterocyclyl may refer to non-aromatic monocyclic and polycyclic (e.g. bicyclic) heterocyclic groups (which groups may, where containing a sufficient number of atoms, also be bridged) in which at least one (e.g. one to four) of the atoms in the ring system is other than carbon (i.e. a heteroatom), and in which the total number of atoms in the ring system is between three and twelve (e.g. between five and ten, such as between three and eight; for example, forming a 5- or 6-membered heterocyclyl group). Further, such heterocyclyl groups may be saturated, forming a heterocycloalkyl, or unsaturated containing one or more carbon-carbon or, where possible, carbon-heteroatom or heteroatom-heteroatom double and/or triple bonds, forming for example a $C_{2-z}$ (e.g. $C_{4-z}$) heterocycloalkenyl (where z is the upper limit of the range) or a $C_{7-z}$ heterocycloalkynyl group.

For the avoidance of doubt, the skilled person will understand that heterocyclyl groups that may form part of compounds of the invention are those that are chemically obtainable, as known to those skilled in the art. Various heterocyclyl groups will be well-known to those skilled in the art, such as 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, 2,3-dihydroisothiazolyl, dihydropyranyl, dihydropyridinyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridinyl (such as 1,2,3,4-tetrahydropyridinyl and 1,2,3,6-tetrahydropyridinyl), thietanyl, thiiranyl, thiolanyl, tetrahydrothiopyranyl, thiomorpholinyl, trithianyl (including 1,3,5-trithianyl), tropanyl and the like.

Substituents on heterocyclyl groups may, where appropriate, be located on any atom in the ring system including a heteroatom. Further, in the case where the substituent is another cyclic compound, then the cyclic compound may be attached through a single atom on the heterocyclyl group, forming a spirocyclic compound. The point of attachment of heterocyclyl groups may be via any suitable atom in the ring system, including (where appropriate) a further heteroatom (such as a nitrogen atom), or an atom on any fused carbocyclic ring that may be present as part of the ring system. Heterocyclyl groups may also be in the N- or S-oxidised forms, as known to those skilled in the art.

At each occurrence when mentioned herein, particular heterocyclyl groups that may be mentioned include 3- to 8-membered heterocyclyl groups (e.g. a 4- to 6-membered heterocyclyl group, such as a 5- or 6-membered heterocyclyl group).

For the avoidance of doubt, references to polycyclic (e.g. bicyclic or tricyclic) groups (for example when employed in the context of heterocyclyl or cycloalkyl groups (e.g. heterocyclyl)) will refer to ring systems wherein at least two scissions would be required to convert such rings into a non-cyclic (i.e. straight or branched) chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, to groups in which two non-adjacent atoms are linked by an alkyl (which, when linking two moieties, may be referred to as alkylene) group (optionally containing one or more heteroatoms), which later groups may be referred to as bridged, or to groups in which the second ring is attached to a single atom, which latter groups may be referred to as spiro compounds.

As may be used herein, the term aryl may refer to $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl, and the like). For the avoidance of doubt, the point of attachment of substituents on aryl groups may be via any suitable carbon atom of the ring system. For the avoidance of doubt, the skilled person will understand that aryl groups that may form part of compounds of the invention are those that are chemically obtainable, as known to those skilled in the art. Particular aryl groups that may be mentioned include phenyl.

As may be used herein, references to heteroaryl (with may also be referred to as heteroaromatic) groups may refer to 5- to 14-(e.g. 5- to 10-) membered heteroaromatic groups containing one or more heteroatoms (such as one or more heteroatoms selected from oxygen, nitrogen and/or sulfur). Such heteroaryl groups may comprise one, two, or three rings, of which at least one is aromatic. Certain heteroaryl groups that may be mentioned include those in which all rings forming such groups are aromatic.

Substituents on heteroaryl/heteroaromatic groups may, where appropriate, be located on any suitable atom in the ring system, including a heteroatom (e.g. on a suitable N atom). For the avoidance of doubt, the skilled person will understand that heteroaryl groups that may form part of compounds of the invention are those that are chemically obtainable, as known to those skilled in the art.

The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocyclyl ring.

For the avoidance of doubt, the skilled person will understand that heteroaryl groups that may form part of compounds of the invention are those that are chemically obtainable, as known to those skilled in the art. Various heteroaryl groups will be well-known to those skilled in the art, such as pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, quinolinyl, isoquinolinyl, quinazolinyl, benzofuranyl, benzothiophenyl, benzoimidazolyl, benzoxazolyl, benzothiazolyl, benzotriazolyl, pyrazolopyridinyl, pyrrolopyrazolyl and purinyl.

For the avoidance of doubt, the oxides of heteroaryl/heteroaromatic groups are also embraced within the scope of the invention (e.g. the N-oxide).

As stated above, heteroaryl includes polycyclic (e.g. bicyclic) groups in which one ring is aromatic (and the other may or may not be aromatic). Hence, other heteroaryl groups that may be mentioned include groups such as benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H, 7H-pyrrolo[1,2-b]pyrimidinyl, 1,2,3,4-tetrahydroquinolinyl, thiochromanyl, pyrazolo[3,4-b]pyridinyl, pyrrolo[3,4-c]pyrazolyl, methylenedioxyphenyl, and the like.

In some embodiments, any heteroaryl as mentioned herein is a 5- or 6-membered (e.g. 5-membered) monocyclic heteroaryl containing 1, 2, 3 or 4 heteroatoms selected from N, O and S; e.g. from N and O, or 1, 2, 3 or 4 nitrogen atoms.

Particular heteroaryl groups that may be mentioned include tetrazolyl (e.g. tetrazol-5-yl).

For the avoidance of doubt, where a ring is depicted having a circle therein, its presence shall indicate that the relevant ring is aromatic. Alternatively, aromatic groups may be depicted as cyclic groups comprising therein a suitable number of double bonds to allow for aromaticity.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. compounds of the invention in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more $R^2$ groups are present, those $R^2$ groups may be the same or different. Similarly, where two or more $R^3$ groups are present and each represent $R^{1a}$, the $R^{1a}$ groups in question may be the same or different.

Also for the avoidance of doubt, when a term such as "$A^1$ to $A^7$" is employed herein, this will be understood by the skilled person to mean $A^1$, $A^2$, $A^3$, $A^4$, $A^5$, $A^6$ and $A^7$, inclusively. Unless otherwise stated, the same reasoning will apply to other such terms used herein.

Further for the avoidance of doubt, when it is specified that a substituent is itself optionally substituted by one or more substituents (e.g. $A^1$ represents aryl optionally substituted by one or more groups independently selected from $B^1$), these substituents where possible may be positioned on the same or different atoms. Such optional substituents may be present in any suitable number thereof (e.g. the relevant group may be substituted with one or more such substituents, such as one such substituent).

For the avoidance of doubt, where groups are referred to herein as being optionally substituted it is specifically contemplated that such optional substituents may be not present (i.e. references to such optional substituents may be removed), in which case the optionally substituted group may be referred to as being unsubstituted.

A moiety —R may also be represented herein as:

For example, an ethyl group (CH$_3$CH$_2$—) may be represented as:

Likewise, for example, a methoxy group (CH$_3$O—) may be represented as:

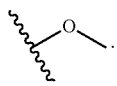

The term "oxy" as used herein refers to an oxygen atom attached to an atom (e.g. a carbon atom) via double bond, i.e. a moiety of formula

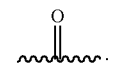

The term "carboxy" refers to a moiety of formula —C(O)OH, i.e. a carboxylic acid function, of formula:

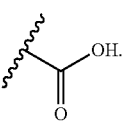 [SMILES: *C(=O)O]

The term "carboxymethyl" refers to a moiety of formula —(CH$_2$)—C(O)OH, which may also be represented as:

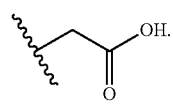

The term "2-carboxyethyl" refers to a moiety of formula —(CH$_2$)$_2$—C(O)OH, which may also be represented as:

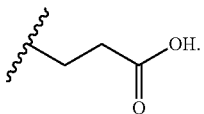

The term "3-carboxypropyl" refers to a moiety of formula —(CH$_2$)$_3$—C(O)OH, which may also be represented as:

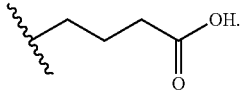 [SMILES: *CCCC(=O)O]

The term "3-((1,3-dicarboxypropyl)amino)-3-oxopropyl" refers to a moiety of formula

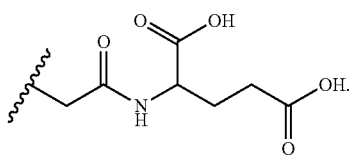 [SMILES: *CC(=O)NC(CCC(=O)O)C(=O)O]

The term "phenoxy" refers to a moiety of formula

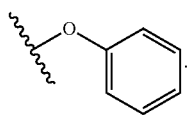

The term "phenyl" refers to a moiety of formula

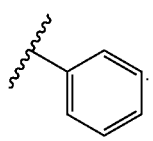 [SMILES: *c1ccccc1]

The term "benzyl" refers to a moiety of formula

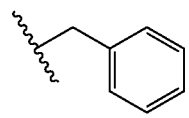 [SMILES: *Cc1ccccc1]

The term "2-phenylethyl" refers to a moiety of formula

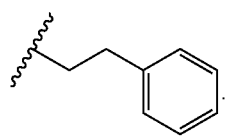

The term "phenylsulfonamido" refers to a moiety of formula

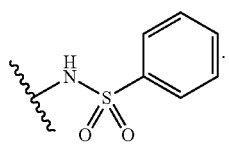

The term "3-oxo-3-(phenylsulfonamido)propyl" refers to a moiety of formula

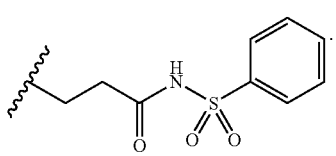 [SMILES: *CCC(=O)NS(=O)(=O)c1ccccc1]

The term "tetrazole" (and "tetrazolyl") refers to any of the possible tetrazole (and tetrazolyl) tauotmers (e.g. the 1H-tautomer).

The term "1H-tetrazol-5-yl" refers to a moiety of formula

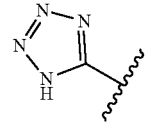

The term "2-(1H-tetrazol-5-yl)ethyl" refers to a moiety of formula

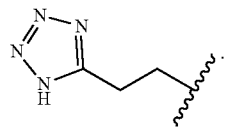

The term cyclopentylmethyl or "—CH$_2$-cyclopentyl" refers to a moiety of formula

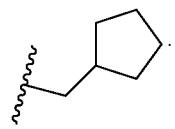

The term "sec-propyl" may be used herein synonymously with the term "isopropyl" to refer to a moiety of formula —CH(CH$_3$)$_2$, also represented as:

The term "ethenyl" refers to a moiety of formula

which may also be referred to as "vinyl".

For the avoidance of doubt, the skilled person will appreciate that compounds of the invention that are the subject of this invention include those that are obtainable, i.e. those that may be prepared in a stable form. That is, compounds of the invention include those that are sufficiently robust to survive isolation, e.g. from a reaction mixture, to a useful degree of purity.

In a compound of formula I, R$^1$ represents (i) C$_{1-6}$ alkyl, C$_{2-6}$ alkenyl or C$_{2-6}$ alkynyl each optionally substituted by one or more (e.g. 1, 2 or 3) groups independently selected from oxy and A$^1$, (ii) aryl optionally substituted by one or more (e.g. 1, 2 or 3) groups independently selected from oxy and A$^2$, (iii) heteroaryl optionally substituted by one or more (e.g. 1, 2 or 3) groups independently selected from oxy and A$^3$, (iv) heterocyclyl optionally substituted by one or more (e.g. 1, 2 or 3) groups independently selected from oxy and A$^4$, or (v) —(CH$_2$)$_2$C(O)—G.

In some embodiments, $R^1$ represents (i) $C_{1-6}$ alkyl, $C_{2-6}$ alkenyl or $C_{2-6}$ alkynyl each optionally substituted by one or more (e.g. 1, 2 or 3) groups independently selected from $A^1$, (ii) aryl optionally substituted by one or more (e.g. 1, 2 or 3) groups independently selected from $A^2$, (iii) heteroaryl optionally substituted by one or more (e.g. 1, 2 or 3) groups independently selected from $A^3$, (iv) heterocyclyl optionally substituted by one or more (e.g. 1, 2 or 3) groups independently selected from $A^4$, or (v) —(CH$_2$)$_2$C(O)—G.

In some embodiments, when $R^1$ represents a moiety selected from $C_{1-6}$ alkyl, $C_{2-6}$ alkenyl and $C_{2-6}$ alkynyl, each optionally substituted by one or more (e.g. 1, 2 or 3) groups independently selected from oxy and $A^1$, such moiety more particularly is $C_{1-6}$ alkyl optionally substituted by one or more (e.g. 1, 2 or 3) groups independently selected from oxy and $A^1$; e.g. $C_{1-6}$ alkyl optionally substituted by one or more (e.g. 1, 2 or 3) groups independently selected from $A^1$, such as $C_{1-6}$ alkyl optionally substituted by one group $A^1$.

In some embodiments, when $R^1$ represents aryl optionally substituted by one or more groups independently selected from oxy and $A^2$, such aryl more particularly is phenyl.

In some embodiments, the number of any group represented by $A^1$, $A^2$, $A^3$ or $A^4$ present in a compound of formula I is at most 2, more particularly at most 1.

In some particular embodiments, $R^1$ represents (i) $C_{1-6}$ alkyl optionally substituted by one or more (e.g. 1, 2, or 3) groups independently selected from oxy and $A^1$, (ii) aryl (e.g. phenyl) optionally substituted by one or more (e.g. 1, 2, or 3) groups independently selected from $A^2$, or (iii) —(CH$_2$)$_2$C(O)—G.

In some particular embodiments, $R^1$ represents (i) $C_{1-6}$ alkyl optionally substituted by one oxy and optionally substituted by one $A^1$, (ii) phenyl, or (iii) —(CH$_2$)$_2$C(O)—G.

In some further particular embodiments, $R^1$ represents (i) $C_{1-6}$ alkyl (e.g. methyl, ethyl, n-propyl, sec-propyl, —CH$_2$-cyclopentyl or cyclohexyl) optionally substituted by one or more (e.g. one) groups independently selected from oxy and $A^1$, (ii) phenyl optionally substituted by one or more (e.g. one) groups independently selected from $A^2$, or (iii) —(CH$_2$)$_2$C(O)—G.

In some further embodiments, $R^1$ represents (i) $C_{1-6}$ alkyl (e.g. methyl, ethyl, n-propyl, sec-propyl, —CH$_2$-cyclopentyl or cyclohexyl) optionally substituted by one or more (e.g. one) groups independently selected from oxy and $A^1$, or (ii) phenyl optionally substituted by one or more (e.g. one) groups independently selected from $A^2$.

In still some further embodiments, $R^1$ represents (i) $C_{1-6}$ alkyl (e.g. methyl, ethyl, n-propyl, sec-propyl, —CH$_2$-cyclopentyl or cyclohexyl) optionally substituted by one or more (e.g. one) groups independently selected from oxy and $A^1$, or (ii) —(CH$_2$)$_2$C(O)—G.

In still some further embodiments, $R^1$ represents $C_{1-6}$ alkyl (e.g. methyl, ethyl, n-propyl, sec-propyl, —CH$_2$-cyclopentyl or cyclohexyl) optionally substituted by one or more (e.g. one) groups independently selected from oxy and $A^1$.

In still some further embodiments, $R^1$ represents —(CH$_2$)$_2$C(O)—G.

In some embodiments, when $R^1$ represents a moiety optionally substituted by one or more groups independently selected from oxy and $A^1$, $A^2$, $A^3$ or $A^4$, respectively, as defined herein above, such moiety is not substituted by any such group (i.e. it is "unsubstituted").

In some embodiments, $R^1$ represents an unsubstituted moiety selected from $C_{1-6}$ alkyl, $C_{2-6}$ alkenyl, $C_{2-6}$ alkynyl and phenyl. In some such embodiments, $R^1$ represents unsubstituted $C_{1-6}$ alkyl or unsubstituted phenyl.

In some embodiments, when $R^1$ represents an unsubstituted alkyl group, said alkyl contains at least three carbon atoms. For example, in some embodiments, $R^1$ represents unsubstituted $C_{3-6}$ alkyl or unsubstituted phenyl, such as n-propyl, sec-propyl, —CH$_2$-cyclopentyl, cyclohexyl, or phenyl; or $R^1$ represents unsubstituted $C_{3-6}$ alkyl such as n-propyl, sec-propyl, —CH$_2$-cyclopentyl, or cyclohexyl.

In some other embodiments, $R^1$ represents a moiety selected from methyl, ethyl, n-propyl, sec-propyl, —CH$_2$-cyclopentyl, cyclohexyl, and phenyl.

In still some other embodiments $R^1$ represents a moiety selected from methyl, ethyl, n-propyl, sec-propyl, —CH$_2$-cyclopentyl, and cyclohexyl.

As described herein, G represents OH, or a mono- or poly-glutamic acid group. In particular embodiments, G represents OH or a mono-glutamic acid group.

In some further particular embodiments, G represents OH. In still further embodiments, G represents a mono- or poly-glutamic acid group, in particular a mono-glutamic acid group.

The skilled person will understand that references to a (mono-)glutamic acid group will refer in particular to a glutamic acid bound via the amino component thereof (i.e. to form an amide moiety), i.e. a group of formula

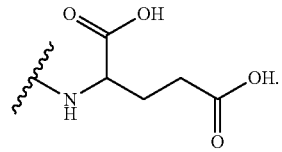 [SMILES: *NC(CCC(=O)O)C(=O)O]

Similarly, references to a poly-glutamic acid group will refer to a polymerised chain of glutamic acid groups bound via the amino group of the first glutamic acid group, forming bounds with further groups between the carboxylic acid group of the preceding glutamic acid and the amino group of the following carboxylic acid (i.e. forming an amide moiety), and terminating with a carboxylic acid.

The skilled person will understand that such poly-glutamic acid groups will comprise at least two glutamic acid groups so polymerised. In particular, such poly-glutamic acid groups may comprise up to seven glutamic acid groups so polymerised.

Thus, where there is a mono- or poly-glutamic acid group representing G, that group together with the —(CH$_2$)$_2$C(O)— group to which it is attached may result in a moiety of structural formula XII:

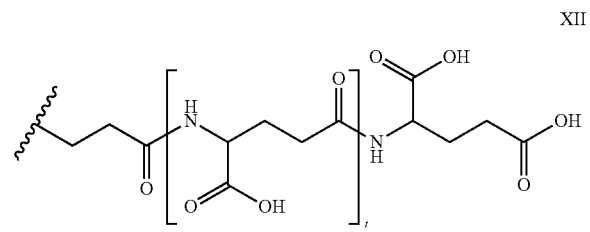

wherein t represents 0 to 7.

In some particular embodiments, when —(CH$_2$)$_2$C(O)—G (i.e. R$^1$) represents a moiety of formula XII, t represents an integer of from 0 to 3, in particular from 0 to 2, e.g. t is 0 or 1.

In some particular embodiments, t represents 0, i.e. G is a mono-glutamic acid group, and R$^1$ is a moiety of formula

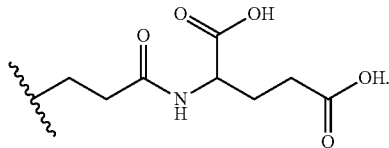 [SMILES: *CCC(=O)NC(CCC(=O)O)C(=O)O]

Thus, in some particular embodiments, R$^1$ represents a moiety selected from

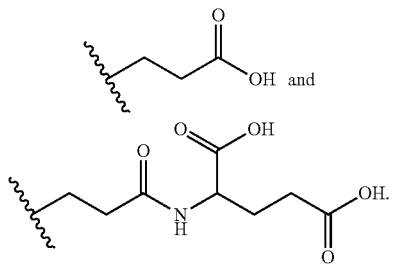

In some particular embodiments, R$^1$ represents

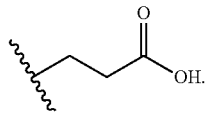 [SMILES: *CCC(=O)O]

In some further embodiments, R$^1$ represents a moiety selected from isopropyl, cyclopentylmethyl, cyclohexyl, phenyl, benzyl, 2-phenylethyl, 3-oxo-3-(phenylsulfonamido)propyl, 2-(1H-tetrazol-5-yl)ethyl, carboxymethyl, 2-carboxyethyl, 3-carboxypropyl, and 3-((1,3-dicarboxypropyl)amino)-3-oxopropyl.

In a compound of formula I each R$^2$ independently represents
(i) halo, —NO$_2$, —CN, —R$^{1a}$, —OR$^{1b}$, —S(O)$_p$R$^{1c}$, —S(O)$_q$(R$^{1d}$)(R$^{1e}$), —N(R$^{1f}$)S(O)$_r$R$^{1g}$, —N(R$^{1h}$)(R$^{1i}$), —C(O)OR$^{1j}$, or —C(O)N(R$^{1k}$)(R$^{1l}$),
(ii) aryl (e.g. phenyl) optionally substituted by one or more (e.g. 1-3) groups independently selected from oxy and A$^5$,
(iii) heteroaryl optionally substituted by one or more (e.g. 1-3) groups independently selected from oxy and A$^6$, or
(iv) heterocyclyl optionally substituted by one or more (e.g. 1-3) groups independently selected from oxy and A$^7$.

In some embodiments, each R$^2$ independently represents
(i) halo, —NO$_2$, —CN, —R$^{1a}$, —OR$^{1b}$, —S(O)$_p$R$^{1c}$, —S(O)$_q$(R$^{1d}$)(R$^{1e}$), —N(R$^{1f}$)S(O)$_r$R$^{1g}$, —N(R$^{1h}$)(R$^{1i}$), —C(O)OR$^{1j}$, or —C(O)N(R$^{1k}$)(R$^{1l}$),
(ii) aryl (e.g. phenyl) optionally substituted by one or more (e.g. 1-3) groups independently selected from oxy and A$^5$, or
(iii) heteroaryl optionally substituted by one or more (e.g. 1-3) groups independently selected from oxy and A$^6$.

In some further embodiments, each R$^2$ independently represents
(i) halo, —NO$_2$, —CN, —R$^{1a}$, —OR$^{1b}$, —S(O)$_p$R$^{1c}$, —S(O)$_q$(R$^{1d}$)(R$^{1e}$), —N(R$^{1f}$)S(O)$_r$R$^{1g}$, —N(R$^{1h}$)(R$^{1i}$), —C(O)OR$^{1j}$, or —C(O)N(R$^{1k}$)(R$^{1l}$), or
(ii) aryl (e.g. phenyl) optionally substituted by one or more (e.g. 1-3) groups independently selected from oxy and A$^5$.

In some further embodiments, each R$^2$ independently represents halo, —NO$_2$, —CN, —R$^{1a}$, —OR$^{1b}$, —S(O)$_p$R$^{1c}$, —S(O)$_q$(R$^{1d}$)(R$^{1e}$), —N(R$^{1f}$)S(O)$_r$R$^{1g}$, —N(R$^{1h}$)(R$^{1i}$), —C(O)OR$^{1j}$, or —C(O)N(R$^{1k}$)(R$^{1l}$).

In some further embodiments, each R$^2$ independently represents halo, —NO$_2$, —CN, —R$^{1a}$, or —OR$^{1b}$.

In some embodiments each R$^2$ independently represents halo (e.g. chloro or fluoro), —R$^{1a}$ or —OR$^{1b}$.

In some embodiments, each R$^2$ independently represents halo or —OR$^{1b}$.

In some embodiments, each R$^2$ independently represents halo or —R$^{1a}$.

In some particular embodiments, each R$^2$ independently represents halo, e.g. F or Cl.

In some more particular embodiments, each R$^2$ independently represents F. In some embodiments, R$^2$ represents a moiety selected from fluoro, chloro, methyl, trifluoromethyl, ethenyl, cyclopropyloxy, phenoxy, and phenyl.

The number of moieties R$^2$ present in a compound of formula I (which number is represented by n) may range from 0 to 3 (i.e. n represents 0, 1, 2 or 3). In some embodiments, n represents 0, 1 or 2. In some further embodiments, n represents 0 or 1. In some particular embodiments, n represents 1. In some further particular embodiments, n represents 1, 2 or 3. In some embodiments, n represents 1 or 2. In still some further embodiments, n represents 0. In some embodiments, when X represents —N(R$^3$)—, e.g. when X represents —NH—, n does not represent 0.

In a compound of formula I, X represents —N(R$^3$)— or —C(R$^4$)$_2$—. In some embodiments, X represents —N(R$^3$)—. In some other embodiments, X represents —C(R$^4$)$_2$—.

The moiety R$^3$ represents H or C$_{1-3}$ alkyl optionally substituted by one or more fluoro. In some embodiments, R$^3$ represents H.

Each R$^4$ independently represents H, fluoro or C$_{1-3}$ alkyl (e.g. methyl) optionally substituted by one or more fluoro. In some embodiments, each R$^4$ independently represents H or fluoro. In still further embodiments, each R$^4$ represents H.

In some embodiments, X represents —NH— or —CH$_2$—. In some particular embodiments, X represents —CH$_2$—. In some other particular embodiments, X represents —NH—.

In a compound of formula I, each of A$^1$ to A$^7$ independently represents
(i) halo, —NO$_2$, —CN, —R$^{2a}$, —OR$^{2b}$, —S(O)$_p$R$^{2c}$, —S(O)$_q$N(R$^{2d}$)(R$^{2e}$), —N(R$^{2f}$)S(O)$_r$R$^{2g}$, —N(R$^{2h}$)(R$^{2i}$), —C(O)OR$^{2j}$, or —C(O)N(R$^{1k}$)(R$^{1l}$),
(ii) aryl optionally substituted by one or more groups independently selected from oxy and B$^1$,
(iii) heteroaryl optionally substituted by one or more groups independently selected from oxy and B$^2$, or
(iv) heterocyclyl optionally substituted by one or more groups independently selected from oxy and B$^3$.

In some embodiments, each of $A^1$ to $A^7$ independently represents
- (i) halo, $-NO_2$, $-CN$, $-R^{2a}$, $-OR^{2b}$, $-S(O)_pR^{2c}$, $-S(O)_qN(R^{2d})(R^{2e})$, $-N(R^{2f})S(O)_rR^{2g}$, $-N(R^{2h})(R^{2i})$, $-C(O)OR^{2j}$, or $-C(O)N(R^{1k})(R^{1l})$,
- (ii) aryl optionally substituted by one or more groups independently selected from oxy and $B^1$, or
- (iii) heteroaryl optionally substituted by one or more groups independently selected from oxy and $B^2$.

In some embodiments, each of $A^1$ to $A^7$ independently represents
- (i) $-R^{2a}$, $-N(R^{2f})S(O)_rR^{2g}$, $-C(O)OR^{2j}$ or $-C(O)N(R^{1k})(R^{1l})$,
- (ii) phenyl optionally substituted by one or more (e.g. one) groups independently selected from oxy and $B^1$, or
- (iii) heteroaryl (e.g. tetrazolyl) optionally substituted by one or more (e.g. one) groups independently selected from oxy and $B^2$.

In some particular embodiments, each of $A^1$ to $A^7$ independently represents halo, $-NO_2$, $-CN$, $-R^{2a}$, $-OR^{2b}$, $-S(O)_pR^{2c}$, $-S(O)_qN(R^{2d})(R^{2e})$, $-N(R^{2f})S(O)_rR^{2g}$, $-N(R^{2h})(R^{2i})$, $-C(O)OR^{2j}$, or $-C(O)N(R^{1k})(R^{1l})$.

In some further particular embodiments, each of $A^1$ to $A^7$ independently represents $-R^{2a}$, $-OR^{2b}$, $-N(R^{2f})S(O)_rR^{2g}$, $-C(O)OR^{2j}$ or $-C(O)N(R^{1k})(R^{1l})$.

In some further particular embodiments, each of $A^1$ to $A^7$ independently represents $-R^{2a}$, $-OR^{2b}$, $-N(R^{2f})S(O)_rR^{2g}$, or $-C(O)OR^{2j}$.

In some further particular embodiments, each of $A^1$ to $A^7$ independently represents $-R^{2a}$, $-N(R^{2f})S(O)_rR^{2g}$, or $-C(O)OR^{2j}$.

In some further particular embodiments, each of $A^1$ to $A^7$ independently represents $-N(R^{2f})S(O)_rR^{2g}$, or $-C(O)OR^{2j}$; or each of $A^1$ to $A^7$ independently represents $-C(O)OR^{2j}$.

In still further embodiments, each of $A^1$ to $A^7$ independently represents a moiety selected from hydroxy, sulfonamido, carboxy, phenyl, and tetrazolyl (e.g. 1H-tetrazol-5-yl).

In some embodiments, $A^5$ to $A^7$ are absent and each $A^1$ to $A^4$ is as indicated herein above.

In some embodiments, $A^2$ to $A^7$ are absent and each $A^1$ is as indicated herein above.

In a compound of formula I, each $R^{1a}$ and $R^{2a}$ independently represents
- (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $D^1$,
- (ii) aryl optionally substituted by one or more (e.g. 1-3) groups independently selected from oxy and $D^2$,
- (iii) heteroaryl optionally substituted by one or more (e.g. 1-3) groups independently selected from oxy and $D^3$, or
- (iv) heterocyclyl optionally substituted by one or more (e.g. 1-3) groups independently selected from oxy and $D^4$.

In some embodiments, each $R^{1a}$ and $R^{2a}$ independently represents $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $D^1$; e.g. each $R^{1a}$ and $R^{2a}$ independently represents $C_{1-6}$ alkyl, or $C_{2-6}$ alkenyl wherein each such alkyl or alkenyl group is optionally substituted by one or more groups independently selected from oxy and $D^1$; or each $R^{1a}$ and $R^{2a}$ independently represents $C_{1-6}$ alkyl, wherein each such alkyl group is optionally substituted by one or more groups independently selected from oxy and $D^1$.

In some of the above embodiments, in any $R^{1a}$ or $R^{2a}$, any $C_{1-6}$ alkyl more particularly is selected from $C_{1-3}$ alkyl; any $C_{2-6}$ alkenyl more particularly is selected from $C_{2-3}$ alkenyl; and any $C_{2-6}$ alkynyl more particularly is selected from $C_{2-3}$ alkynyl.

In $R^{1a}$ and $R^{2a}$, any $C_{1-6}$ alkyl, $C_{2-6}$ alkenyl and $C_{2-6}$ alkynyl may optionally be substituted by one or more groups independently selected from oxy and $D^1$. In some embodiments, any such substituent groups are selected from $D^1$, e.g. any $C_{1-6}$ alkyl, $C_{2-6}$ alkenyl and $C_{2-6}$ alkynyl may optionally be substituted by 1, 2 or 3 groups independently selected from $D^1$.

In some embodiments, each $R^{1a}$ and $R^{2a}$ is independently selected from methyl and ethenyl, optionally substituted by one or more groups independently selected from $D^1$.

In some embodiments, $R^{2a}$ is absent and each $R^{1a}$ is as indicated herein above.

Particular $R^{1a}$ groups that may be mentioned include $C_{1-6}$ alkyl and $C_{2-6}$ alkenyl each optionally substituted by one or more (e.g. one to three) groups independently selected from oxy and $D^1$.

More particular $R^{1a}$ groups that may be mentioned include methyl and ethenyl each optionally substituted by one or more groups independently selected from $D^1$.

In a compound of formula I, each $R^{1b}$ to $R^{1l}$ and $R^{2b}$ to $R^{2l}$ independently represents H or
- (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $D^1$;
- (ii) aryl (e.g. phenyl) optionally substituted by one or more (e.g. 1-3) groups independently selected from oxy and $D^2$,
- (iii) heteroaryl optionally substituted by one or more (e.g. 1-3) groups independently selected from oxy and $D^3$, or
- (iv) heterocyclyl optionally substituted by one or more (e.g. 1-3) groups independently selected from oxy and $D^4$.

In some embodiments, each $R^{1b}$ to $R^{1l}$ and $R^{2b}$ to $R^{2l}$ independently represents H, or
- (i) $C_{1-6}$ alkyl, $C_{2-6}$ alkenyl or $C_{2-6}$ alkynyl, wherein each such alkyl, alkenyl or alkynyl group is optionally substituted by one or more (e.g. 1-3) groups independently selected from oxy and $D^1$; or
- (ii) phenyl optionally substituted by one or more (e.g. 1-3) groups independently selected from oxy and $D^2$.

In some embodiments, each $R^{1b}$ to $R^{1l}$ and $R^{2b}$ to $R^{2l}$ independently represents H, or (i) $C_{1-6}$ alkyl, wherein each such alkyl group is optionally substituted by one or more (e.g. 1-3) groups independently selected from oxy and $D^1$; or (ii) phenyl optionally substituted by one or more (e.g. 1-3) groups independently selected from oxy and $D^2$.

In some of the above embodiments, any $C_{1-6}$ alkyl more particularly is selected from $C_{1-3}$ alkyl; any $C_{2-6}$ alkenyl more particularly is selected from $C_{2-3}$ alkenyl; and any $C_{2-6}$ alkynyl more particularly is selected from $C_{2-3}$ alkynyl.

In $R^{1b}$ to $R^{1l}$ and $R^{2b}$ to $R^{2l}$, any $C_{1-6}$ alkyl, $C_{2-6}$ alkenyl and $C_{2-6}$ alkynyl may optionally be substituted by one or more groups independently selected from oxy and $D^1$. In some embodiments, any such substituent groups are selected from $D^1$, e.g. any $C_{1-6}$ alkyl, $C_{2-6}$ alkenyl and $C_{2-6}$ alkynyl may optionally be substituted by 1, 2 or 3 groups independently selected from $D^1$.

For example, in some particular embodiments, any $R^{1b}$ or $R^{2b}$ (in particular any $R^{1b}$) is $C_{1-6}$ alkyl or phenyl; any $R^{1f}$ or $R^{2f}$ (in particular any $R^{2f}$) is H; any $R^{1g}$ or $R^{2g}$ (in particular any $R^{2g}$) is phenyl; and any $R^{1j}$ or $R^{2j}$ (in particular any $R^{2j}$) is H.

In some embodiments, particular $R^{1b}$ groups that may be mentioned include:

(i) $C_{1-6}$ alkyl (e.g. $C_{1-3}$ alkyl) optionally substituted by one or more (e.g. one) groups independently selected from oxy and $D^1$; and (ii) aryl (e.g. phenyl) optionally substituted by one or more (e.g. one) groups independently selected from oxy and $D^2$.

More particular $R^{1b}$ groups that may be mentioned include phenyl and cyclopropyl.

In some further particular embodiments, $R^{2f}$ represents H and/or (e.g. and) $R^{2g}$ represents aryl (e.g. phenyl) optionally substituted by one or more (e.g. one) groups independently selected from oxy and $D^2$.

Likewise, some further particular $R^{2j}$ groups that may be mentioned include $C_{1-6}$ alkyl (e.g. methyl and ethyl, such as ethyl) and H. More particular $R^{2j}$ groups that may be mentioned include H.

In still some further particular embodiments, $R^{2k}$ represents H and/or (e.g. and) $R^{2l}$ represents $C_{1-6}$ alkyl optionally substituted by one or more groups independently selected from oxy and $D^1$.

In a compound of formula I, each of $B^1$ to $B^3$ independently represents (i) halo, $-NO_2$, $-CN$, $-R^{3a}$, $-OR^{3b}$, $-S(O)_pR^{3c}$, $-S(O)_qN(R^{3d})(R^{3e})$, $-N(R^{3f})S(O)_rR^{3g}$, $-N(R^{3h})(R^{3i})$, $-C(O)OR^{3j}$, or $-C(O)N(R^{3k})(R^{3l})$, (ii) aryl optionally substituted by one or more groups independently selected from oxy and $E^1$, (iii) heteroaryl optionally substituted by one or more groups independently selected from oxy and $E^2$, or (iv) heterocyclyl optionally substituted by one or more groups independently selected from oxy and $E^3$.

In some embodiments, each of $B^1$ to $B^3$ independently represents halo, $-NO_2$, $-CN$, $-R^{3a}$, $-OR^{3b}$, $-S(O)_pR^{3c}$, $-S(O)_qN(R^{3d})(R^{3e})$, $-N(R^{3f})S(O)_rR^{3g}$, $-N(R^{3h})(R^{3i})$, $-C(O)OR^{3j}$, or $-C(O)N(R^{3k})(R^{3l})$.

In some embodiments, $B^1$, $B^2$ and $B^3$ are absent.

In a compound of formula I, each $D^1$ independently represents (i) halo, $-NO_2$, $-CN$, $-R^{4a}$, $-OR^{4b}$, $-S(O)_pR^{4c}$, $-S(O)_qN(R^{4d})(R^{4e})$, $-N(R^{4f})S(O)_rR^{4g}$, $-N(R^{4h})(R^{4i})$, $-C(O)OR^{4j}$, or $-C(O)N(R^{4k})(R^{4l})$, (ii) aryl optionally substituted by one or more groups independently selected from oxy and $E^4$, (iii) heteroaryl optionally substituted by one or more groups independently selected from oxy and $E^5$, or (iv) heterocyclyl optionally substituted by one or more groups independently selected from oxy and $E^6$.

Particular $D^1$ groups that may be mentioned include $-C(O)OR^{4j}$, such as wherein $R^{4j}$ represents $C_{1-6}$ alkyl (e.g. methyl and ethyl, such as ethyl) or H (e.g. $R^{4j}$ represents H).

Further particular $D^1$ groups that may be mentioned include fluoro. Thus, in some embodiments, any $D^1$, when present, is fluoro.

In a compound of formula I, each $D^2$ to $D^4$ independently represents (i) halo, $-NO_2$, $-CN$, $-R^{4a}$, $-OR^{4b}$, $-S(O)_pR^{4c}$, $-S(O)_qN(R^{4d})(R^{4e})$, $-N(R^{4f})S(O)_rR^{4g}$, $-N(R^{4h})(R^{4i})$, $-C(O)OR^{4j}$, or $-C(O)N(R^{4k})(R^{4l})$, (ii) aryl optionally substituted by one or more groups independently selected from oxy and $E^4$, (iii) heteroaryl optionally substituted by one or more groups independently selected from oxy and $E^5$, or (iv) heterocyclyl optionally substituted by one or more groups independently selected from oxy and $E^6$.

In some embodiments, each $D^2$ to $D^4$ independently represents halo, $-NO_2$, $-CN$, $-R^{4a}$, $-OR^{4b}$, $-S(O)_pR^{4c}$, $-S(O)_qN(R^{4d})(R^{4e})$, $-N(R^{4f})S(O)_rR^{4g}$, $-N(R^{4h})(R^{4i})$, $-C(O)OR^{4j}$, or $-C(O)N(R^{4k})(R^{4l})$.

In some embodiments, $D^2$, $D^3$ and $D^4$ are absent.

In a compound of formula I, each p, q and r independently represents 0, 1 or 2. In particular embodiments, each p, q and r represents 2.

As described herein, compounds of the invention may possess one or more chiral centres and, as such, may be present as single enantiomers or diastereoisomers (as appropriate), or as mixtures thereof (e.g. racemic mixtures).

Particular compounds of the invention that may be mentioned include those in which the carbon atom carrying the essential carboxylic acid group (i.e. the carboxylic acid group depicted in formula I) is in the R configuration.

Other particular compounds of the invention that may be mentioned include those in which the carbon atom carrying the essential carboxylic acid group (i.e. the carboxylic acid group depicted in formula I) is in the S configuration.

In a particular embodiment that may be mentioned, the compound of formula I is a compound of formula Ia

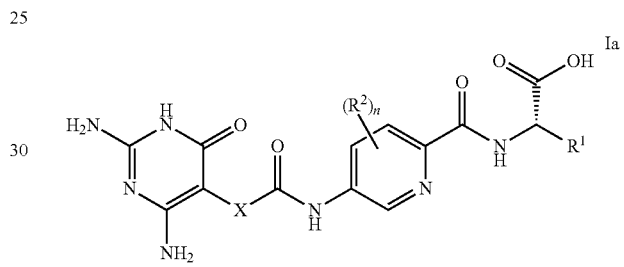

wherein $R^1$, $R^2$, X and n are as defined herein (i.e. for compounds of formula I, including all embodiments thereof).

For the avoidance of doubt, the skilled person will understand that the stereochemistry shown in formula Ia is relative. In such instances (i.e. where stereochemistry is indicated), compounds may be defined as being provided such that the required enantiomer (or, in cases where further stereocentres are present, the relevant diastereoisomer or mixture of diastereoisomers) is present in an excess when compared to the relative amounts of other possible stereoisomers, such as being present in an excess, such as an enantiomeric excess (e.e.) of at least 60% (such as at least 70%, 80%, 85%, 90% or 95%, e.g. at least 99% or at least 99.9%).

In some embodiments, when n in formula I represents 1, 2 or 3 (e.g. 1 or 2), one $R^2$ is attached in 3-position on the pyridine ring. In some particular embodiments, the compound of formula I is as represented by formula Ib

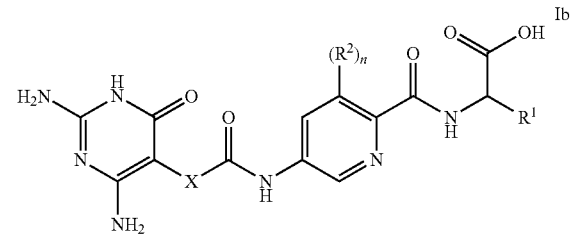

wherein $R^1$, $R^2$, and X are as defined herein and n is 0 or 1. In some of these embodiments, n is 1, i.e. the compound of formula is as represented by formula Ic

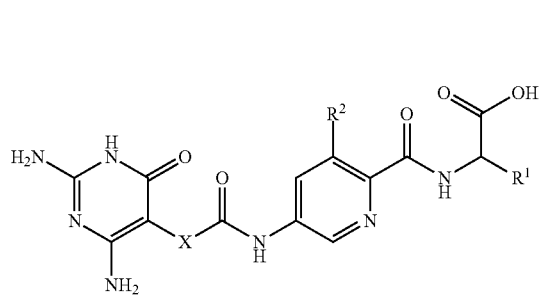

Ic wherein $R^1$, $R^2$, and X are as defined herein.

In some further embodiments, when n in formula I represents 1, 2 or 3 (e.g. 1 or 2), one $^2$ is attached in 6-position on the pyridine ring. In some particular embodiments, the compound of formula I more particularly is a compound of formula Id

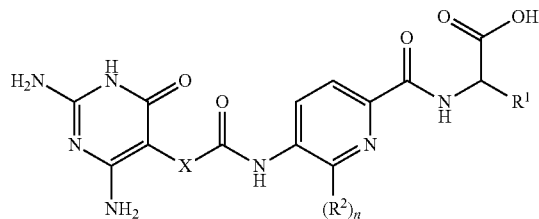

Id wherein $R^1$, R, and X are as defined herein, and n is 0 or 1. In some of these embodiments, n is 1, i.e. the compound of formula is as represented by formula Ie

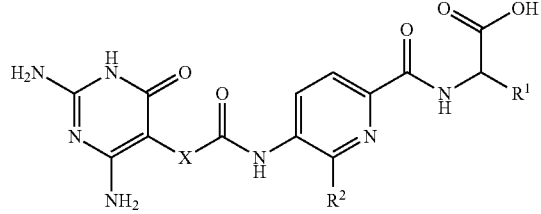

Ie wherein $R^1$, $R^2$, and X are as defined herein.

In some embodiments, when n represents 0 or 1, the compound of formula I is a compound of formula Ib or Id, in particular a compound of formula Ib.

In some further embodiments, when n represents 1, the compound of formula I is a compound of formula Ic or Ie, in particular a compound of formula Ic.

In some embodiments, a compound of formula Ib, Ic, Id, or Ie also is a compound of formula Ia. Thus, for example, in some embodiments, the compound of formula Ib also is a compound of formula Ia, i.e. a compound that may be represented by formula If

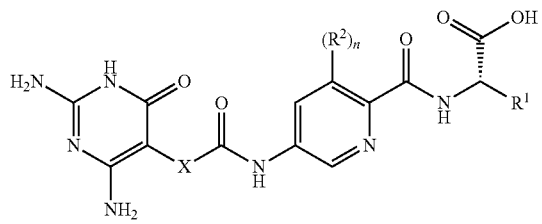

If wherein $R^1$, $R^2$, and X are as defined herein and n is 0 or 1, in particular 1.

In some further particular embodiments the compound of formula I may be represented by formula Ig

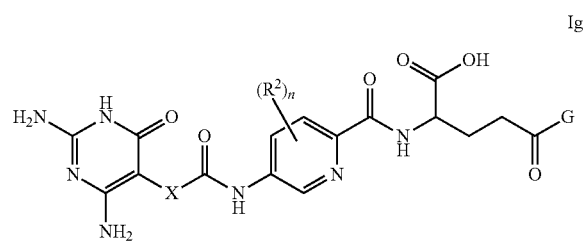

Ig wherein $R^2$, X, G and n are as defined herein.

In some particular embodiments, a compound of formula Ig also is a compound of any one of the formulas Ia, Ib, Ic, Id, Ie, or If. For example, in some embodiments, the compound more particularly may be represented by formula Ih

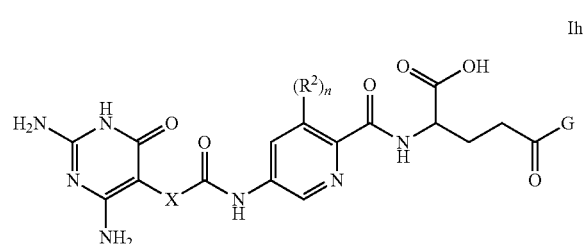

Ih wherein $R^2$, X, and G are as defined herein, and n is 0 or 1, in particular 1.

In some particular embodiments, a compound of formula Ig more particularly also is a compound of formula Ia, i.e. a compound that may be represented by formula Ii

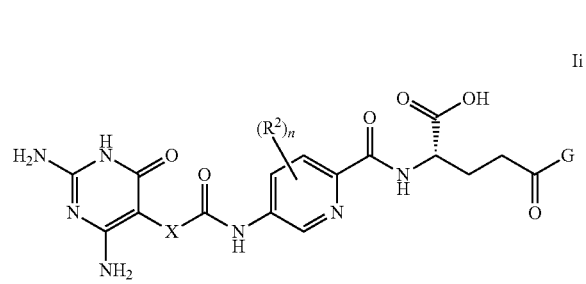

Ii wherein $R^2$, X, G and n are as defined herein.

In some further particular embodiments, a compound of formula Ii also is a compound of formula Ib, i.e. a compound that may be represented by formula Ij

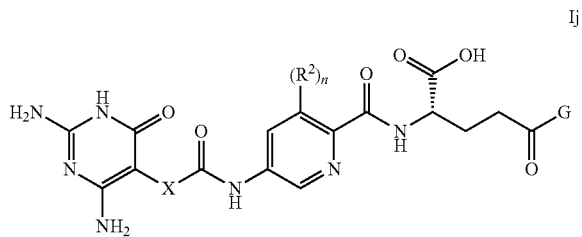

wherein $R^2$, X, and G are as defined herein, and n is 0 or 1, in particular 1.

In some of embodiments, a compound of formula Id or Ie also is a compound of formula Ig or Ii. Thus, in some embodiments, the compound is one that may be represented by formula Ik

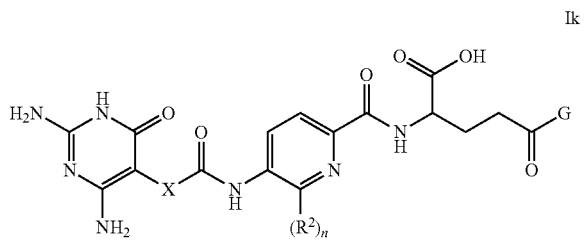

wherein $R^2$, X, and G are as defined herein, and n is 0 or 1, in particular 1; and in some embodiments, the compound is one that may be represented by formula Im

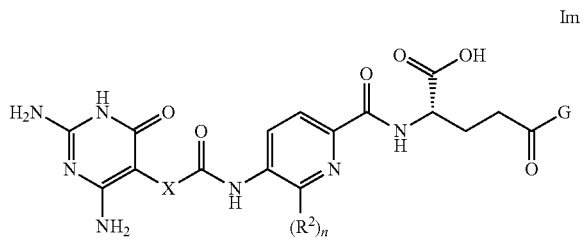

wherein $R^2$, X, and G are as defined herein, and n is 0 or 1, in particular 1.

In some particular embodiments of a compound of formula Ig, Ih, Ii, Ij, Ik, or Im, G represents OH or a mono-glutamic acid group. In some more particular embodiments of a compound of formula Ig, Ih, Ii, Ij, Ik, or Im, G represents OH. In some other embodiments of a compound of formula Ig, Ih, Ii, Ij, Ik, or Im, G represents a mono- or poly-glutamic acid group, e.g. a mono-glutamic acid group.

In some further particular embodiments of a compound of formula I, e.g. a compound of any one of formulas Ia, Ib, Ic, Id, Ie, If, Ig, Ih, Ii, Ij, Ik, or Im, in particular any one of formulas Ib, Ic If, Ih, or Ij, $R^2$ represents a moiety selected from halo and —$R^{1a}$; e.g. fluoro, chloro, and $C_{1-3}$ alkyl (such as methyl) optionally substituted by one or more fluoro; in particular halo, e.g. fluoro.

In some further particular embodiments of a compound of formula I, in particular a compound of formula Id, Ie, Ik, or Im, $R^2$ represents a moiety selected from halo, —$R^{1a}$, —$OR^{1b}$ and phenyl, in particular -$R^{1a}$, —$OR^{1b}$ and phenyl; e.g. $R^2$ represents ethenyl, methoxy, cyclopropyloxy, phenoxy or phenyl. In some embodiments of a compound of formula Id, Ie, Ik, or Im, $R^2$ represents —$OR^{1b}$.

In some embodiments of a compound of formula I
$R^1$ represents
(i) $C_{1-6}$ alkyl, $C_{2-6}$ alkenyl or $C_{2-6}$ alkynyl each optionally substituted by one or more groups independently selected from oxy and $A^1$,
(ii) aryl optionally substituted by one or more groups independently selected from oxy and $A^2$, or
(ii) —$(CH_2)_2C(O)$—G;
each $R^2$ independently represents
(i) halo, —$NO_2$, —CN, —$R^{1a}$, —$OR^{1b}$, —$S(O)_pR^{1c}$, —$S(O)_qN(R^{1d})(R^{1e})$, —$N(R^{1f})S(O)_rR^{1g}$, —$N(R^{1h})(R^{1i})$, —$C(O)OR^{1j}$, or —$C(O)N(R^{1k})(R^{1l})$, or
(ii) aryl optionally substituted by one or more groups independently selected from oxy and $A^5$;
n represents 0 to 3;
X represents —$N(R^3)$— or —$C(R^4)_2$—;
$R^3$ represents H or $C_{1-3}$ alkyl optionally substituted by one or more fluoro;
each $R^4$ independently represents H, fluoro or $C_{1-3}$ alkyl optionally substituted by one or more fluoro;
G represents —OH, or a mono- or poly-glutamic acid group;
each of $A^1$, $A^2$ and $A^5$ independently represents
(i) halo, —$NO_2$, —CN, —$R^{2a}$, —$OR^{2b}$, —$S(O)_pR^{2c}$, —$S(O)_qN(R^{2d})(R^{2e})$, —$N(R^{2f})S(O)_rR^{2g}$, —$N(R^{2h})(R^{2i})$, —$C(O)OR^{2j}$, or —$C(O)N(R^{2k})(R^{2l})$,
(ii) aryl optionally substituted by one or more groups independently selected from oxy and $B^1$, or
(iii) heteroaryl optionally substituted by one or more groups independently selected from oxy and $B^2$;
each $R^{1a}$ and $R^{2a}$ independently represents $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $D^1$;
each $R^{1b}$ to $R^{1l}$ and $R^{2b}$ to $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $D^1$, or
(ii) aryl optionally substituted by one or more groups independently selected from oxy and $D^2$;
each of $B^1$ and $B^2$ independently represents halo, —$NO_2$, —CN, —$R^{3a}$, —$OR^{3b}$, —$S(O)_pR^{3c}$, —$S(O)_qN(R^{3d})(R^{3e})$, —$N(R^{3f})S(O)_rR^{3g}$, —$N(R^{3h})(R^{3i})$, —$C(O)OR^{3j}$, or —$C(O)N(R^{3k})(R^{3l})$;
each $D^1$ independently represents halo, —$NO_2$, —CN, —$OR^{4b}$, —$S(O)_pR^{4c}$, —$S(O)_qN(R^{4d})(R^{4e})$, —$N(R^{4f})S(O)_rR^{4g}$, —$N(R^{4h})(R^{4i})$, —$C(O)OR^{4j}$, or —$C(O)N(R^{4k})(R^{4l})$;
each $D^2$ independently represents halo, —$NO_2$, —CN, —$R^{4a}$, —$OR^{4b}$, —$S(O)_pR^{4c}$, —$S(O)_qN(R^{4d})(R^{4e})$, —$N(R^{4f})S(O)_rR^{4g}$, —$N(R^{4h})(R^{4i})$, —$C(O)OR^{4j}$, or —$C(O)N(R^{4k})(R^{4l})$;
each $R^{3a}$ and $R^{4a}$ independently represents $C_{1-3}$ alkyl optionally substituted with one or more fluoro;
each $R^{3b}$ to $R^{3'}$, and $R^{4b}$ to $R^{4'}$ independently represents H or $C_{1-3}$ alkyl optionally substituted with one or more fluoro; and
each p, q and r independently represents 0, 1 or 2.

In some of the above embodiments, any aryl is phenyl and any heteroaryl is a 5- or 6-membered monocyclic ring containing 1, 2, 3 or 4 heteroatoms (e.g. N, O or S) in the ring.

In some embodiments,
R$^1$ represents
(i) C$_{1-6}$ alkyl, C$_{2-6}$ alkenyl or C$_{2-6}$ alkynyl each optionally substituted by one or more groups independently selected from oxy and A$^1$,
(ii) phenyl, or
(iii) —(CH$_2$)$_2$C(O)—G;
each R$^2$ independently represents
(i) halo, —NO$_2$, —CN, —R$^{1a}$, —OR$^{1b}$, —S(O)$_p$R$^{1c}$, —S(O)$_q$(R$^{1d}$)(R$^{1e}$), —N(R$^{1f}$)S(O)$_r$R$^{1g}$, —N(R$^{1h}$)(R$^{1i}$), —C(O)OR$^{1j}$, or —C(O)N(R$^{1k}$)(R$^{1l}$), or
(ii) phenyl;
n represents 0 to 3;
X represents —N(R$^3$)— or —C(R$^4$)$_2$—;
R$^3$ represents H or C$_{1-3}$ alkyl optionally substituted by one or more fluoro;
each R$^4$ independently represents H, fluoro or C$_{1-3}$ alkyl optionally substituted by one or more fluoro;
G represents —OH, or a mono- or poly-glutamic acid group;
each A$^1$ independently represents
(i) halo, —NO$_2$, —CN, —R$^{2a}$, —OR$^{2b}$, —S(O)$_p$R$^{2c}$, —S(O)$_q$N(R$^{2d}$)(R$^{2e}$), —N(R$^{2f}$)S(O)$_r$R$^{2g}$, —N(R$^{2h}$)(R$^{2i}$), —C(O)OR$^{2j}$, or —C(O)N(R$^{2k}$)(R$^{2l}$),
(ii) phenyl, or
(iii) heteroaryl;
each R$^{1a}$ and R$^{2a}$ independently represents C$_{1-6}$ alkyl, C$_{2-6}$ alkenyl or C$_{2-6}$ alkynyl, wherein each such alkyl, alkenyl or alkynyl group is optionally substituted by one or more groups independently selected from oxy and fluoro;
each R$^{1b}$ to R$^{1l}$ and R$^{2b}$ to R$^{2l}$ independently represents H or
(i) C$_{1-6}$ alkyl, C$_{2-6}$ alkenyl or C$_{2-6}$ alkynyl, wherein each such alkyl, alkenyl or alkynyl group is optionally substituted by one or more groups independently selected from oxy and fluoro, or
(ii) phenyl; and
each p, q and r independently represents 0, 1 or 2.

In some embodiments,
R$^1$ represents
(i) C$_{1-6}$ alkyl, C$_{2-6}$ alkenyl or C$_{2-6}$ alkynyl each optionally substituted by one or more groups independently selected from oxy and A$^1$,
(ii) phenyl, or
(iii) —(CH$_2$)$_2$C(O)—G;
each R$^2$ independently represents
(i) halo, —R$^{1a}$, or —OR$^{1b}$, or
(ii) phenyl;
n represents 0 to 3;
X represents —N(R$^3$)— or —C(R$^4$)$_2$—;
R$^3$ represents H or C$_{1-3}$ alkyl optionally substituted by one or more fluoro;
each R$^4$ independently represents H, fluoro or C$_{1-3}$ alkyl optionally substituted by one or more fluoro;
G represents —OH, or a mono- or poly-glutamic acid group;
each A$^1$ independently represents
(i) halo, —OR$^{2b}$, —N(R$^{2f}$)S(O)$_2$R$^{2g}$, or —C(O)OR$^{2j}$,
(ii) phenyl, or
(iii) heteroaryl;
each R$^{1a}$ independently represents C$_{1-6}$ alkyl, C$_{2-6}$ alkenyl or C$_{2-6}$ alkynyl, wherein each such alkyl, alkenyl or alkynyl group is optionally substituted by one or more fluoro; and
each R$^{1b}$, R$^{2b}$, R$^{2f}$, R$^{2g}$ and R$^{2j}$ independently represents H or
(i) C$_{1-6}$ alkyl, C$_{2-6}$ alkenyl or C$_{2-6}$ alkynyl, wherein each such alkyl, alkenyl or alkynyl group is optionally substituted by one or more fluoro, or
(ii) phenyl.

In some further embodiments,
R$^1$ represents
(i) C$_{1-6}$ alkyl, C$_{2-6}$ alkenyl or C$_{2-6}$ alkynyl each optionally substituted by one or more groups independently selected from oxy and A$^1$,
(ii) phenyl, or
(iii) —(CH$_2$)$_2$C(O)—G;
each R$^2$ independently represents
(i) halo, —R$^{1a}$, or —OR$^{1b}$, or
(ii) phenyl;
n represents 0 to 3;
X represents —N(R$^3$)— or —C(R$^4$)$_2$—;
R$^3$ represents H or C$_{1-3}$ alkyl optionally substituted by one or more fluoro; each R$^4$ independently represents H, fluoro or C$_{1-3}$ alkyl optionally substituted by one or more fluoro;
G represents —OH, or a mono-glutamic acid group;
each A$^1$ independently represents
(i) halo, —N(H)S(O)$_2$R$^{2g}$, or —C(O)OR$^{2j}$,
(ii) phenyl, or
(iii) heteroaryl;
each R$^{1a}$ independently represents C$_{1-6}$ alkyl, C$_{2-6}$ alkenyl or C$_{2-6}$ alkynyl, wherein each such alkyl, alkenyl or alkynyl group is optionally substituted by one or more fluoro; and
each R$^{1b}$, R$^{2g}$ and R$^{2j}$ independently represents H or
(i) C$_{1-6}$ alkyl, C$_{2-6}$ alkenyl or C$_{2-6}$ alkynyl, wherein each such alkyl, alkenyl or alkynyl group is optionally substituted by one or more fluoro, or
(ii) phenyl.

In some of the above embodiments, n represents 0, 1 or 2; e.g. 0 or 1. In some other of the above embodiments, n represents 1, 2 or 3, e.g. 1 or 2, in particular 1. In some of the above embodiments, n represents 0.

In some further embodiments,
R$^1$ represents
(i) C$_{1-6}$ alkyl, C$_{2-6}$ alkenyl or C$_{2-6}$ alkynyl each optionally substituted by one or more groups independently selected from oxy and A$^1$,
(ii) phenyl, or
(iii) —(CH$_2$)$_2$C(O)—G;
R$^2$ represents
(i) halo, —R$^{1a}$, or —OR$^{1b}$, or
(ii) phenyl;
n represents 0 or 1;
X represents —N(R$^3$)— or —C(R$^4$)$_2$—;
R$^3$ represents H or C$_{1-3}$ alkyl optionally substituted by one or more fluoro;
each R$^4$ independently represents H, fluoro or C$_{1-3}$ alkyl optionally substituted by one or more fluoro;
G represents —OH, or a mono-glutamic acid group;
each A$^1$ independently represents
(i) halo, —N(H)S(O)$_2$R$^{2g}$, or —C(O)OR$^{2j}$,
(ii) phenyl, or
(iii) heteroaryl;
R$^{1a}$ represents C$_{1-6}$ alkyl, C$_{2-6}$ alkenyl or C$_{2-6}$ alkynyl, wherein each such alkyl, alkenyl or alkynyl group is optionally substituted by one or more fluoro; and
each R$^{1b}$, R$^{2g}$ and R$^{2j}$ independently represents H or
(i) C$_{1-6}$ alkyl, C$_{2-6}$ alkenyl or C$_{2-6}$ alkynyl, wherein each such alkyl, alkenyl or alkynyl group is optionally substituted by one or more fluoro, or
(ii) phenyl.

In some further embodiments,

R$^1$ represents (i) C$_{1-6}$ alkyl, C$_{2-6}$ alkenyl or C$_{2-6}$ alkynyl each optionally substituted by one or more groups independently selected from oxy and A$^1$, (ii) phenyl, or (iii) —(CH$_2$)$_2$C(O)—G;

R$^2$ represents (i) halo, —R$^{1a}$, or —OR$^{1b}$, or (ii) phenyl;

n represents 0 or 1;

X represents —NH— or —CH$_2$—;

G represents —OH, or a mono-glutamic acid group;

each A$^1$ independently represents (i) halo, —N(H)S(O)$_2$R$^{29}$, or —C(O)OR$^2$, (ii) phenyl, or (iii) heteroaryl;

R$^{1a}$ represents C$_{1-6}$ alkyl, C$_{2-6}$ alkenyl or C$_{2-6}$ alkynyl, wherein each such alkyl, alkenyl or alkynyl group is optionally substituted by one or more fluoro; and each R$^{1b}$, R$^{2g}$ and R$^{2j}$ independently represents H or (i) C$_{1-6}$ alkyl, C$_{2-6}$ alkenyl or C$_{2-6}$ alkynyl, wherein each such alkyl, alkenyl or alkynyl group is optionally substituted by one or more fluoro; or (ii) phenyl.

In some embodiments,

R$^1$ represents (i) C$_{1-6}$ alkyl, C$_{2-6}$ alkenyl or C$_{2-6}$ alkynyl each optionally substituted by one or more (e.g. one) groups independently selected from oxy and A$^1$, (ii) phenyl, or (iii) —(CH$_2$)$_2$C(O)—G;

R$^2$ represents (i) halo, —R$^{1a}$, or —OR$^{1b}$, or (ii) phenyl;

n represents 0 or 1;

X represents —NH— or —CH$_2$—;

G represents —OH, or a mono- or poly-glutamic acid group;

each A$^1$ independently represents (i) —N(R$^{2f}$)S(O)$_2$R$^{29}$, or —C(O)OR$^{2j}$, (ii) phenyl, or (iii) heteroaryl;

each R$^{1a}$ independently represents (i) C$_{1-6}$ alkyl, C$_{2-6}$ alkenyl or C$_{2-6}$ alkynyl, wherein each such alkyl, alkenyl or alkynyl group is optionally substituted by one or more fluoro;

each R$^{1b}$, R$^{1f}$, R$^{1j}$, and R$^{1k}$ independently represents H or (i) C$_{1-6}$ alkyl, C$_{2-6}$ alkenyl or C$_{2-6}$ alkynyl, wherein each such alkyl, alkenyl or alkynyl group is optionally substituted by one or more fluoro; and (ii) phenyl, In some further embodiments, R$^1$ represents C$_{1-6}$ alkyl, C$_{2-6}$ alkenyl or C$_{2-6}$ alkynyl each optionally substituted by one or more groups independently selected from A$^1$, or —(CH$_2$)$_2$C(O)—G;

R$^2$ represents halo, —R$^{1a}$, or —OR$^{1b}$;

n represents 0 or 1;

X represents —NH— or —CH$_2$—;

G represents —OH, or a mono-glutamic acid group;

each A$^1$ independently represents —C(O)OH, phenyl, or heteroaryl;

R$^{1a}$ represents C$_{1-6}$ alkyl, C$_{2-6}$ alkenyl or C$_{2-6}$ alkynyl, wherein each such alkyl, alkenyl or alkynyl group is optionally substituted by one or more fluoro; and R$^{1b}$ represents H, C$_{1-6}$ alkyl, C$_{2-6}$ alkenyl or C$_{2-6}$ alkynyl, wherein each such alkyl, alkenyl or alkynyl group is optionally substituted by one or more fluoro; or phenyl.

In some further embodiments,

R$^1$ represents C$_{1-6}$ alkyl, optionally substituted by one or more groups independently selected from A$^1$, or —(CH$_2$)$_2$C(O)—G;

R$^2$ represents halo, —R$^{1a}$, or —OR$^{1b}$;

n represents 0 or 1;

X represents —NH— or —CH$_2$—;

G represents —OH, or a mono-glutamic acid group;

each A$^1$ independently represents —C(O)OH, phenyl, or heteroaryl;

R$^{1a}$ represents C$_{1-6}$ alkyl, C$_{2-6}$ alkenyl or C$_{2-6}$ alkynyl, wherein each such alkyl, alkenyl or alkynyl group is optionally substituted by one or more fluoro; and R$^{1b}$ represents C$_{1-6}$ alkyl, C$_{2-6}$ alkenyl or C$_{2-6}$ alkynyl, wherein each such alkyl, alkenyl or alkynyl group is optionally substituted by one or more fluoro; or phenyl.

In some further embodiments,

R$^1$ represents C$_{1-6}$ alkyl, optionally substituted by one or more groups independently selected from A$^1$, or —(CH$_2$)$_2$C(O)—G;

R$^2$ represents halo;

n represents 0 or 1;

X represents —NH— or —CH$_2$—;

G represents —OH, or a mono-glutamic acid group; and each A$^1$ independently represents —C(O)OH, phenyl, or heteroaryl.

In some further embodiments,

R$^1$ represents C$_{1-6}$ alkyl, optionally substituted by one or more groups independently selected from A$^1$, or —(CH$_2$)$_2$C(O)—G;

R$^2$ represents halo;

n represents 0 or 1;

X represents —NH— or —CH$_2$—;

G represents —OH, or a mono-glutamic acid group; and each A$^1$ independently represents —C(O)OH; or (ii) heteroaryl.

In some further embodiments, R$^1$ represents C$_{1-6}$ alkyl, optionally substituted by one or more (e.g. one) —C(O)OH; R$^2$ represents halo, e.g. F; n represents 0 or 1; and X represents —NH— or —CH$_2$—.

In some further embodiments, R$^1$ represents C$_{1-6}$ alkyl, optionally substituted by —C(O)OH; R$^2$ represents halo, e.g. F; n represents 0 or 1; and X represents —NH— or —CH$_2$—; e.g. —CH$_2$—.

In some of the above embodiments, n represents 1.

In some further embodiments, R$^1$ represents C$_{1-6}$ alkyl, optionally substituted by —C(O)OH; R$^2$ represents halo, e.g. F; n represents 1; and X represents —CH$_2$—.

In some further embodiments, R$^1$ represents —(CH$_2$)$_2$C(O)—G; R$^2$ represents halo; n represents 0 or 1; X represents —NH— or —CH$_2$—; and G represents —OH, or a mono-glutamic acid group.

In some further embodiments, R$^1$ represents —(CH$_2$)$_2$C(O)OH; R$^2$ represents halo; n represents 0 or 1; and X represents —NH— or —CH$_2$—.

In some further embodiments, R$^1$ represents —(CH$_2$)$_2$C(O)OH; R$^2$ represents halo; n represents 0 or 1; and X represents —CH$_2$—.

In some further embodiments, R$^1$ represents —(CH$_2$)$_2$C(O)OH; R$^2$ represents F; n represents 0 or 1; and X represents —NH— or —CH$_2$—.

In some further embodiments, $R^1$ represents —$(CH_2)_2C(O)OH$; $R^2$ represents F; n represents 0 or 1; and X represents —$CH_2$—.

In some further embodiments, $R^1$ represents —$(CH_2)_2C(O)OH$; $R^2$ represents F; n represents 1; and X represents —NH— or —$CH_2$—.

In some further embodiments, $R^1$ represents —$(CH_2)_2C(O)OH$; $R^2$ represents halo, e.g. F; n represents 1; and X represents —$CH_2$—.

In some further embodiments, $R^1$ represents isopropyl, cyclopentylmethyl, cyclohexyl, phenyl, benzyl, 2-phenylethyl, 3-oxo-3-(phenylsulfonamido)propyl, 2-(1H-tetrazol-5-yl)ethyl, carboxymethyl, 2-carboxyethyl, 3-carboxypropyl, and 3-((1,3-dicarboxypropyl)amino)-3-oxopropyl;

$R^2$ represents fluoro, chloro, methyl, trifluoromethyl, ethenyl, cyclopropyloxy, phenoxy, or phenyl;

n represents 0 or 1; and

X represents NH or $CH_2$.

It should be realized that any reference to a compound of formula I as defined herein, also should be construed as a reference to a compound of any one of the formulas Ia, Ib, Ic, Id, Ie, If, Ig, Ih, Ii, Ij, Ik, and Im, unless otherwise specified or apparent from the context.

Although compounds of the invention may possess pharmacological activity as such, certain pharmaceutically-acceptable (e.g. "protected") derivatives of compounds of the invention may exist or be prepared which may not possess such activity but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the active compounds of the invention to which they are metabolised), may also be described as "prodrugs".

For the avoidance of doubt, compounds of the invention are therefore useful because they possess pharmacological activity, and/or are metabolised in the body following oral or parenteral administration to form compounds that possess pharmacological activity.

Particular prodrugs of compounds of the invention that may be mentioned include pharmaceutically acceptable esters (i.e. compounds of the invention wherein one or more carboxylic acid moiety required therein is instead provided in the form of a pharmaceutically acceptable ester thereof). The skilled person will be aware of moieties used in the formation of pharmaceutically acceptable esters. Such esters may include compounds wherein the proton present on the relevant carboxylic acid moiety is replaced with an alkyl (e.g. $C_{1-6}$ alkyl) moiety optionally substituted with one or more (e.g. one) phenyl group, or a phenyl moiety. More particular esters that may be mentioned include methyl, ethyl, propyl, phenyl and benzyl esters, such as ethyl esters.

Further prodrugs that may be mentioned include polymer conjugates (thus forming drug-polymer conjugates), which conjugates may be formed using polymers well-known to those skilled in the art and which may be formed using well-known techniques (e.g. through the formation of an ester thereof).

More particular prodrugs that may be mentioned include those wherein the prodrug is an ester formed by the essential carboxylic acid moiety in compounds of formula I (including all embodiments thereof), such as the corresponding ethyl ester.

Particular compounds of the invention that may be mentioned include those compounds as described in the examples provided herein, and pharmaceutically acceptable salts and/or prodrugs thereof. For the avoidance of doubt, where such compounds of the invention include compounds in a particular salt form, compounds of the invention include those compounds in non-salt form and in the form of any pharmaceutically acceptable salt thereof (which may include the salt form present in such examples).

Medical Uses

As indicated herein, the compounds of the invention, and therefore compositions and kits comprising the same, are useful as pharmaceuticals.

Thus, according to a second aspect of the invention there is provided a compound of the invention, as hereinbefore defined (i.e. a compound as defined in the first aspect of the invention, including all embodiments and particular features thereof), for use as a pharmaceutical (or for use in medicine).

For the avoidance of doubt, references to compounds of the invention (or to compounds as defined in the first aspect of the invention) will include references to compounds of formula I (including all embodiments thereof, such as compounds of formula Ia) and pharmaceutically acceptable salts and/or prodrugs thereof.

As described herein, compounds of the invention may be particularly useful in treating diseases and disorders where modulation of methylenetetrahydrofolate dehydrogenase/cyclohydrolase 2 (MTHFD2) activity exerts a therapeutic effect, such as diseases and disorders characterised by abnormal cell proliferation.

Thus, in a third aspect of the invention, there is provided a compound of the invention, as hereinbefore defined, for use in the treatment or prophylaxis of a disease or disorder where modulation of methylenetetrahydrofolate dehydrogenase/cyclohydrolase 2 (MTHFD2) activity exerts a therapeutic effect.

In an alternative third aspect of the invention, there is provided a method for the treatment or prophylaxis of a disease or disorder where modulation of methylenetetrahydrofolate dehydrogenase/cyclohydrolase 2 (MTHFD2) activity exerts a therapeutic effect comprising administering to a patient in need thereof a therapeutically effective amount of a compound of the invention, as hereinbefore defined.

In a further alternative third aspect of the invention, there is provided the use of a compound of the invention, as hereinbefore defined, for the manufacture of a medicament for the treatment or prophylaxis of a disease or disorder where modulation of methylenetetrahydrofolate dehydrogenase/cyclohydrolase 2 (MTHFD2) activity exerts a therapeutic effect.

The skilled person will understand that references to the treatment of a particular condition (or, similarly, to treating that condition) will take their normal meanings in the field of medicine. In particular, the terms may refer to achieving a reduction in the severity and/or frequency of occurrence of one or more clinical symptom associated with the condition, as adjudged by a physician attending a patient having or being susceptible to such symptoms.

As used herein, references to prophylaxis will include references to the prophylaxis of the disease or disorder (and vice-versa). As such, references to prophylaxis may also be references to prevention (and preventing), and vice versa. In particular, such terms term may refer to achieving a clinically relevant reduction (for example, at least a 10% reduction, such as at least a 20%, 30% or 40% reduction, e.g. at least a 50% reduction) in the likelihood of the patient (or healthy subject) developing the condition (which may be understood as meaning that the condition of the patient changes such that patient is diagnosed by a physician as having, e.g. requiring treatment for, the relevant disease or disorder).

In particular embodiments, references to treatment or prophylaxis may be replaced with references to treatment.

As used herein, references to a patient (or to patients) will refer to a living subject being treated, including mammalian (e.g. human) patients. In particular embodiments, references to a patient will refer to human patients. In alternative embodiments, references to a patient may refer to an animal, such as household pets (e.g. cats, dogs, rabbits, hamsters, guinea pigs, mice, and the like) or livestock (e.g. cows, sheep, pigs, horses, chickens, geese, turkeys, deer, buffalo, and the like).

For the avoidance of doubt, the skilled person will understand that such treatment will be performed in a patient (or subject) in need thereof. The need of a patient (or subject) for such treatment may be assessed by those skilled the art using routine techniques. As used herein, the terms disease and disorder (and, similarly, the terms condition, illness, medical problem, and the like) may be used interchangeably.

As used herein, the term effective amount will refer to an amount of a compound that confers a therapeutic effect on the treated patient. The effect may be observed in a manner that is objective (i.e. measurable by some test or marker) or subjective (i.e. the subject gives an indication of and/or feels an effect). In particular, the effect may be observed (e.g. measured) in a manner that is objective, using appropriate tests as known to those skilled in the art.

For the avoidance of doubt, the skilled person will understand that modulation of MTHFD2 activity may refer to achieving an increase or decrease in the in vivo activity of the enzyme.

In particular, references to modulation of MTHFD2 may refer to inhibition of the enzyme, in respect of which the skilled person will understand that such inhibition may be identified as being a clinically relevant degree of inhibition. For example, such inhibition may be considered to be at least 10% inhibition (such as at least 20%, 30%, 40% or, particularly, 50% inhibition).

In particular embodiments, the disease or disorder where modulation of methylenetetrahydrofolate dehydrogenase/cyclohydrolase 2 (MTHFD2) activity exerts a therapeutic effect is a cell proliferation disorder.

The skilled person will be able to identify various diseases and disorders characterised by abnormal cell proliferation.

In particular embodiments (i.e. particular embodiments of the third aspect of the invention), the cell proliferation disorder is selected from the group consisting of: cancer; inflammation; autoimmune diseases; and host-versus-graft diseases.

As described herein, the compounds of the first aspect of the invention may find particular utility in the treatment of inflammation and autoimmune diseases. Thus, in certain embodiments, the cell proliferation disorder is inflammation and/or an autoimmune disease.

For the avoidance of doubt, the inflammation may be acute or chronic. In particular embodiments, the inflammation is chronic.

For the avoidance of doubt, the inflammation may be local and/or systemic. In particular embodiments, the inflammation is systemic.

In more particular embodiments, the inflammation or autoimmune disease (e.g. the inflammation) is of (i.e. affects) the:
lungs (such as asthma, chronic obstructive pulmonary disease (CORD), acute lung injury/acute respiratory distress and/or interstitial lung disease); joints (such as rheumatoid arthritis);
digestive system, e.g. the intestine (such as irritable bowel syndrome (IBS), ulcerative colitis and/or Crohn's disease);
skin (such as eczema and/or psoriasis); and/or
liver (such as inflammation resulting from chronic hepatitis).

In particular embodiments, the cell proliferation disorder is inflammation, an autoimmune disease or a host-versus-graft disease.

Particular autoimmune, inflammatory and host-versus-graft diseases that may be mentioned include:
asthma, CORD, rheumatoid arthritis, systemic lupus erythematosus, irritable bowel syndrome (IBS), Crohn's disease, ulcerative colitis, multiple sclerosis, lymphoproliferative diseases (e.g. those caused by Epstein Barr virus and cytomegalovirus), rejection after organ transplantation, Wegener's granulomatosus, psoriasis, Mb Bechterews, Behcets disease, Guillain Barre, dermatomyositis, myositis, polymyositis, primary biliary cirrhosis, anti-phospholipid syndrome, autoimmune hepatitis, autoimmune cardiomyopathy, alopecia areata, atherosclerosis, type 1 diabetes, autoimmune uveitis, Goodpasteure's syndrome, Graves' disease, Hashimoto's disease, mixed connective tissue disease, myasthenia gravis, pemphigus vulgaris, pernicious anemia, Sjögren's syndrome, giant cell arteritis, vasculitis, Churg-Strauss syndrome, postpolio syndrome, idiopathic thrombocytopenic purpura, Peyronie disease and Dupuytren's contracture.

Particular host-versus-graft diseases that may be mentioned include rejection after organ transplantation.

Particular types of inflammation that may be mentioned include inflammation of the lungs (such as asthma, chronic obstructive pulmonary disease (COPD), acute lung injury/acute respiratory distress and/or interstitial lung disease).

In further embodiments, the inflammation may also be systemic inflammation triggered by an autoimmune response, as may occur in conditions such as sepsis.

As also described herein, the compounds of the first aspect of the invention may find particular utility in the treatment of cancers. Thus, in certain embodiments, the cell proliferation disorder is cancer (i.e. a cancer).

In particular embodiments, the cancer is a solid tumour cancer. In further embodiments, the cancer is a blood cell cancer, such as leukaemia.

In more particular embodiments, the cancer is selected from the group consisting of:
leukemia (such as acute lymphoblastic leukemia, acute monocytic leukemia, acute myelogenous leukemia, chronic lymphocytic leukemia, chronic myelogenous leukemia, acute myeloid leukemia, and/or acute promyelocytic leukemia);

lymphomas (such as Burkitt's lymphoma);

carcinomas, including adenocarcinomas (such as lung carcinoma, e.g. large cell lung carcinomas and/or small cell lung carcinomas, cervical adenocarcinomas, colorectal adenocarcinomas, colorectal carcinomas, prostate carcinomas, e.g. prostate adenocarcinomas, renal carcinomas, e.g. renal cell adenocarcinomas and/or endometrioid adenocarcinomas);

lymphoblastomas;

glioblastomas (such as glioblastoma multiforme and/or malignant glioblastoma);

neuroblastomas;

lymphomas (such as mantle cell lymphoma); and sarcomas (such as osteosarcoma).

Specific cancers that may be mentioned include lung cancer (e.g. large cell lung cancer and small cell lung cancer), breast cancer, renal cancer, colorectal cancer, prostate cancer, brain cancer (e.g. glioblastoma) and leukaemia. More particular cancers that may be mentioned include lung cancer (e.g. large cell lung cancer and small cell lung cancer).

Further cancers that may be mentioned include neuroblastoma.

Pharmaceutical Compositions

As described herein, compounds of the invention are useful as pharmaceuticals. Such compounds may be administered alone or may be administered by way of known pharmaceutical compositions/formulations.

In a fourth aspect of the invention, there is provided a pharmaceutical composition comprising a compound of the invention as defined herein, and optionally one or more pharmaceutically-acceptable excipient.

As used herein, the term pharmaceutically-acceptable excipients includes references to vehicles, adjuvants, carriers, diluents, pH adjusting and buffering agents, tonicity adjusting agents, stabilizers, wetting agents and the like. In particular, such excipients may include adjuvants, diluents or carriers.

In a particular embodiment of the fourth aspect of the invention, the pharmaceutical composition comprises at least one pharmaceutically-acceptable excipient.

For the avoidance of doubt, references herein to compounds of invention being for particular uses (and, similarly, to uses and methods of use relating to compounds of the invention) may also apply to pharmaceutical compositions comprising compounds of the invention, as described herein.

Thus, in a fifth aspect of the invention, there is provided a pharmaceutical composition as defined in the fourth aspect of the invention for use in the treatment a cell proliferation disorder (as defined herein, with reference to the third aspect of the invention and all embodiments thereof).

The skilled person will understand that compounds of the invention may act systemically and/or locally (i.e. at a particular site), and may therefore be administered accordingly using suitable techniques known to those skilled in the art. The skilled person will understand that compounds and compositions as described herein will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form.

Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

Other formulations that may be mentioned include those in which the active ingredient(s) is encapsulated in the form of a vesicle, such as wherein the formulation comprises the active ingredient(s) in the form of micelles, liposomes, virosomes, niosomes, nanospheres, nanocapsules or polymersomes. The formulation may alternatively (or additionally) comprise the active ingredient(s) in the form of, or disbursed on and/or within, nanoparticles (which nanoparticles, when acting as drug carriers, may be composed of suitable carrier materials, as known to those skilled in the art).

Depending on e.g. potency and physical characteristics of the compound of the invention (i.e. active ingredient), pharmaceutical formulations that may be mentioned include those in which the active ingredient is present in an amount that is at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The skilled person will understand that compounds of the invention may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 1 mg/kg of body weight per day (mg/kg/day) to about 200 mg/kg/day. For example, treatment with such compounds may comprise administration of a formulations typically containing between about 100 mg to about 10,000 mg, such as a dose of about 6,000 mg, of the active ingredient(s). Advantageously, treatment may comprise administration of such compounds and compositions in a single daily dose, or the total daily dosage may be administered in divided doses of two, three or four times daily.

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "±10%", or the like (or by indicating a variance of a specific amount calculated based on the relevant value). It is also contemplated that, at each instance, such terms may be deleted.

For the avoidance of doubt, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. Although the above-mentioned dosages are exemplary of the average case, there can, of course, be individual instances where higher or lower dosage ranges are merited, and such doses are within the scope of the invention.

Combinations and Kits-of-Parts

The skilled person will understand that treatment with compounds of the invention may further comprise (i.e. be combined with) further treatment(s) for the same condition. In particular, treatment with compounds of the invention may be combined with means for the treatment of a disease or disorder where modulation of methylenetetrahydrofolate dehydrogenase/cyclohydrolase 2 (MTHFD2) activity exerts a therapeutic effect, as described herein (such as inflammation and/or cancer, as described herein), such as treatment with one or more other therapeutic agent that is useful in the treatment of a cell proliferation disorder and/or one or more physical method used in the treatment of a cell proliferation disorder (such as, particularly in the treatment of cancer, treatment through surgery and/or radiotherapy), as known to those skilled in the art.

More particularly, compounds of the invention may be combined with one or more other (i.e. different) therapeutic agents (i.e. agents that are not compounds of the invention) that are useful in the treatment of a disease or disorder where modulation of methylenetetrahydrofolate dehydrogenase/cyclohydrolase 2 (MTHFD2) activity exerts a therapeutic effect. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

In particular embodiments, compounds of the invention may be used (i.e. in the treatment of a disease or disorder where modulation of methylenetetrahydrofolate dehydrogenase/cyclohydrolase 2 (MTHFD2) activity exerts a therapeutic effect) as a adjuvant therapy, which may be refer to their administration following (i.e. as part of the same treatment cycle as) treatment with another means for treatment of the same disease or disorder, such as those described herein.

Thus, according to a sixth aspect of the invention, there is provided a combination product comprising:

(I) a compound of the invention, as hereinbefore defined (i.e. in the first aspect of the invention, including all embodiments and particular features thereof); and (II) one or more other therapeutic agent that is useful in the treatment of a disease or disorder where modulation of methylenetetrahydrofolate dehydrogenase/cyclohydrolase 2 (MTHFD2) activity exerts a therapeutic effect (as described herein), wherein each of components (I) and (II) is formulated in admixture, optionally with one or more a pharmaceutically-acceptable excipient.

In a seventh aspect of the invention, there is provided a kit-of-parts comprising:

(a) a pharmaceutical formulation as hereinbefore defined (i.e. in the fifth aspect of the invention); and (b) one or more other therapeutic agent that is useful in the treatment of a disease or disorder where modulation of methylenetetrahydrofolate dehydrogenase/cyclohydrolase 2 (MTHFD2) activity exerts a therapeutic effect (as described herein), optionally in admixture with one or more pharmaceutically-acceptable excipient, which components (a) and (b) are each provided in a form that is suitable for administration in conjunction (i.e. concomitantly or sequentially) with the other.

With respect to the kits-of-parts as described herein, by "administration in conjunction with" (and similarly "administered in conjunction with") we include that respective formulations are administered, sequentially, separately or simultaneously, as part of a medical intervention directed towards treatment of the relevant condition.

Thus, in relation to the present invention, the term "administration in conjunction with" (and similarly "administered in conjunction with") includes that the two active ingredients (i.e. a compound of the invention and a further agent for the treatment of a cell proliferation disorder, or compositions comprising the same) are administered (optionally repeatedly) either together, or sufficiently closely in time, to enable a beneficial effect for the patient, that is greater, over the course of the treatment of the relevant condition, than if either agent is administered (optionally repeatedly) alone, in the absence of the other component, over the same course of treatment. Determination of whether a combination provides a greater beneficial effect in respect of, and over the course of, treatment of a particular condition will depend upon the condition to be treated but may be achieved routinely by the skilled person.

Further, in the context of the present invention, the term "in conjunction with" includes that one or other of the two formulations may be administered (optionally repeatedly) prior to, after, and/or at the same time as, administration of the other component. When used in this context, the terms "administered simultaneously" and "administered at the same time as" includes instances where the individual doses of the compound of the invention and the additional compound for the treatment of cancer, or pharmaceutically acceptable salts thereof, are administered within 48 hours (e.g. within 24 hours, 12 hours, 6 hours, 3 hours, 2 hours, 1 hour, 45 minutes, 30 minutes, 20 minutes or 10 minutes) of each other.

For the avoidance of doubt, references to combination products include references to products containing each of the agents indicated in a single product (e.g. in a single formulation, such as a single capsule or tablet).

In certain instances (for example, where two therapeutic agents are present in the product), combination products may also include conjugate products, wherein two therapeutic agents are joined via a covalent bond (which bond may be cleaved in use, i.e. in vivo, to release the two separate agents).

As used herein, references to other therapeutic agents that are "useful" in a certain manner (e.g. in the treatment of a certain disease or disorder) will refer to agents that are known to be suitable for use in that manner (e.g. agents commonly used for that purpose). Such references may therefore be replaced with references to agents "suitable for" the relevant purpose.

Other therapeutic agents useful in the treatment of a disease or disorder where modulation of methylenetetrahydrofolate dehydrogenase/cyclohydrolase 2 (MTHFD2) activity exerts a therapeutic effect (as described herein, such as those known for use in the treatment of cancer or inflammation as described herein) will be well-known to those skilled in the art.

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable excipient.

In further aspects of the invention, there is provided a process for the preparation of a combination product or kit-of-parts as hereinbefore defined, which process comprises bringing into association a compound of the invention, as hereinbefore defined, with the other therapeutic agent that is useful in the treatment of the relevant disease or disorder, and at least one pharmaceutically-acceptable excipient.

As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Compounds of the invention as described herein may be prepared in accordance with techniques that are well known to those skilled in the art, such as those described in the examples provided hereinafter.

According to an eighth aspect of the invention there is provided a process for the preparation of a compound of the invention as hereinbefore defined, comprising the step of:

(i) hydrolysis of a corresponding ester of formula II

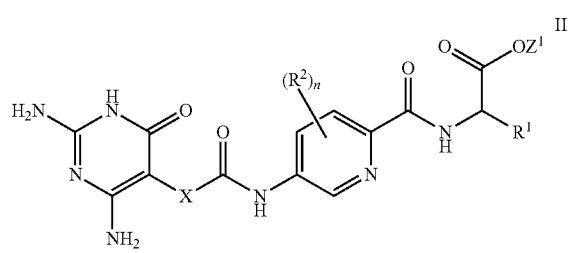

wherein $R^1$, $R^2$ and n are as defined for compounds of formula I herein above (including all embodiments thereof) and $Z^1$ represents (a) $C_{1-6}$ alkyl optionally substituted with one or more phenyl (e.g. methyl, ethyl or benzyl, such as ethyl), or (b) phenyl, under conditions known to those skilled in the art, such as in the presence of aqueous hydroxide ions;

(ii) for compounds comprising one or more additional carboxylic acid moiety (i.e. in addition to the essential carboxylic acid moiety, such as forming part of an $R^2$ or, in particular, an $R^1$ group as described herein), hydrolysis of a compound of formula I or a compound of formula II wherein the one or more additional carboxylic acid moieties are instead present as a group of formula —C(O)$OZ^2$ (which may be referred to herein as compounds of formula III), wherein each $Z^2$ independently represents (a) $C_{1-6}$ alkyl optionally substituted with one or more phenyl (e.g. methyl, ethyl or benzyl, such as ethyl), or (b) phenyl, under conditions known to those skilled in the art, such as in the presence of aqueous hydroxide ions;

(iii) for compounds wherein X represents —NH—, reaction of a compound of formula IV

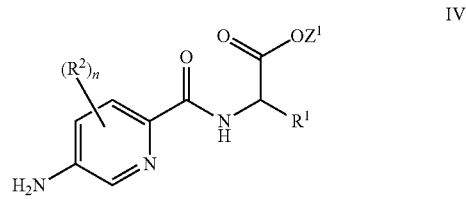

or a suitably protected derivative thereof (e.g. wherein any carboxylic acid groups present in required compounds of the invention are present in the form of a corresponding ester, such as in compounds of formula II and III), wherein $R^1$, $R^2$ and n are as defined for compounds of formula I herein above, with a compound of formula V

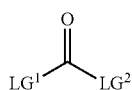

V wherein $LG^1$ and $LG^2$ each represent suitable leaving groups (such as wherein the compound of formula V represents 4-nitrophenyl chloroformate) and a compound of formula VI

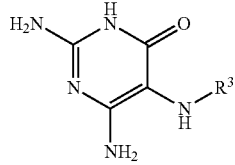

VI wherein $R^3$ is as defined herein, or a suitable salt thereof (e.g. a sulfate salt) under conditions known to those skilled in the art, such as in the presence of a suitable solvent (e.g. THF) and optionally a suitable base (e.g. an amine base, such a $Et_3N$);

(iv) reaction of a compound of formula VII

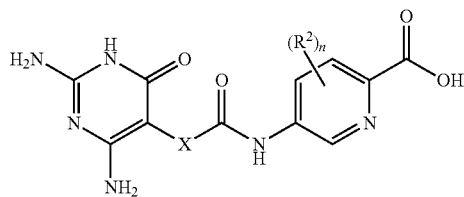

VII or a suitably protected derivative thereof, wherein $R^2$ and n are as defined for compounds of formula herein above, with a compound of formula VIII

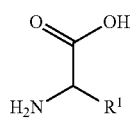

VIII wherein $R^1$ is as defined for compounds of formula I herein above, under conditions known to those skilled in the art, such as under suitable peptide coupling reaction conditions, which may include reaction in the presence of a suitable coupling reagent (e.g. EDCl HCl) and a suitable base (e.g. a suitable amine base, such as $Et_3N$), and in the presence of a suitable solvent (e.g. DMSO); or (v) for compounds wherein X represents —$CH_2$—, reaction of a compound of formula IX

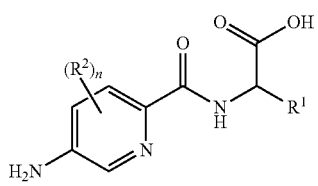

IX or a suitably protected derivative thereof, wherein $R^1$, $R^2$ and n are as defined for compounds of formula I herein above, with a compound of of formula X

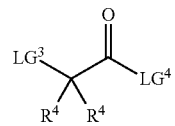

X wherein each $R^4$ is as defined herein and each of $LG^3$ and $LG^4$ independently represents a suitable leaving group (e.g. a suitable halide, such as Cl) and a compound of formula XI

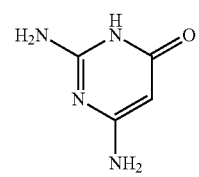

XI or a suitably protected derivative thereof, under conditions known to those skilled in the art, such as in the presence of a suitable base (e.g. a suitable amine base, such as $Et_3N$) and a suitable solvent (e.g. DCM).

Compounds of formulae III, IV, V, VI, VII, VIII, IX, X and XI are either commercially available, are known in the literature, or may be obtained either by analogy with the processes described herein, or by conventional synthetic procedures, in accordance with standard techniques, from available starting materials using appropriate reagents and reaction conditions. Compounds of formula II may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, 3$^{rd}$ edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

Certain compounds that are intermediates in the synthesis of compounds of the invention may also be novel, such as compounds of formula II as described herein.

Thus, in a ninth aspect of the invention, there is provided a compound of formula II

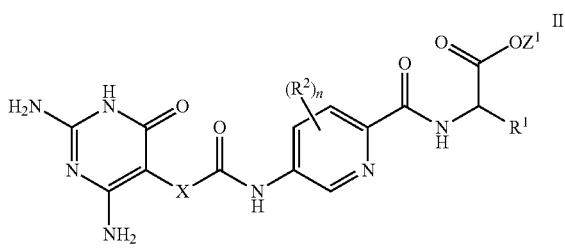

or a pharmaceutically acceptable salt thereof, wherein $R^1$, $R^2$ and n are as defined herein and $Z^1$ represents (a) $C_{1-6}$ alkyl optionally substituted with one or more phenyl, or (b) phenyl.

In some embodiments, $Z^1$ represents $C_{1-6}$ alkyl optionally substituted with one or more phenyl; e.g. $Z^1$ represents $C_{1-6}$ alkyl. In some embodiments, $Z^1$ represents a moiety selected from $C_{1-6}$ alkyl substituted with phenyl, and phenyl. In some embodiments, $Z^1$ represents phenyl. In some of these embodiments, any $C_{1-6}$ alkyl more particularly is selected from $C_{1-3}$ alkyl, e.g. methyl or ethyl. In some embodiments, thus, $Z^1$ represents $C_{1-3}$ alkyl, in particular methyl or ethyl.

Particular compounds of formula II that may be mentioned include those described in the examples provided herein. For the avoidance of doubt, where such compounds include compounds in a particular salt form, particular compounds of formula II include those compounds in non-salt form and in the form of any salt (e.g. pharmaceutically acceptable salt) thereof (which may include the salt form present in such examples).

The skilled person will understand that the substituents as defined herein, and substituents thereon, may be modified one or more times, after or during the processes described above for the preparation of compounds of the invention by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999), the contents of which are incorporated herein by reference.

Without wishing to be bound by theory, it is believed that inhibiting the enzymatic activity of MTHFD2 in human lymphocytes results in selective killing of activated lymphocytes while resting lymphocytes are not affected by the treatment.

In particular, findings presented herein suggest that MTHFD2 inhibitors have the potential to be effective against a variety of cancers forms, with minimal general toxic effects due to the selective over expression of MTHFD2 in cancer versus healthy tissue. MTHFD2 inhibition may also be a suitable adjuvant therapy to be used in conjunction with radiotherapies or other chemotherapeutic approaches.

Compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

EXAMPLES

The present invention will be further described by reference to the following examples, which are not intended to limit the scope of the invention in any way.

In the event that there is a discrepancy between nomenclature and any compounds depicted graphically, then it is the latter that presides (unless contradicted by any experimental details that may be given or unless it is clear from the context).

Abbreviations

The following abbreviations may be used herein:
ACN acetonitrile
aq aqueous
$B(OMe)_3$ trimethylborate
BINAP 2,2'-bis(diphenylphosphino)-1,1'-binaphthyl
Boc tert-butoxycarbonyl
brine saturated aqueous solution of NaCl
CAN ceric ammonium nitrate
$CDCl_3$ deuterated chloroform
$CHCl_3$ chloroform
$Cs_2CO_3$ cesium carbonate
CuCl copper(I) chloride
DBU 1,8-diazabicyclo[5.4.0]undec-7-ene
DCM dichloromethane
DIAD diisopropyl azodicarboxylate
DIEA N,N-diisopropylethylamine
DMAP 4-dimethylaminopyridine
DMF dimethylformamide
DMSO dimethylsulfoxide
DPBS Dulbecco's phosphate-buffered saline
$EC_{50}$ concentration yielding 50% efficacy
EDCl N-(3-dimethylaminopropyl)-N'-ethylcarbodiimide
$Et_3N$ triethylamine
EtOAc ethyl acetate
EtOH ethanol
FBS fetal bovine serum
h hour HCl hydrochloride
HATU 1-[Bis(dimethylamino)methylene]-1H-1,2,3-triazolo[4,5-b]pyridinium 3-oxid hexafluorophosphate
HOBt 1-hydroxybenzotriazole
HPLC high-performance liquid chromatography
$H_2SO_4$ sulfuric acid
Hünigs base N,N-diisopropylethylamine
$IC_{50}$ concentration yielding 50% inhibition
iPrOH propan-2-ol
$K_2CO_3$ anhydrous potassium carbonate
KOH potassium hydroxide
LAH lithium aluminium hydride
LCMS liquid-chromatography electrospray mass spectroscopy
LDS lithium dodecyl sulfate
MeCN acetonitrile
MeI iodomethane
MeOH methanol
$MgSO_4$ anhydrous magnesium sulphate
min minutes
NAD(P) nicotinamide adenine dinucleotide (phosphate)
$NaHCO_3$ sodium bicarbonate
NaI sodium iodide
NaOMe sodium methoxide
$Na_2SO_4$ sodium sulfate
NBS N-bromosuccinimide
n-BuLi n-butyl lithium
n-BuOH butan-1-ol
NCS N-chlorosuccinimide
$NH_4OH$ ammonium hydroxide
NMP N-methylpyrrolidine
NMR nuclear magnetic resonance
PBS phosphate-buffered saline
$Pd(OAc)_2$ palladium(II) acetate
$Pd(PPh_3)_4$ tetrakis(triphenylphosphine)palladium(0)
$Pd_2(dba)_3$ tris(dibenzylideneacetone)dipalladium(0)
Pd—C palladium on carbon
$POCl_3$ phosphorus oxychloride
$PPh_3$ triphenylphosphine
$PPh_3O$ triphenylphosphine oxide
P/S penicillin/streptomycin
rac racemic
RBF round bottom flask
RPMI Roswell Park Memorial Institute
rt room temperature
RuPhos 2-dicyclohexylphosphino-2',6'-diisopropoxybiphenyl
sat saturated
SDS sodium dodecyl sulfate
$SnCl_2.2H_2O$ tin chloride dihydrate
SPhos 2-dicyclohexylphosphino-2',6'-dimethoxybiphenyl
TBTU 2-(1H-benzotriazol-1-yl)-1,1,3,3-tetramethyluronoium hexafluorphosphate
TC tissue culture
tBuOK potassium tert-butoxide
tBuONa sodium tert-butoxide
TGS Tris-glycine-SDS
TFA trifluoroacetic acid
THF tetrahydrofuran
TMS-$N_3$ trimethylsilyl azide
Tris tris(hydroxymethyl)aminomethane
XPhos 2-dicyclohexylphosphino-2',4',6'-triisopropylbiphenyl Experimental Procedures Starting materials and intermediates used in the synthesis of compounds described herein are commercially available, e.g. from Sigma-Aldrich, Fine Chemicals, Combi-Blocks and other vendors, or can be prepared by the methods described herein or by methods known in the art.

All commercial reagents and solvents were used without further purification. Analytical thin-layer chromatography was performed on silica gel 60 F-254 plates (Merck) and visualized under a UV lamp. Flash column chromatography was performed in a Biotage SP4MPLC or ISCO combi flash system using Merck silica gel 60 Å (40-63 mm mesh).

$^1$H NMR spectra were recorded on a Bruker DRX-400. Chemical shifts are expressed in parts per million (ppm) and referenced to the residual solvent peak. Analytical HPLC-MS was performed on an Agilent MSD mass spectrometer connected to an Agilent 1100 system with: Method acidic pH, Column ACE 3 C8 (50 mm×3.0 mm), $H_2O$ (+0.1% TFA), and MeCN were used as mobile phases at a flow rate of 1 mL/min, with a gradient time of 3.0 min; or Method basic pH, Column XTerraMSC18 (50 mm×3.0 mm), $H_2O$ (containing 10 mM NH4HCO3; pH=10), and MeCN were used as mobile phases at a flow rate of 1 mL/min, with a gradient time of 3.0 min. Preparative HPLC was performed on a Gilson HPLC system. Basic pH: column Xbridge Prep C18, 5 μM CBD (30 mm×75 mm), $H_2O$ (containing 50 mM $NH_4HCO_3$; pH=10), and MeCN were used as mobile phases at a flow rate of 45 mL/min, with a gradient time of 9 min. Acidic pH: column ACE 5 C8 (150 mm×30 mm), $H_2O$ (containing 0.1% TFA), and MeCN were used as mobile phases at a flow rate of 45 mL/min, with a gradient time of 9 min. For HPLC-MS, detection was made by UV using the 180-305 nM range and MS (ESI+). For preparative HPLC, detection was made by UV at 254 or 214 nM. Where applicable, compound names indicated in respect of the following intermediates and examples have been generated using the structure naming function of MarvinSketch (ChemAxon).

Intermediate 1: 5-{[(2,4-diamino-6-oxo-1,6-dihydropyrimidin-5-yl)carbamoyl]amino}pyridine-2-carboxylic acid

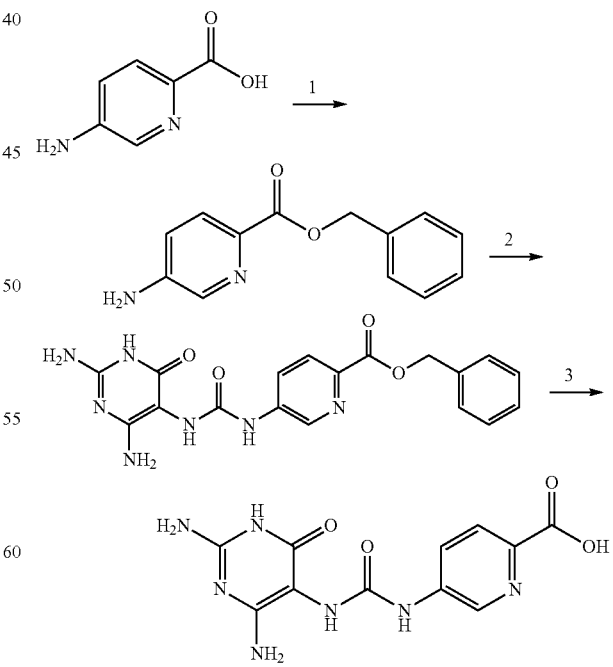

1) Benzyl bromide, $K_2CO_3$, DMF, rt; 2) $Et_3N$, 4-nitrophenyl chloroformate, THF, rt;
3) 1M NaOH, rt.

Step 1: Benzyl 5-aminopyridine-2-carboxylate. To a stirred solution of 5-aminopyridine-2-carboxylic acid (1.0 g, 7.24 mmol) in DMF (30 mL) was added K₂CO₃ (5.0 g, 36.2 mmol) followed by benzyl bromide (0.947 mL, 7.96 mmol). The reaction mixture was stirred at rt for 2 h then poured into water (300 mL), extracted with EtOAc (3×50 mL), washed with brine (50 mL), dried over magnesium sulphate. The organic solvent was removed under reduce pressure and the residue was chromatographed on silica gel (EtOAc/iHex) to generate benzyl 5-aminopyridine-2-carboxylate as solid (830 mg, 50%). LCMS [M+H]⁺ m/z 229; ¹H NMR (400 MHz, DMSO-d₆) δ ppm 7.97 (dd, J=2.5, 0.6 Hz, 1H), 7.78 (dd, J=8.5, 0.6 Hz, 1H), 7.23-7.59 (m, 5H), 6.92 (dd, J=8.7, 2.7 Hz, 1H), 6.22 (s, 2H), 5.26 (s, 2H).

Step 2: benzyl 5-{[(2,4-diamino-6-oxo-1,6-dihydropyrimidin-5-yl)carbamoyl]amino}pyridine-2-carboxylate.
benzyl 5-aminopyridine-2-carboxylate (800 mg, 3.47 mmol) and Et₃N (0.483 ml, 3.47 mmol) in dry THF (5 mL) was slowly added to a stirred solution of 4-nitrophenyl chloroformate (699 mg, 3.47 mmol) in dry THF (5 mL). The reaction was stirred for 30 min at rt. The generated pale white slurry was added to 2,5,6-triamino-3,4-dihydropyrimidin-4-one; sulfuric acid (830 mg, 3.47 mmol) in 1M NaOH (3 equiv. vs the sulfate). The reaction was stirred for 1 h and benzyl 5-{[(2,4-diamino-6-oxo-1,6-dihydropyrimidin-5-yl)carbamoyl]amino}pyridine-2-carboxylate was collected by filtration, washed with water (20 mL), ACN (10 mL) and dried to obtain pale brown solid (936 mg, 65%). LCMS [M+H]⁺ m/z 396; ¹H NMR (400 MHz, DMSO-d₆) δ ppm 10.00 (br. s., 1H), 9.24 (br. s., 1H), 8.68 (br. s., 1H), 8.13 (d, J=7.9 Hz, 1H), 8.00 (d, J=8.8 Hz, 1H), 7.29-7.51 (m, 5H), 6.88 (br. s., 1H), 6.18 (br. s., 2H), 5.95 (br. s., 2H), 5.33 (s, 2H).

Step 3: 5-{[(2,4-diamino-6-oxo-1,6-dihydropyrimidin-5-yl)carbamoyl]amino}pyridine-2-carboxylic acid. To benzyl 5-{[(2,4-diamino-6-oxo-1,6-dihydropyrimidin-5-yl)carbamoyl]amino}pyridine-2-carboxylate (934 mg, 2.36 mmol) 1M NaOH (20 mL) was added, followed by stirring at rt for 18 h. The reaction mixture was filtered and 2M HCl was added to obtain a pH to 3-4. The precipitated product was washed with water (100 mL) and EtOH (20 mL) to generate the title compound as a pale brown solid (650 mg, 91%). LCMS [M+H]⁺ m/z 306; ¹H NMR (400 MHz, DMSO-d₆) δ ppm 12.79 (br. s., 1H), 9.99 (br. s., 1H), 9.22 (br. s., 1H), 8.70 (br. s., 1H), 8.08 (d, J=6.0 Hz, 1H), 7.95 (d, J=8.5 Hz, 1H), 6.88 (br. s., 1H), 6.20 (br. s., 2H), 5.94 (br. s., 2H).

Intermediate 2: methyl (2S)-2-amino-4-[1-(2-cyanoethyl)-1H-1,2,3,4-tetrazol-5-yl]butanoate hydrochloride

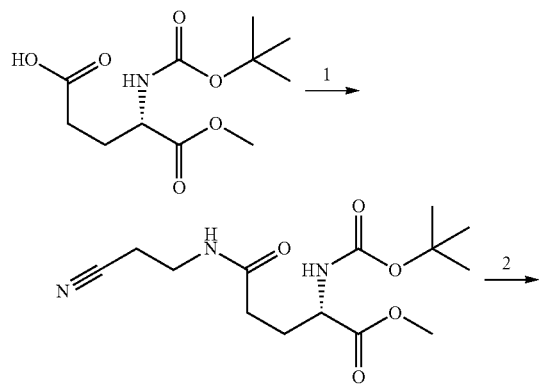

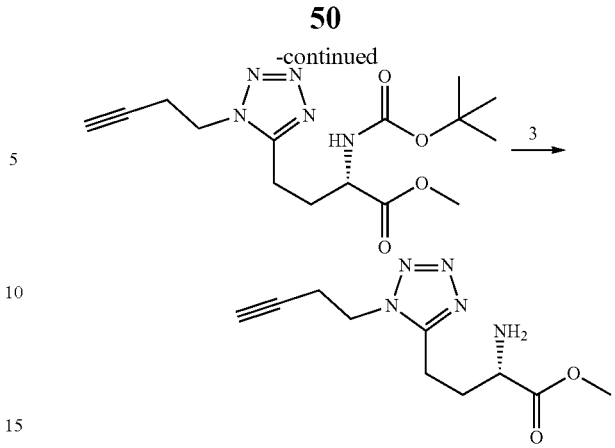

1) 3-Aminopropanenitrile, EDCl, DMAP, DCM, rt; 2) DIAD, PPh₃, TMS—N₃, ACN, 0° C.→rt; 3) 4M HCl in dioxane, EtOAc, rt.

Step 1: methyl (2S)-2-{[(tert-butoxy)carbonyl]amino}-4-[(2-cyanoethyl)carbamoyl]butanoate. (4S)-4-{[(tert-butoxy)carbonyl]amino}-5-methoxy-5-oxopentanoic acid (700 mg, 2.52 mmol) was dissolved in DCM. 3-Aminopropanenitrile (228 µl, 3.03 mmol), DMAP (1.23 g, 10.1 mmol) and EDCl (581 mg, 3.03 mmol) was then added and stirred at rt for 18 h. The reaction mixture was diluted with DCM (50 mL) and washed with 1M HCl (50 mL) and sat NaHCO₃ (50 mL). The organic phase was dried with Na₂SO₄, filtered and concentrated to generate methyl (2S)-2-{[(tert-butoxy)carbonyl]amino}-4-[(2-cyanoethyl)carbamoyl]butanoate (762 mg, 91%). LCMS [M+H]⁺ m/z 314; ¹H NMR (400 MHz, CDCl₃) δ ppm 6.86 (br. s., 1H), 5.32 (d, J=7.3 Hz, 1H), 4.23-4.38 (m, 1H), 3.76 (s, 3H), 3.48-3.58 (m, 2H), 2.65 (t, J=6.5 Hz, 2H), 2.29-2.36 (m, 2H), 2.15-2.25 (m, 1H), 1.84-1.97 (m, 1H), 1.45 (s, 9H).

Step 2: methyl (2S)-2-{[(tert-butoxy)carbonyl]amino}-4-[1-(2-cyanoethyl)-1H-1,2,3,4-tetrazol-5-yl]butanoate.
methyl (2S)-2-{[(tert-butoxy)carbonyl]amino}-4-[(2-cyanoethyl)carbamoyl]butanoate (762 mg, 2.43 mmol) and PPh₃ (1.27 g, 4.86 mmol) were dissolved in dry ACN (15 mL) and cooled to 0° C. DIAD (956 µl, 4.86 mmol) followed by TMS-N₃ (646 µl, 4.86 mmol) were added dropwise. The ice bath was removed and the reaction was stirred at rt for 18 h. 0.1 M CAN (3 ml) was added and the reaction was stirred for 10 min. The reaction mixture was then poured into sat NaHCO₃ (50 mL) and extracted with EtOAc. The organic phase was dried with Na₂SO₄, filtered and concentrated. The crude material was purified by column chromatography on silica (EtOAc/IHex) to generate methyl (2S)-2-{[(tert-butoxy)carbonyl]amino}-4-[1-(2-cyanoethyl)-1H-1,2,3,4-tetrazol-5-yl]butanoate in mixture with PPh₃O (665 mg, 81%, 1.46 g incl PPh₃O). LCMS [M+H]⁺ m/z 339; ¹H NMR (400 MHz, methanol-d₄) δ ppm 7.52-7.68 (m, 21H, PPh₃O), 4.61-4.76 (m, 2H), 4.24 (dd, J=9.2, 4.7 Hz, 1H), 3.72 (s, 3H), 3.13-3.20 (m, 2H), 3.06 (t, J=7.7 Hz, 2H), 2.33-2.47 (m, 1H), 2.07-2.25 (m, 1H), 1.44 (s, 9H).

Step 3: methyl (2S)-2-amino-4-[1-(2-cyanoethyl)-1H-1,2,3,4-tetrazol-5-yl]butanoate hydrochloride, methyl (2S)-2-{[(tert-butoxy)carbonyl]amino}-4-[1-(2-cyanoethyl)-1H-1,2,3,4-tetrazol-5-yl]butanoate containing PPh₃O (1.17 g, 1.72 mmol) was dissolved in EtOAc (10 mL) before adding 4M HCl in dioxane (6.5 mL) and stirred at rt for 20 min. The product precipitated on the RBF wall from the clear solution, and the white precipitate was washed with EtOAc to yield the pure title compound (380 mg, 80%). LCMS [M+H]⁺ m/z 239; ¹H NMR (400 MHz, DMSO-d₆) δ ppm 8.69 (br. s., 3H), 4.62-4.72 (m, 10H), 4.21 (t, J=6.6 Hz, 1H), 3.74 (s, 3H), 3.19-3.24 (m, 2H), 3.05-3.19 (m, 2H), 2.24-2.42 (m, 2H).

Intermediate 3: 5-{[(2,4-diamino-6-oxo-1,6-dihydropyrimidin-5-yl)carbamoyl]amino}-3-fluoropyridine-2-carboxylic acid

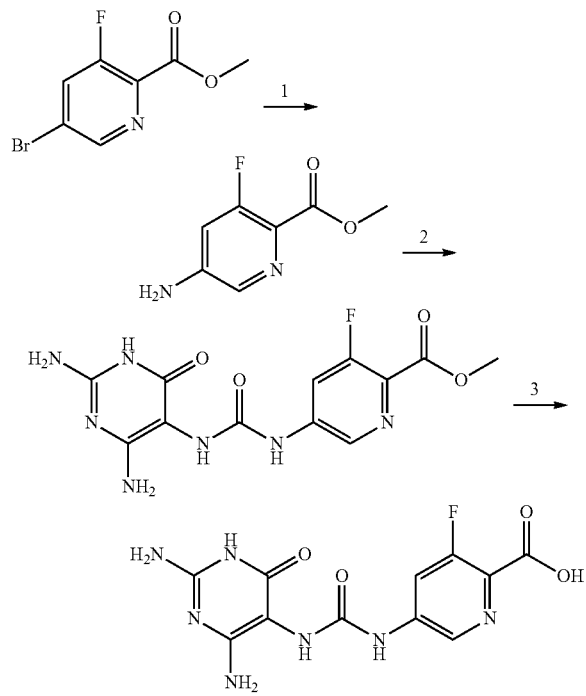

1) (i) tert-Butyl carbamate, Cs₂CO₃, Pd(OAc)₂, XPhos, dioxane, 90° C.;
(ii) TFA, DCM, rt; 2) (i) 4-nitrophenyl chloroformate, Et₃N, THF, rt;
(ii) 2,4,5-triamino-1H-pyrimidin-6-one, H₂SO₄, 1M NaOH, rt; 3) 1M NaOH.

Step 1: methyl 5-amino-3-fluoropyridine-2-carboxylate. Dry dioxane (5 mL) was added to a stirred mixture of methyl 5-bromo-3-fluoropyridine-2-carboxylate (600 mg, 2.56 mmol), tert-butyl carbamate (360 mg, 3.08 mmol) and Cs₂CO₃ (1.0 g, 3.08 mmol) and N₂ was bubbled through. A mixture of Pd(OAc)₂ (28.7 mg, 0.13 mmol) and XPhos (119 mg, 0.26 mmol) was added to the reaction mixture. N₂ was flushed through the reaction mixture before the tube was sealed and placed in a pre-heated (90° C.) block. The reaction was stirred at 90° C. for 20 h. Water (40 mL) was then added and the mixture was extracted with EtOAc (2×100 mL). The organic phase was washed with brine (40 mL) and dried over Na₂SO₄ to generate methyl 5-{[(tert-butoxy)carbonyl]amino}-3-fluoropyridine-2-carboxylate (583 mg, 80%). The crude product was then dissolved in DCM (7 mL) and TFA (3 mL) was added. The reaction was stirred at rt for 2 h, followed by solvent removal under reduced pressure. DCM (30 mL) was added to the crude product and extracted with water (3×30 mL). The aq phase was neutralized with sat NaHCO₃ and extracted with EtOAc. The organic phase was washed with brine and dried with Na₂SO₄ to furnish methyl 5-amino-3-fluoropyridine-2-carboxylate as a white solid (370 mg, 98%). LCMS [M+H]⁺ m/z 171.

Step 2: methyl 5-{[(2,4-diamino-6-oxo-1,6-dihydropyrimidin-5-yl)carbamoyl]amino}-3-fluoropyridine-2-carboxylate. A solution of methyl 5-amino-3-fluoropyridine-2-carboxylate (370 mg, 2.11 mmol) and Et₃N (295 μl, 2.11 mmol) in dry THF (4 mL) was slowly added to a stirred solution of 4-nitrophenyl chloroformate (425 mg, 2.11 mmol) in dry THF (4 mL). The reaction mixture was stirred at rt for 30 min. The pale white slurry was then added slowly to 2,5,6-triamino-3,4-dihydropyrimidin-4-one; sulfuric acid (505 mg, 2.11 mmol) in 1M NaOH (3 equiv. vs the sulfate). The reaction was stirred at rt for 1 h and the product was collected by filtration. The solid was washed with water (200 mL), ACN (20 mL) and water (100 mL), and methyl 5-{[(2,4-diamino-6-oxo-1,6-dihydropyrimidin-5-yl)carbamoyl]amino}-3-fluoropyridine-2-carboxylate was dried in a vacuum oven to generate the title compound as solid (165 mg, 18%). LCMS [M+H]⁺ m/z 338.

Step 3: 5-{[(2,4-diamino-6-oxo-1,6-dihydropyrimidin-5-yl)carbamoyl]amino}-3-fluoropyridine-2-carboxylic acid. To methyl 5-{[(2,4-diamino-6-oxo-1,6-dihydropyrimidin-5-yl)carbamoyl]amino}-3-fluoropyridine-2-carboxylate (165 mg, 0.49 mmol) was added 1M NaOH (1.47 mL) and the reaction mixture was stirred at rt for 15 min before 2M HCl was added to obtain a pH of 8. The precipitated by-product was filtered and washed with water (0.5 mL). Additional 2M HCl was added to the filtrate to obtain a pH of 4 and the precipitated product was washed with water (1 mL) and dried to obtain the title compound (45 mg, 24%). LCMS [M+H]⁺ m/z 324; ¹H NMR (400 MHz, DMSO-d₆) δ ppm 13.04 (br. s., 1H), 10.16 (br. s., 1H), 9.57 (br. s., 1H), 8.45 (br. s., 1H), 8.05 (d, J=13.0 Hz, 1H), 7.02 (br. s., 1H), 6.31 (br. s., 2H), 6.08 (br. s., 2H).

Intermediate 4; 1,5-diethyl (2S)-2-[(5-amino-3-chloropyridin-2-yl)formamido]pentanedioate

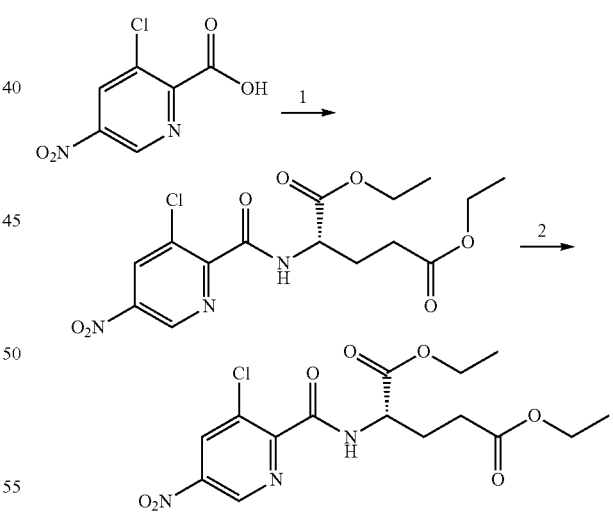

1) 1,5-Diethyl (2S)-2-aminopentanedioate•HCl, TBTU, Et₃N, THF, rt;
2) SnCl₂•2H₂O, EtOH, 90° C.

Step 1: 1,5-diethyl (2S)-2-[(3-chloro-5-nitropyridin-2-yl)formamido]pentanedioate. 3-chloro-5-nitropyridine-2-carboxylic acid (80 mg, 0.40 mmol), Et₃N (88 mg, 0.87 mmol) and TBTU (191 mg, 0.59 mmol) were dissolved in THF (4 mL). The reaction mixture was stirred at rt for 10 min. 1,5-Diethyl (2S)-2-aminopentanedioate·HCl (96 mg, 0.47 mmol) was added and stirring was continued overnight. After completion of the reaction, the volatiles were removed and the residue was diluted with water and extracted with DCM (3×20 mL). The combined organic phases were dried over Na$_2$SO$_4$ and evaporated to offer the crude product which was used without purification in the next step. Yield 147 mg (94%). LCMS [M+H]$^+$ m/z 388.

Step 2: 1,5-diethyl (2S)-2-[(5-amino-3-chloropyridin-2-yl)formamido]pentanedioate. To a solution of 1,5-diethyl (2S)-2-[(3-chloro-5-nitropyridin-2-yl)formamido]pentanedioate (147 mg, 0.38 mmol) in EtOH (10 mL) was added SnCl$_2$.2H$_2$O (507 mg, 2.3 mmol). The reaction mixture heated to 90° C. for 1 h. After completion, the mixture was cooled to rt and the volatiles were removed. The residue was then diluted with water (10 mL) and DCM (20 mL). Sat NaHCO$_3$ was added until the solution turned basic (pH 8-9). The precipitate was filtered and the layers were separated. The aq layer was further extracted with DCM (2×20 mL). The combined organic layer was washed with brine, dried (Na$_2$SO$_4$) and concentrated under reduced pressure to provide crude product which was purified by flash column chromatography (silica gel, 5% MeOH in DCM) to offer the title intermediate as a white solid. Yield 109 mg (81%). LCMS [M+H]$^+$ m/z 358.

Intermediate 5: 1,5-Diethyl (2S)-2-[(5-amino-6-ethenylpyridin-2-yl)formamido]pentanedioate for an additional h. The mixture was then diluted with water and EtOAc (10 mL). The organic layer was discarded and the aq layer was concentrated to offer the sodium salt of 5-amino-6-ethenylpyridine-2-carboxylic acid, which was used in the next step without further purification. Yield: 60 mg (81%). LCMS [M+H]$^+$ m/z 165.

Step 2: 1,5-diethyl (2S)-2-[(5-amino-6-ethenylpyridin-2-yl)formamido]pentanedioate. 5-Amino-6-ethenylpyridine-2-carboxylic acid (60 mg, 0.36 mmol), Et$_3$N (111 mg, 1.1 mmol) and TBTU (180 mg, 0.55 mmol) were dissolved in THF (4 mL). The reaction mixture was stirred at rt for 10 min. 1,5-Diethyl (2S)-2-aminopentanedioate·HCl (82 mg, 0.40 mmol) was added and stirring was continued overnight. After completion of the reaction, the volatiles were removed and the residue was diluted with water and extracted with DCM (3×20 mL). The combined organic phase was washed with aq NaHCO$_3$, brine, dried over Na$_2$SO$_4$ and evaporated to offer the crude product, which was purified by flash column chromatography (silica gel, 5% MeOH in DCM) to give pure compound. Yield 103 mg (81%). LCMS [M+H]$^+$ m/z 350.

Intermediate 6: 1,5-Diethyl (2S)-2-[(5-amino-3-methylpyridin-2-yl)formamido]pentanedioate

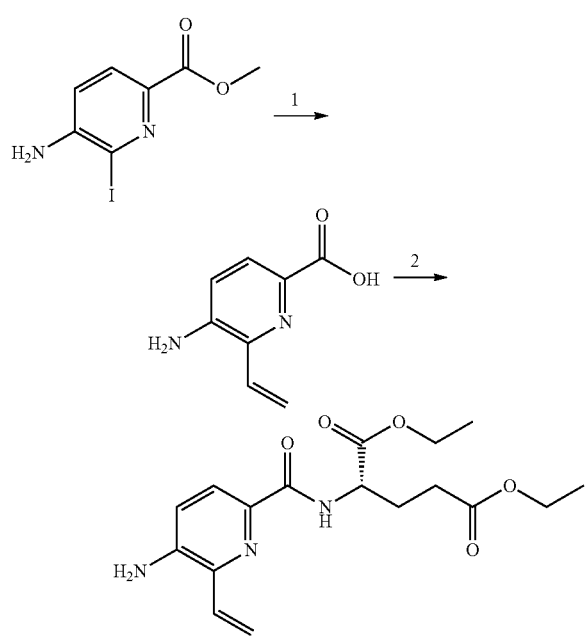

1) (i) Ethenylboronic acid, Pd(PPh$_3$)$_4$, Na$_2$CO$_3$, dioxane:water, 90° C.; (ii) 1N NaOH; 2) 1,5-Diethyl (2S)-2-aminopentanedioate·HCl, TBTU, Et$_3$N, THF, rt.

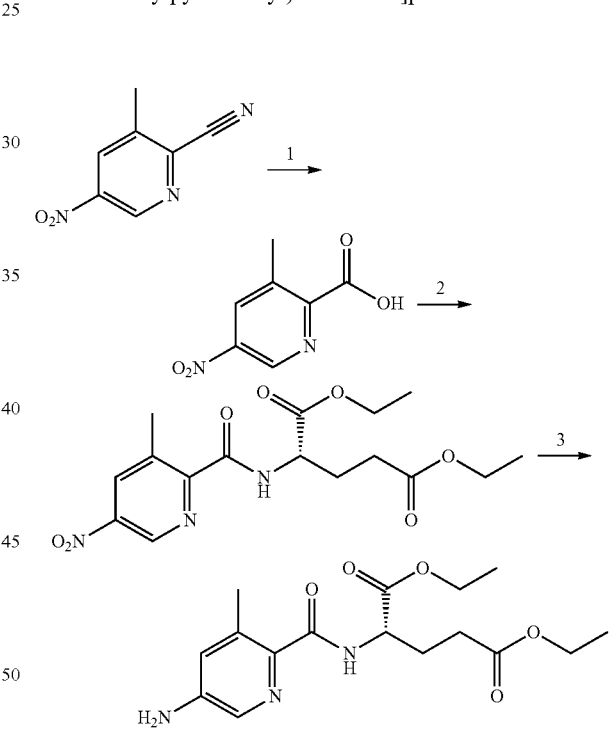

1) (i) EtOH, cat. H$_2$SO$_4$, 160° C., microwave; (ii) 1N NaOH; 2) 1,5-Diethyl (2S)-2-aminopentanedioate·HCl, TBTU, Et$_3$N, THF, rt; 3) SnCl$_2$·H$_2$O, EtOH, 90° C.

Step 1: 5-amino-6-ethenylpyridine-2-carboxylic acid. To a solution of methyl 5-amino-6-iodopyridine-2-carboxylate (125 mg, 0.45 mmol) and ethenylboronic acid (48 mg, 0.67 mmol) in dioxane:water (2:1 mL) was added Na$_2$CO$_3$ (134 mg, 1.4 mmol). The mixture was purged with N$_2$ for 15 min, after which Pd(PPh$_3$)$_4$ (52 mg, 0.05 mmol) was added and the mixture was stirred at 90° C. for 4 h. The reaction was monitored by LCMS and after the complete consumption of aryl iodide heating was discontinued and the reaction mixture was cooled to rt. In the same reaction vial 1N NaOH (1.34 mL, 1.4 mmol) was added and stirring continued at rt Step 1: 3-methyl-5-nitropyridine-2-carboxylic acid. In a 20 mL microwave vial, 3-methyl-5-nitropyridine-2-carbonitrile (200 mg, 1.2 mmol) was dissolved in EtOH (8 mL) and conc. H$_2$SO$_4$ (2 mL). The vial was sealed and heated to 160° C. in a microwave for 30 min. After completion, the reaction mixture was cooled to rt and concentrated to dryness. The obtained residue was dissolved in THF and 1N NaOH (7.3 mL) was added slowly. The resulting mixture was stirred at rt for an additional h. The mixture was then diluted with water and acidified to pH 4-5 using 1N HCl and then extracted with DCM (3×30 mL). The combined DCM layers were washed with brine (10 mL), dried (Na₂SO₄), and concentrated to provide the crude product which was used in the next step without purification. Yield: 110 mg (51%). LCMS [M+H]⁺ m/z 183.

Step 2: 1,5-diethyl (2S)-2-[(3-methyl-5-nitropyridin-2-yl)formamido]pentanedioate. 3-Methyl-5-nitropyridine-2-carboxylic acid (110 mg, 0.88 mmol), Et₃N (183 mg, 1.8 mmol) and TBTU (295 mg, 0.91 mmol) were dissolved in THF (4 mL). The reaction mixture was stirred at rt for 10 min. 1,5-Diethyl (2S)-2-aminopentanedioate-HCl (217 mg, 0.91 mmol) was added and stirring was continued overnight. After completion of the reaction, the volatiles were removed and the residue was diluted with water and extracted with DCM (3×20 mL). The combined organic phases were dried over Na₂SO₄ and evaporated to offer the crude compound which was used without purification in the next step. Yield: 190 mg (86%). LCMS [M+H]⁺ m/z 368.

Step 3: 1,5-diethyl (2S)-2-[(5-amino-3-methylpyridin-2-yl)formamido]pentanedioate. SnCl₂.2H₂O (701 mg, 3.1 mmol) was added to a solution of 1,5-diethyl (2S)-2-[(3-methyl-5-nitropyridin-2-yl)formamido]pentanedioate (190 mg, 0.52 mmol) in EtOH (10 mL). The reaction mixture was heated at 90° C. for 1 h. After completion, the mixture was cooled to rt and the volatiles were removed. The residue was then diluted with water (10 mL) and DCM (20 mL). Sat NaHCO₃ was added until the solution turned basic (pH 8-9). The precipitate was filtered and the layers were separated. The aq layer was further extracted with DCM twice. The combined organic layers were washed with brine, dried (Na₂SO₄) and concentrated to provide the crude product, which was purified by flash column chromatography (silica gel, 5% MeOH in DCM) to offer the pure title compound as a white solid. Yield 123 mg (79%). LCMS [M+H]⁺ m/z 338.

Intermediate 7; 1,5-Diethyl (2S)-2-[(5-amino-6-phenoxypyridin-2-yl)formamido]pentanedioate

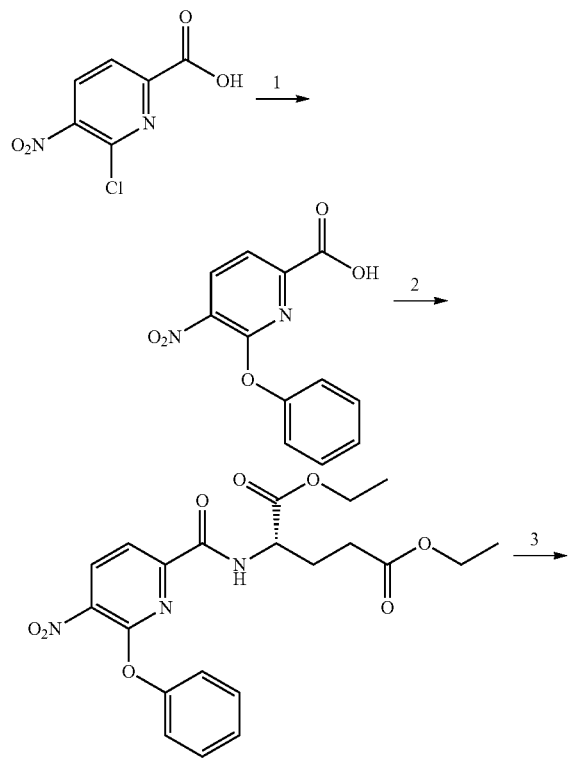

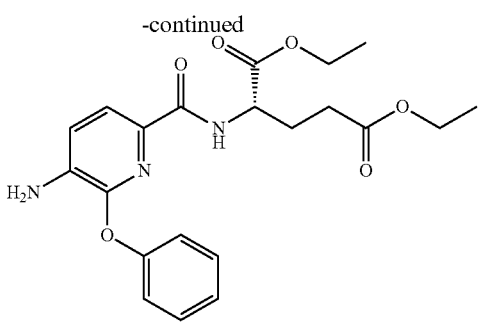

1) Phenol, Cs₂CO₃, DMSO, rt; 2) 1,5-Diethyl (2S)-2-aminopentanedioate•HCl, TBTU, Et₃N, THF, rt; 3) SnCl₂•2H₂O, EtOH, 90° C.

Step 1: 5-nitro-6-phenoxypyridine-2-carboxylic acid. In a reaction tube 6-chloro-5-nitropyridine-2-carboxylic acid (203 mg, 1.0 mmol), phenol (113 mg, 1.2 mmol) and dry powdered Cs₂CO₃ (1,042 mg, 3.2 mmol) were mixed in DMSO (2 mL) and the resulting mixture was stirred at rt for 12 h. The reaction was monitored by LCMS and after completion it was diluted with water (20 mL), sat NaHCO₃ (5 mL) and EtOAc (25 mL). The organic layer was separated and discarded. The aq layer was acidified to pH 4-5 using 1N HCl and then extracted with DCM (3×30 mL). The combined DCM layers were washed with brine (10 mL), dried (Na₂SO₄), and concentrated to provide the crude product which was used in the next step without purification. Yield: 230 mg (88%). LCMS [M+H]⁺ m/z 261.

Step 2: 1,5-diethyl (2S)-2-[(5-nitro-6-phenoxypyridin-2-yl)formamido]pentanedioate. 5-Nitro-6-phenoxypyridine-2-carboxylic acid (230 mg, 0.88 mmol), Et₃N (268 mg, 2.6 mmol) and TBTU (432 mg, 1.3 mmol) were dissolved in THF (4 mL). The reaction mixture was stirred at rt for 10 min. 1,5-Diethyl (2S)-2-aminopentanedioate-HCl (317 mg, 1.3 mmol) was added and stirring was continued overnight. After completion of the reaction, the volatiles were removed and the residue was diluted with water and extracted with DCM (3×30 mL). The combined organic phases were dried over Na₂SO₄ and evaporated to offer the crude product, which was used without purification in the next step. Yield: 316 mg (80%). LCMS [M+H]⁺ m/z 446.

Step 3: 1,5-diethyl (2S)-2-[(5-amino-6-phenoxypyridin-2-yl)formamido]pentanedioate. SnCl₂.2H₂O (0.948, 4.3 mmol) was added to a solution of 1,5-diethyl (2S)-2-[(5-nitro-6-phenoxypyridin-2-yl)formamido]pentanedioate (316 mg, 0.71 mmol) in EtOH (10 mL). The reaction mixture was heated at 90° C. for 1 h. After completion, the mixture was cooled to rt and the volatiles were removed. The residue was then diluted with water (10 mL) and DCM (20 mL). Sat NaHCO₃ was added until the solution turned basic (pH 8-9). The precipitate was filtered and the layers were separated. The aq layer was further extracted with DCM twice. The combined organic layers were washed with brine, dried (Na₂SO₄) and concentrated to provide the crude product, which was purified by flash column chromatography (silica gel, 5% MeOH in DCM) to offer the pure title compound as white solid. Yield 210 mg (71%). LCMS [M+H]⁺ m/z 416.

Intermediate 8: 1,5-Diethyl (2S)-2-[(5-amino-6-phenylpyridin-2-yl)formamido]pentanedioate

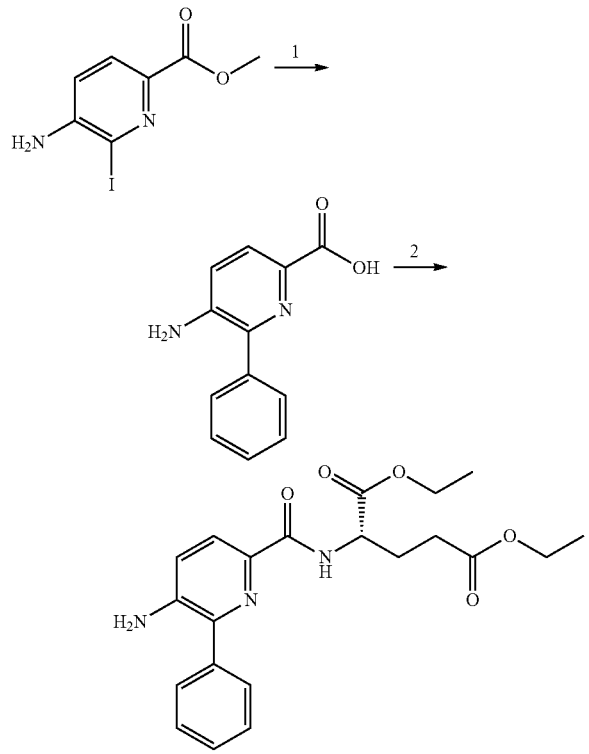

1) (i) Phenylboronic acid, Pd(PPh₃)₄, Na₂CO₃, dioxane:water, 90° C.;
(ii) 1N NaOH; 2) 1,5-Diethyl (2S)-2-aminopentanedioate·HCl, TBTU, Et₃N, THF, rt.

Step 1: 5-amino-6-phenylpyridine-2-carboxylic acid. To a solution of methyl 5-amino-6-iodopyridine-2-carboxylate (125 mg, 0.45 mmol) and phenylboronic acid (82 mg, 0.674 mmol) in dioxane:water (2:1 mL) was added Na₂CO₃ (134 mg, 1.35 mmol). The mixture was purged with N₂ for 15 min, after which Pd(PPh₃)₄ (52 mg, 0.045 mmol) was added and the mixture was stirred at 90° C. for 4 h. The reaction was monitored by LCMS and after the complete consumption of aryl iodide the reaction mixture was allowed cool to rt. In the same reaction vial 1N NaOH (1.34 mL, 1.35 mmol) was added and stirring continued for an additional h. The mixture was then diluted with water and EtOAc (10 mL). The organic layer was discarded and the aq layer was concentrated to offer the crude product as sodium salt, which was used in the next step without further purification. Yield: 72% (69 mg). LCMS [M+H]⁺ m/z 215.

Step 2: 1,5-diethyl (2S)-2-[(5-amino-6-phenylpyridin-2-yl)formamido]pentanedioate. 5-Amino-6-phenylpyridine-2-carboxylic acid (69 mg, 0.32 mmol), triethylamine (98 mg, 0.97 mmol) and 2-(1H-benzotriazole-1-yl)-1,1,3,3-tetramethylammonium tetrafluoroborate (TBTU) (156 mg, 0.48 mmol) were dissolved in THF (4 mL). The reaction mixture was stirred at rt for 10 min. 1,5-Diethyl (2S)-2-aminopentanedioate·HCl (98 mg, 0.48 mmol) was added and stirring was continued overnight. After completion of the reaction, the volatiles were removed and the residue was diluted with water and extracted with DCM (3×20 mL). The combined organic phases were dried over Na₂SO₄ and evaporated to offer the crude product, which was purified by flash column chromatography (silica gel, 5% MeOH in DCM) to offer the pure title compound. Yield 85% (110 mg). LCMS [M+H]⁺ m/z 400.

Intermediate 9: 5-[2-(2,4-diamino-6-oxo-1,6-dihydropyrimidin-5-yl)acetamido]pyridine-2-carboxylic acid

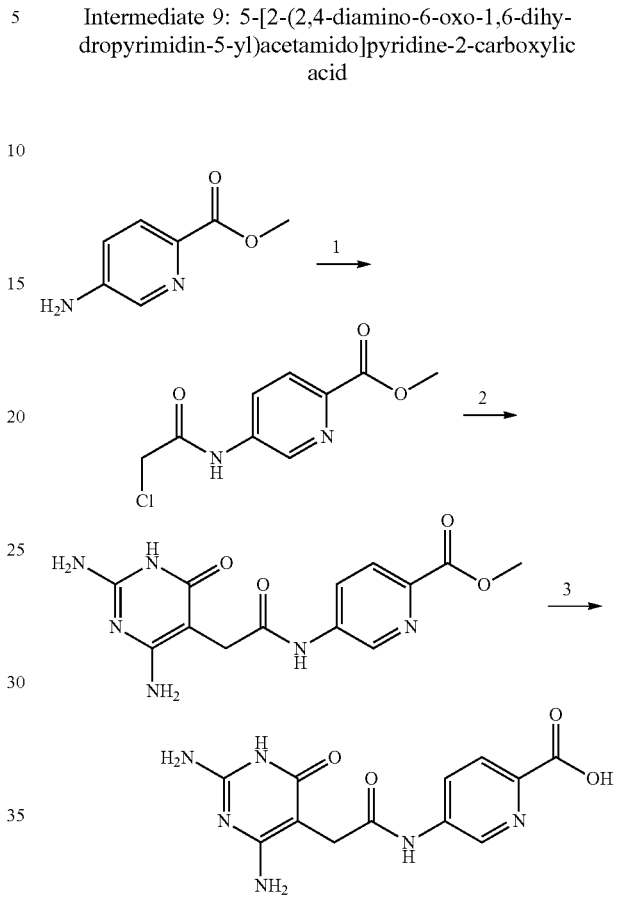

1) 2-Chloroacetyl chloride, Na₂CO₃, THF, water, rt; 2) 2,4-Diamino-1H-pyrimidin-6-one, NaHCO₃, NaI, DMF, rt; 3) (i) 5M NaOH, water, rt; (ii) 1M HCl.

Step 1: methyl 5-(2-chloroacetamido)pyridine-2-carboxylate. 2-Chloroacetyl chloride (0.850 mL, 10.6 mmol) was added to a vigorously stirred mixture of methyl 5-aminopyridine-2-carboxylate (1.00 g, 6.57 mmol), Na₂CO₃ (1.39 g, 13.1 mmol), THF (10 mL) and water (10 mL) at rt. The reaction was stirred for 30 min. The product was then collected by filtration, washed with water and dried under reduced pressure. This gave 550 mg (37%) of the desired product. LCMS [M+H]⁺ m/z 229.

Step 2: methyl 5-[2-(2,4-diamino-6-oxo-1,6-dihydropyrimidin-5-yl)acetamido]pyridine-2-carboxylate. A mixture of methyl 5-(2-chloroacetamido)pyridine-2-carboxylate (530 mg, 2.32 mmol), 2,6-diamino-3,4-dihydropyrimidin-4-one (321 mg, 2.55 mmol), NaHCO₃ (214 mg, 2.55 mmol), NaI (347 mg, 2.32 mmol) and DMF (5 mL) was stirred in a sealed tube for 5 days at rt. The product was collected by filtration and washed with MeCN. This gave 1.60 g of crude product which was used in the next step without further purifications. LCMS [M+H]⁺ m/z 319.

Step 3: 5-[2-(2,4-diamino-6-oxo-1,6-dihydropyrimidin-5-yl)acetamido]pyridine-2-carboxylic acid. Crude methyl 5-[2-(2,4-diamino-6-oxo-1,6-dihydropyrimidin-5-yl)acetamido]pyridine-2-carboxylate (1.50 g) was added to water (2 mL) and 5M NaOH (2 mL) and the reaction mixture was stirred at rt for 20 min. Water (1 mL) was added and the solution was filtered. 1M HCl was added to the filtrate until pH 3 was reached. The product was collected by filtration, washed with water (2 mL) and concentrated under reduced pressure. This gave 655 mg (99% over two steps) of the title compound. LCMS [M+H]⁺ m/z 305.

Intermediate 10: 1,5-Diethyl (2S)-2-[(5-amino-3-fluoropyridin-2-yl)formamido]pentanedioate

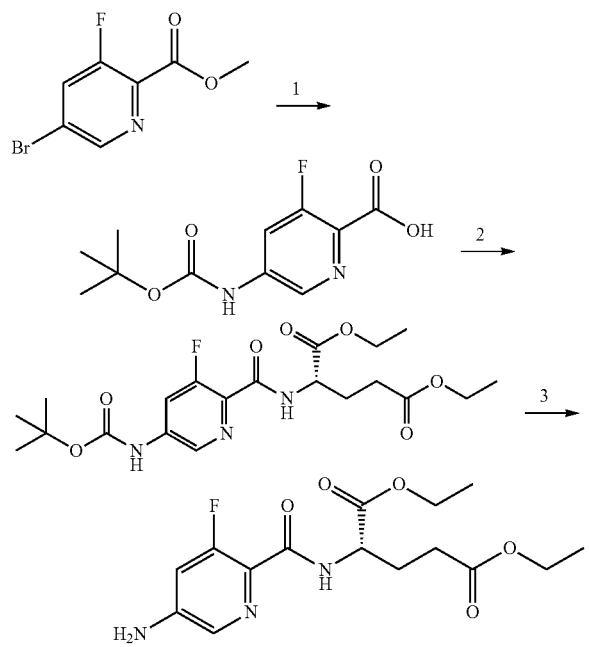

1) (i) tert-Butyl carbamate, Pd(OAc)₂, XPhos, Cs₂CO₃, dioxane, 90° C.; (ii) 1N NaOH;
2) 1,5-diethyl (2S)-2-aminopentanedioate•HCl, TBTU, Et₃N, THF, rt; 3) DCM, TFA, rt.

Step 1: 5-{[(tert-butoxy)carbonyl]amino}-3-fluoropyridine-2-carboxylic acid. In a sealed tube under N₂ atmosphere methyl 5-bromo-3-fluoropyridine-2-carboxylate (232 mg, 1.0 mmol), tert-butyl carbamate (139 mg, 1.2 mmol), dry powdered Cs₂CO₃ (387 mg, 1.2 mmol), XPhos (46 mg, 0.10 mmol), and Pd(OAc)₂ (11 mg, 0.05 mmol) were combined. Dry dioxane (4 mL) was then added and the mixture was heated to 90° C. for 3 h. The reaction was monitored by LCMS and after the complete consumption of aryl bromide the reaction mixture was allowed to cool to rt. To the same reaction vial 1N NaOH (3 mL) was added and stirring was continued for an additional h. The reaction mixture was then diluted with water and EtOAc (25 mL). The organic layer was separated and discarded. The aq layer was acidified to pH 4-5 using 1N HCl and then extracted with DCM (3×30 mL). The combined organic layers were washed with brine (10 mL), dried (Na₂SO₄), and concentrated to provide the crude product, which was used in the next step without purification. Yield 220 mg (86%). LCMS [M+H]⁺ m/z 257.

Step 2: 1,5-diethyl (2S)-2-[(5-{[(tert-butoxy)carbonyl]amino}-3-fluoropyridin-2-yl)formamido]pentanedioate. 5-{[(tert-Butoxy)carbonyl]amino}-3-fluoropyridine-2-carboxylic acid (220 mg, 0.86 mmol), Et₃N (191 mg, 1.9 mmol) and TBTU (420 mg, 1.3 mmol) were dissolved in THF (4 mL). The reaction mixture was stirred at rt for 10 min. 1.5-Diethyl (2S)-2-aminopentanedioate-HCl (309 mg, 1.3 mmol) was added and stirring was continued overnight. After completion of the reaction, volatiles were removed and the residue was diluted with water (20 mL), aq NaHCO₃ (5 mL) and extracted with DCM (3×30 mL). The combined organic phases were dried over Na₂SO₄ and evaporated to offer the crude product, which was used without purification in the next step. Yield 331 mg (92%). LCMS [M+H]⁺ m/z 442.

Step 3: 1,5-diethyl (2S)-2-[(5-amino-3-fluoropyridin-2-yl)formamido]pentanedioate. The crude residue of 1,5-diethyl (2S)-2-[(5-{[(tert-butoxy)carbonyl]amino}-3-fluoropyridin-2-yl)formamido]pentanedioate (331 mg, 0.75 mmol) was dissolved in 1:1 DCM:TFA (5 mL) and stirred at rt for 1 h. The resulting mixture was concentrated under reduced pressure and the residue was dissolved in water (20 mL), sat aq NaHCO₃ (until pH 8-9) and DCM (40 mL). The layers were separated and the organic layer was washed with brine (10 mL), dried (Na₂SO₄), concentrated, and purified by silica gel chromatography (5% MeOH in DCM) to provide pure 1,5-diethyl (2S)-2-[(5-amino-3-fluoropyridin-2-yl)formamido]pentanedioate as a white solid. Yield 213 mg (83%). LCMS [M+H]⁺ m/z 342.

Intermediate 11: 1,6-dimethyl (2S)-2-aminohexanedioate hydrochloride

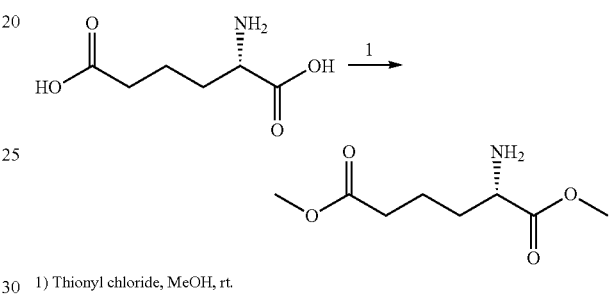

1) Thionyl chloride, MeOH, rt.

Step 1: to a solution of ((2S)-2-aminohexanedioic acid (300 mg, 1.86 mmol) in MeOH (10 mL) at 0° C. was added thionyl chloride (543 μl, 7.45 mmol). The reaction mixture was stirred at rt for 3 h, and concentrated to dryness under reduced pressure to generate the title compound as the HCl salt. LCMS [M+H]⁺ 190.

Intermediate 12; methyl (2S)-2-amino-4-[(benzenesulfonyl)carbamoyl]butanoate hydrochloride

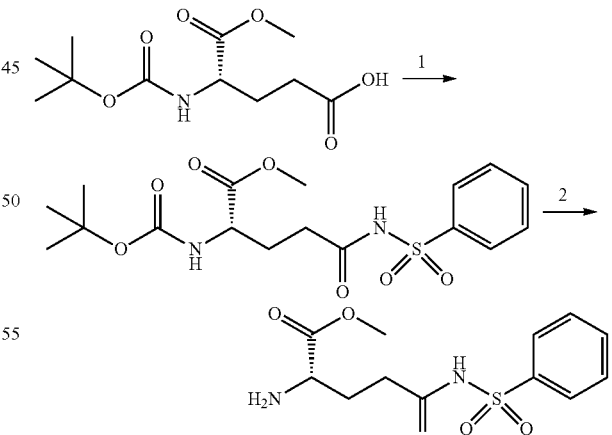

1) Benzenesulfonamide, EDCl, DMAP, DCM, rt; 2) 4M HCl in dioxane, EtOAc, rt.

Step 1: methyl (2S)-4-[(benzenesulfonyl)carbamoyl]-2-{[(tert-butoxy)carbonyl]amino}butanoate. (4S)-4-{[(tert-butoxy)carbonyl]amino}-5-methoxy-5-oxopentanoic acid (1.00 g, 3.83 mmol) was dissolved in DCM (50 mL), benzenesulfonamide (0.72 g, 4.60 mmol), EDCl (0.88 g, 4.60 mmol) and DMAP (1.87 g, 15.3 mmol) were added and the reaction mixture was stirred at rt for 24 h. The reaction mixture was washed with 1M aq HCl, dried with Na$_2$SO$_4$, filtered and concentrated. The crude material was purified by column chromatography on silica gel (hexane:EtOAc:AcOH 59:40:1) to afford methyl (2S)-5-(benzenesulfonamido)-2-(tert-butoxycarbonylamino)-5-oxo-pentanoate (1.00 g, 65%). LCMS [M+H]$^+$ m/z 401; $^1$H NMR (400 MHz, CDCl$_3$) δ ppm 9.92 (Br. s, 1H), 8.03 (d, J=13.0 Hz, 2H), 7.42-7.65 (m, 3H), 5.25-5.35 (m, 1H), 4.12-4.22 (m, 1H), 3.62 (s, 3H), 2.28-2.38 (m, 2H), 2.02-2.11 (m, 1H), 1.75-1.87 (m, 1H), 1.40 (s, 9H).

Step 2: methyl (2S)-2-amino-4-[(benzenesulfonyl)carbamoyl]butanoate hydrochloride. To methyl (2S)-4-[(benzenesulfonyl)carbamoyl]-2-{[(tert-butoxy)carbonyl]amino}butanoate (300 mg, 0.75 mmol) was added EtOAc (5 mL) and 4M HCl in dioxane (3.56 mL) and stirred for 15 min. After removal of the solvent under reduced pressure the title compound was isolated as the HCl salt (170 mg, 67%). LCMS [M+H]$^+$ m/z 301.

Intermediate 13: 1,5-dimethyl (2R)-2-[(4S)-4-amino-5-methoxy-5-oxopentanamido]pentanedioate hydrochloride

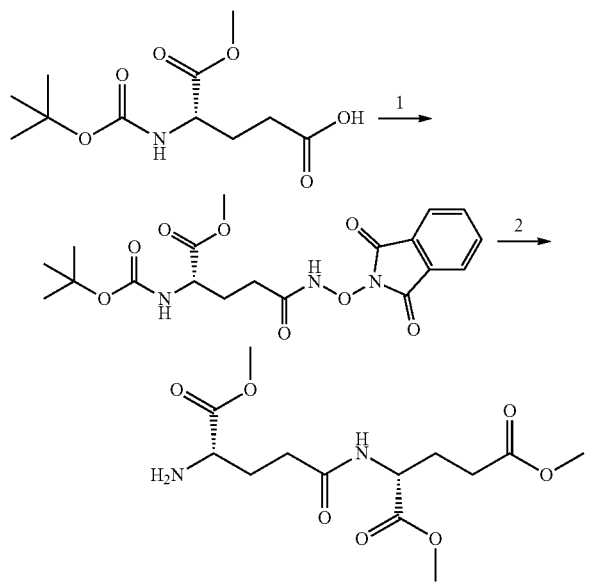

1) N-Hydroxyphthalimide, EDCl, DMAP, DCM, rt; 2) (i) Dimethyl (2R)-2-aminopentanedioate•HCl, DMAP, DCM, rt; (ii) 4M HCl in dioxane, EtOAc, rt.

Step 1: methyl (2S)-2-{[(tert-butoxy)carbonyl]amino}-4-{[(1,3-dioxo-2,3-dihydro-1H-isoindol-2-yl)oxy]carbamoyl}butanoate. (4S)-4-{[(tert-Butoxy)carbonyl]amino}-5-methoxy-5-oxopentanoic acid (2.00 g, 7.66 mmol), N-hydroxyphthalimide (1.50 g, 9.20 mmol) and EDCl (1.76 g, 9.20 mmol) were mixed in DCM (30 ml) and DMAP (3.74 g, 30.7 mmol) was added, and the reaction mixture was stirred at rt for 4 h. The reaction mixture was diluted with DCM and washed with 1M aq HCl and sat NaHCO$_3$. The crude material was purified by column chromatography on silica gel (hexanes:EtOAc 90:10 to 60:40) to afford the pure title compound (1.79 g, 58%). LCMS [M+H]$^+$ m/z 407; $^1$H NMR (400 MHz, CDCl$_3$) δ ppm 7.79-7.86 (m, 2H), 7.71-7.77 (m, 2H), 5.27 (br. s, 1H), 4.37 (s, 1H), 4.25 (s, 3H), 3.14-3.34 (m, 2H), 2.22-2.33 (m, 1H), 2.02-2.11 (m, 1H), 1.40 (s, 9H).

Step 2: 1,5-dimethyl (2R)-2-[(4S)-4-amino-5-methoxy-5-oxopentanamido]pentanedioate hydrochloride. DMAP (87 mg, 0.68 mmol) was added to a stirred solution of dimethyl (2R)-2-aminopentanedioate•HCl (143 mg, 0.68 mmol) and methyl (2S)-2-{[(tert-butoxy)carbonyl]amino}-4-{[(1,3-dioxo-2,3-dihydro-1H-isoindol-2-yl)oxy]carbamoyl}butanoate (250 mg, 0.62 mmol) in DCM (5 mL) at rt under N$_2$ and stirred at rt for 18 h. Then the reaction mixture was neutralized by 5% AcOH solution and extracted with DCM. The organic layer was separated, successively washed with water and brine, and dried over anhydrous MgSO$_4$. The crude product was purified by column chromatography (EtOAc:hexane 1:1) to furnish the boc protected intermediate (179 mg, 70%). LCMS [M+H]$^+$ m/z 419; $^1$H NMR (400 MHz, CDCl$_3$) δ ppm 7.11 (d, J=6.6 Hz, 1H), 5.34 (br. s., 1H), 4.61 (td, J=7.9, 5.4 Hz, 1H), 4.43 (br. s., 1H), 3.76 (s, 6H), 3.68 (s, 3H), 2.31-2.57 (m, 4H), 2.14-2.28 (m, 2H), 1.98-2.10 (m, 1H), 1.84-1.98 (m, 1H), 1.45 (s, 9H). Then HCl (4M in dioxane, 3.0 mL) was added to the BOC-protected amine and the mixture was stirred at rt for 2 h. After solvent removal the title compound was afforded as the HCl salt (83 mg, 55%). LCMS [M+H]$^+$ m/z 319.

Intermediate 14; 1,5-diethyl (2S)-2-[(4S)-4-amino-5-methoxy-5-oxopentanamido]pentanedioate hydrochloride

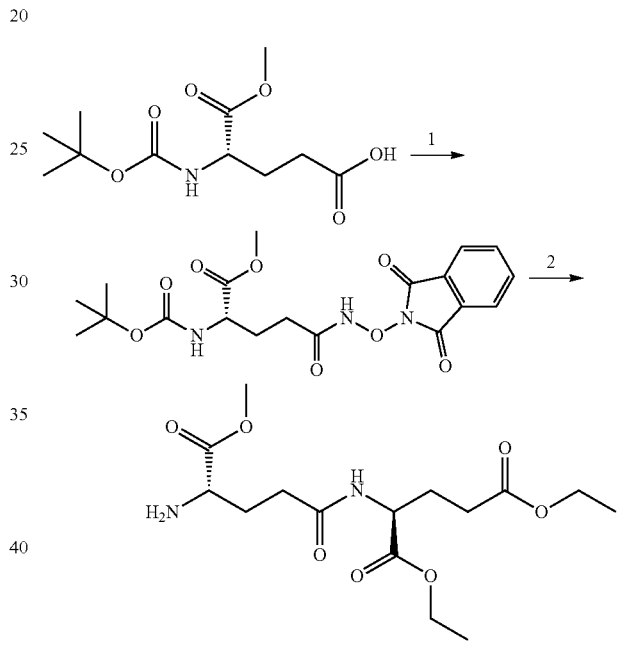

1) N-Hydroxyphthalimide, EDCl, DMAP, DCM, rt; 2) (i) Dimethyl (2S)-2-aminopentanedioate•HCl, DMAP, DCM, rt; (ii) 4M HCl in dioxane, EtOAc, rt.

Prepared according to the same procedure as described for 1,5-dimethyl (2R)-2-[(4S)-4-amino-5-methoxy-5-oxopentanamido]pentanedioate hydrochloride (Intermediate 13) from 1,3-dioxo-2,3-dihydro-1H-isoindol-2-yl 1-methyl (2S)-2-{[(tert-butoxy)carbonyl]amino}pentanedioate (437 mg, 1.08 mmol) and 1,5-diethyl (2S)-2-aminopentanedioate hydrochloride (283 mg, 1.18 mmol) to generate the title compound as the HCl salt (295 mg, 72%, 2 steps). LCMS [M+H]$^+$ m/z 319

Intermediate 15: 5-[2-(2,4-diamino-6-oxo-1,6-dihydropyrimidin-5-yl)acetamido]-3-fluoropyridine-2-carboxylic acid

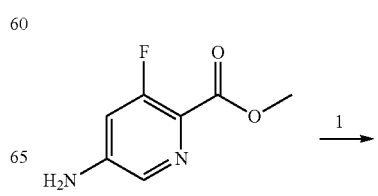

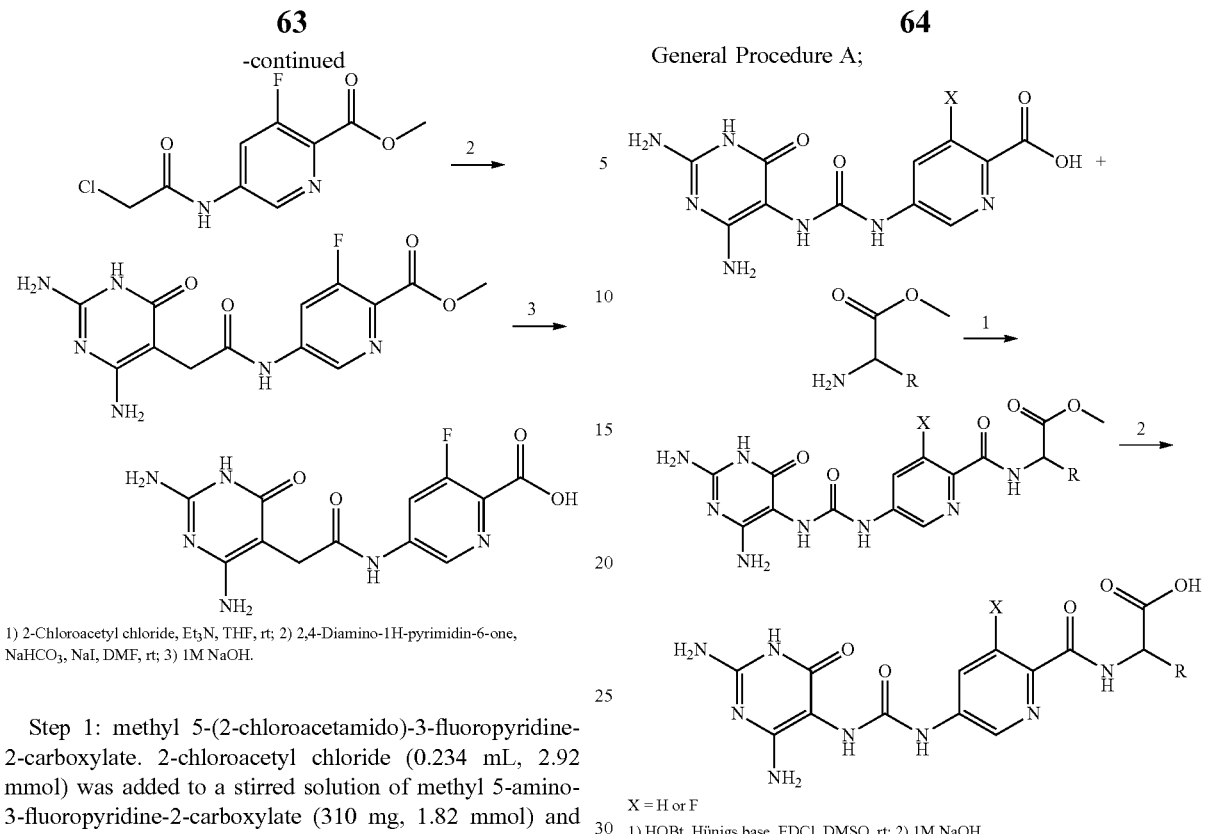

1) 2-Chloroacetyl chloride, Et₃N, THF, rt; 2) 2,4-Diamino-1H-pyrimidin-6-one, NaHCO₃, NaI, DMF, rt; 3) 1M NaOH.

Step 1: methyl 5-(2-chloroacetamido)-3-fluoropyridine-2-carboxylate. 2-chloroacetyl chloride (0.234 mL, 2.92 mmol) was added to a stirred solution of methyl 5-amino-3-fluoropyridine-2-carboxylate (310 mg, 1.82 mmol) and Et₃N (0.507 mL, 3.64 mmol) in THF (15 mL) at rt. The reaction was stirred for 20 min and water (5 mL) was added. The mixture was stirred for 5 min and EtOAc (50 mL) was added. The organic solvents was washed with sat Na₂CO₃, dried over Na₂SO₄ and removed in a rotavapor to give the desired compound (449 mg, 100%). LCMS [M+H]⁺ m/z 247.

Step 2: methyl 5-[2-(2,4-diamino-6-oxo-1,6-dihydropyrimidin-5-yl)acetamido]-3-fluoropyridine-2-carboxylate. methyl 5-(2-chloroacetamido)-3-fluoropyridine-2-carboxylate (449 mg, 1.82 mmol), NaI (819 mg, 5.46 mmol), NaHCO₃ (168 mg, 2.00 mmol), 2,6-diamino-3,4-dihydropyrimidin-4-one (253 mg, 2.00 mmol) and DMF (3 mL) were stirred at rt over night. DMF (1 mL) and water (2 mL) was added and the product was collected by filtration. The material was washed with water, 1:1 DMF/water mixture and acetonitrile and dried under vacuum at rt for 30 min. Gave the desired compound (500 mg, 82%). LCMS [M+H]⁺ m/z 337.

Step 3: 5-[2-(2,4-diamino-6-oxo-1,6-dihydropyrimidin-5-yl)acetamido]-3-fluoropyridine-2-carboxylic acid, methyl 5-[2-(2,4-diamino-6-oxo-1,6-dihydropyrimidin-5-yl)acetamido]-3-fluoropyridine-2-carboxylate (500 mg, 1.49 mmol) was added 1M NaOH (5 mL) and water (5 mL). The reaction was stirred for 30 min and the mixture was filtered to get rid of some solid particles. 2M HCl (2 mL) and 1M HCl was added until pH 2. The product was collected by filtration, washed with water and MeCN and dried. Gave 5-[2-(2,4-diamino-6-oxo-1,6-dihydropyrimidin-5-yl)acetamido]-3-fluoropyridine-2-carboxylic acid (240 mg, 50%). LCMS [M+H]⁺ m/z 323. ¹H NMR (400 MHz, DMSO-d₆) δ ppm 13.16 (br. s., 1H), 10.65 (s, 1H), 9.99 (br. s., 1H), 8.56-8.60 (m, 1H), 8.13 (dd, J=13.3, 1.9 Hz, 1H), 6.11 (br. s., 2H), 5.95 (br. s., 2H), 3.33 (s, 2H)

General Procedure A;

X = H or F
1) HOBt, Hünigs base, EDCl, DMSO, rt; 2) 1M NaOH.

Step 1: a mixture of a suitable carboxylic acid (1 equiv.) and an amine HCl salt (1.2 equiv.) were dissolved in DMSO (2 mL). Hünigs base (5.0 equiv.) followed by EDCl (1.5 equiv.) and HOBt (1.5 equiv.) were added and the reaction mixture and was stirred at rt for 18 h. The reaction mixture was filtered, washed with DMSO and purified with acidic preparative HPLC to afford the product as TEA salt.

Step 2: 1 M NaOH (0.3-1 mL) was added to the solid product of Step 1 and the reaction mixture was stirred for 15 min before 2 M HCl was added to obtain a pH of 2-4. The precipitated product was filtered and washed with water (1-3 mL) to generate the desired product as a solid.

EXAMPLES

Example 1: (2S)-2-[(5-{[(2,4-diamino-6-oxo-1,6-dihydropyrimidin-5-yl)carbamoyl]amino}pyridin-2-yl)formamido]pentanedioic acid; trifluoroacetic acid EDCl.HCl (170 mg, 0.48 mmol) and HOBt (45.7 mg, 0.30 mmol) were added to a stirred mixture of 5-{[(2,4-diamino-6-oxo-1,6-dihydropyrimidin-5-yl)carbamoyl]amino}pyridine-2-carboxylic acid (Intermediate 1, 91.0 mg, 0.30 mmol), diethyl (2S)-2-aminopentanedioate-HCl (85.8 mg, 0.36 mmol), Et₃N (0.25 mL, 1.79 mmoL) and DMSO (1 mL). The reaction was stirred in a sealed tube at rt overnight. DMSO (1 mL) was added and the mixture was filtered. MeOH (2 mL) and TEA (0.1 mL) were added to the filtrate and the intermediate ester was purified by acidic preparative HPLC. The pure fractions were combined and the solvents were removed under reduced pressure. LCMS [M+H]⁺ m/z 491. The material was dissolved in a mixture of water (1.6 mL) and 5M NaOH (0.20 mL) and the reaction was stirred for 30 min. DMSO (2 mL) was added and the pH was adjusted to 1 with 1M HCl. The product was purified by acidic preparative HPLC. The pure fractions were combined and the solvents were removed under reduced pressure. The product was dried in a vacuum oven (40° C. overnight). This gave 16 mg (10%) of the title compound as a TFA salt. LCMS [M+H]$^+$ m/z 435; $^1$H NMR (400 MHz, DMSO-d$_6$) δ ppm 12.49 (br. s., 2H), 11.07 (br. s., 1H), 9.28 (br. s., 1H), 8.73 (br. s, 1H), 8.63 (d, J=8.1 Hz, 1H), 8.07 (br. d, J=7.7 Hz, 1H), 7.93 (d, J=8.8 Hz, 1H), 7.19 (br. s., 2H), 7.06 (br. s., 1H), 6.65 (br. s., 2H), 4.46 (td, J=8.7, 4.7 Hz, 1H), 2.24-2.33 (m, 2H), 2.07-2.20 (m, 1H), 1.94-2.06 (m, 1H).

Example 2: (2S)-2-[(5-{[(2,4-diamino-6-oxo-1,6-dihydropyrimidin-5-yl)carbamoyl]amino}pyridin-2-yl)formamido]-3-phenylpropanoic acid; trifluoroacetic acid EDCl.HCl (165 mg, 0.44 mmol) and HOBt (44.5 mg, 0.29 mmol) were added to a stirred mixture of 5-{[(2,4-diamino-6-oxo-1,6-dihydropyrimidin-5-yl)carbamoyl]amino}pyridine-2-carboxylic acid (Intermediate 1, 95.0 mg, 0.29 mmol), methyl (2S)-2-amino-3-phenylpropanoate hydrochloride (75.1 mg, 0.35 mmol), Et$_3$N (0.242 mL, 1.74 mmoL) and DMSO (1 mL). The reaction was stirred in a sealed tube at rt overnight. DMSO (1 mL) was added and the mixture was filtered. MeOH (2 mL) and TFA (0.1 mL) were added to the filtrate and the intermediate ester was purified by acidic preparative HPLC. The pure fractions were combined and the solvents were removed under reduced pressure. LCMS [M+H]$^+$ m/z 467. The material was dissolved in a mixture of water (1.6 mL) and 5M NaOH (0.20 mL) and the reaction was stirred for 30 min. DMSO (2 mL) was added and the pH was adjusted to 1 with 1M HCl. The product was purified by acidic preparative HPLC. The pure fractions were combined and the solvents were removed under reduced pressure. The product was dried in a vacuum oven (40° C. overnight). This gave 7 mg (4%) of the title compound. LCMS [M+H]$^+$ m/z 453; $^1$H NMR (400 MHz, DMSO-d$_6$) δ ppm 12.97 (br. s., 1H), 10.91 (br. s., 1H), 9.27 (br. s., 1H), 8.67 (br. s., 1H), 8.50 (d, J=8.2 Hz, 1H), 8.05 (br. d, J=7.9 Hz, 1H), 7.89 (d, J=8.5 Hz, 1H), 7.14-7.29 (m, 5H), 7.04 (br. s., 2+1 H, two broad singlets), 6.57 (br. s., 2H), 4.65-4.75 (m, 1H), 3.13-3.23 (m, 2H).

Example 3: (2S)-2-[(5-{[(2,4-diamino-6-oxo-1,6-dihydropyrimidin-5-yl)carbamoyl]amino}pyridin-2-yl)formamido]-3-methylbutanoic acid; trifluoroacetic acid EDCl.HCl (144 mg, 0.38 mmol) and HOBt (38.7 mg, 0.25 mmol) were added to a stirred mixture of 5-{[(2,4-diamino-6-oxo-1,6-dihydropyrimidin-5-yl)carbamoyl]amino}pyridine-2-carboxylic acid (Intermediate 1, 77.0 mg, 0.25 mmol), methyl (2S)-2-amino-3-methylbutanoate hydrochloride (50.7 mg, 0.30 mmol), Et$_3$N (0.211 mL, 1.51 mmoL) and DMSO (1 mL). The reaction was stirred in a sealed tube at rt overnight. DMSO (1 mL) was added and the mixture was filtered. MeOH (2 mL) and TFA (0.1 mL) were added to the filtrate and the intermediate ester was purified by acidic preparative HPLC. The pure fractions were combined and the solvents were removed under reduced pressure. LCMS [M+H]$^+$ m/z 419. The obtained material was dissolved in a mixture of water (1.6 mL) and 5M NaOH (0.20 mL) and the reaction was stirred for 30 min. DMSO (2 mL) was added and the pH was adjusted to 1 with 1M HCl. The product was purified by acidic preparative HPLC. The pure fractions were combined and the solvents were removed under reduced pressure. The product was dried in a vacuum oven (40° C. overnight). This gave 8 mg (6%) of the title compound as TFA salt. LCMS [M+H]$^+$ m/z 405; $^1$H NMR (400 MHz, DMSO-d$_6$) δ ppm 12.95 (br. s, 1H), 11.30 (br. s, 1H), 9.36 (br. s., 1H), 8.70 (br. s., 1H), 8.29 (d, J=8.8 Hz, 1H), 8.12 (dd, J=8.6, 2.4 Hz, 1H), 7.95 (d, J=8.5 Hz, 1H), 7.42 (br. s., 2H), 7.11 (br. s., 1H), 6.81 (br. s., 2H), 4.38 (dd, J=9.0, 5.2 Hz, 1H), 2.15-2.27 (m, 1H), 0.86-0.95 (m, 6H).

Example 4: (2S)-2-[(5-{[(2,4-diamino-6-oxo-1,6-dihydropyrimidin-5-yl)carbamoyl]amino}pyridin-2-yl)formamido]-4-(1H-1,2,3,4-tetrazol-5-yl)butanoic acid

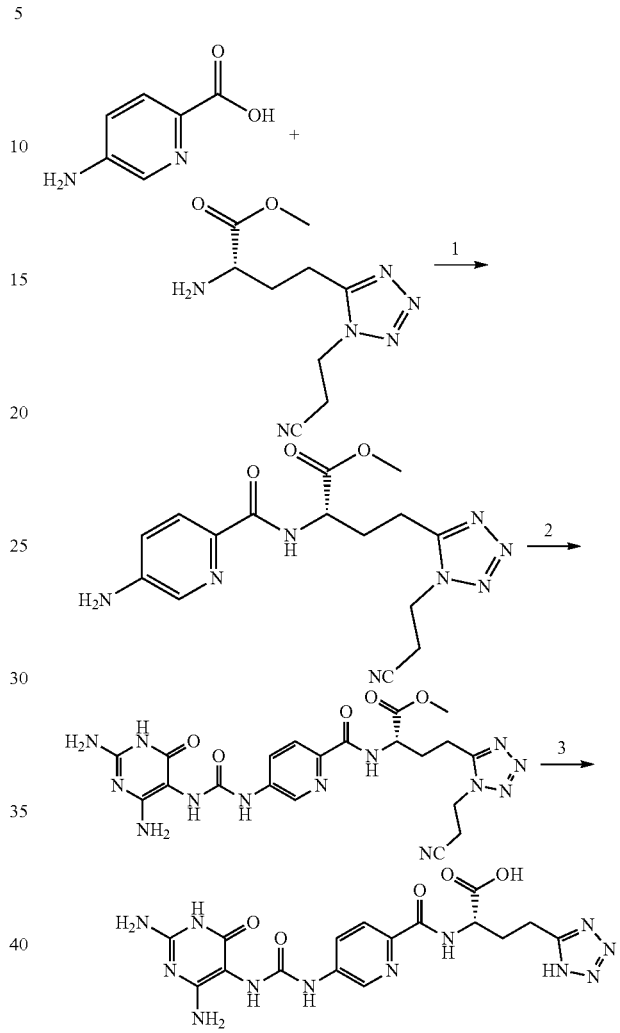

1) TBTU, Et$_3$N, DMF, rt; 2) (i) Et$_3$N, THF, rt; (ii) NaOH, rt; 3) NaOH, rt.

Step 1: methyl (2S)-2-[(5-aminopyridin-2-yl)formamido]-4-[1-(2-cyanoethyl)-1H-1,2,3,4-tetrazol-5-yl]butanoate. 5-Aminopyridine-2-carboxylic acid (138 mg, 1.0 mmol), Et$_3$N (222 mg, 2.2 mmol) and TBTU (484 mg, 1.5 mmol) were dissolved in DMF (2 mL). The reaction mixture was stirred at rt for 10 min. methyl (2S)-2-amino-4-[1-(2-cyanoethyl)-1H-1,2,3,4-tetrazol-5-yl]butanoate hydrochloride (Intermediate 2, 329 mg, 1.2 mmol) was added and stirring was continued overnight. After completion of the reaction, the mixture was diluted with water and extracted with DCM (3×25 mL). The combined organic phases were washed with aq NaHCO$_3$ (10 mL), dried over Na$_2$SO$_4$ and evaporated. The crude product was purified by flash column chromatography (silica gel, 5% MeOH in DCM) to offer the pure title compound as white solid. Yield 216 mg (60%). LCMS [M+H]$^+$ m/z 359.

Step 2: methyl (2S)-4-[1-(2-cyanoethyl)-1H-1,2,3,4-tetrazol-5-yl]-2-[(5-{[(2,4-diamino-6-oxo-1,6-dihydropyrimidin-5-y l)carbamoyl]amino}pyridin-2-yl)formamido]butanoate. To a solution of 4-nitrophenyl chloroformate (134 mg, 0.66 mmol) in dry THF (4 mL) was added a mixture of methyl (2S)-2-[(5-aminopyridin-2-yl)formamido]-4-[1-(2-cyanoethyl)-1H-1,2,3,4-tetrazol-5-yl]butanoate (216 mg, 0.60 mmol) and Et₃N (67 mg, 0.66 mmol). The resulting mixture was stirred at rt for 20 min. In the meantime, to the another round bottom flask 2,5,6-triamino-3,4-dihydropyrimidin-4-one sulfate (158 mg, 0.66 mmol) was dissolved in water (2 mL) and mixed with a 1N NaOH solution (1.81 mL, 1.81 mmol). The mixture changed color several times but eventually turned yellow. Into this yellow aq solution, the THF solution of activated methyl (2S)-4-[1-(2-cyanoethyl)-1H-1,2,3,4-tetrazol-5-yl]-2-({5-[(4-nitrophenoxycarbonyl)amino]pyridin-2-yl}formamido)butanoate intermediate was added dropwise. After stirring at rt for 1 h the precipitate obtained was filtered off and washed with water (2 mL) and CH₃CN (4 mL). After drying, the title compound was obtained as a white solid. Yield 80 mg (25%). LCMS [M+H]⁺ m/z 526.

Step 3: (2S)-2-[(5-{[(2,4-diamino-6-oxo-1,6-dihydropyrimidin-5-yl)carbamoyl]amino}pyridin-2-yl)formamido]-4-(1H-1,2,3,4-tetrazol-5-yl)butanoic acid. To the reaction vial, methyl (2S)-4-[1-(2-cyanoethyl)-1H-1,2,3,4-tetrazol-5-yl]-2-[(5-{[(2,4-diamino-6-oxo-1,6-dihydropyrimidin-5-yl)carbamoyl]amino}pyridin-2-yl)formamido]butanoate (80 mg, 0.15 mmol) was suspended in water (1 mL) and 1N NaOH (0.914 mL, 0.91 mmol) was added. The mixture was heated to 40° C. for 1 h. The reaction vial was then cooled to rt and 1N HCl was added until the solution turned acidic (pH 3-4). The acidic mixture was stirred for further 30 min before the precipitate was collected by filtration. The solid was sequentially washed with water (2 mL) and CH₃CN (4 mL). After drying, the title compound was obtained as a white solid. Yield 38 mg (54%). LCMS [M+H]⁺ m/z 459; $^1$H NMR (400 MHz, DMSO-d₆) δ ppm 10.06 (br. s. 1H), 8.67-8.80 (m, 2H), 8.08 (d, J=7.6 Hz, 1H), 7.91 (d, J=8.8 Hz, 1H), 6.91 (s, 1H), 6.22 (br. s., 2H), 5.96 (br. s., 2H), 4.45 (td, J=8.1, 4.9 Hz, 1H), 2.87-3.02 (m, 2H), 2.31-2.43 (m, 1H), 2.18-2.29 (m, 1H).

Example 5: (2S)-2-[(3-chloro-5-{[(2,4-diamino-6-oxo-1,6-dihydropyrimidin-5 yl)carbamoyl]amino}pyridin-2-yl)formamido]pentanedioic acid Step 1: 1,5-diethyl (2S)-2-[(3-chloro-5-{[(2,4-diamino-6-oxo-1,6-dihydropyrimidin-5-yl)carbamoyl]amino}pyridin-2-yl)formamido]pentanedioate. To a solution of 4-nitrophenyl chloroformate (169 mg, 0.84 mmol) in dry THF (4 mL) was added a mixture of 1,5-diethyl (2S)-2-[(5-amino-3-chloropyridin-2-yl)formamido]pentanedioate (Intermediate 4, 272 mg, 0.76 mmol) and Et₃N (84 mg, 0.84 mmol). The resulting mixture was stirred at rt for 10 min. In the meantime, to another round bottom flask 2,5,6-triamino-3,4-dihydropyrimidin-4-one sulfate (118 mg, 0.84 mmol) was dissolved in water (1 mL) and mixed with a 1N NaOH solution (2.25 mL, 2.3 mmol). The mixture changed color several times but eventually turned yellow. Into this aq solution the THF solution of activated 1,5-diethyl (2S)-2-({3-chloro-5-[(4-nitrophenoxycarbonyl)amino]pyridin-2-yl}formamido)pentanedioate intermediate was added dropwise. After stirring at rt for 1 h the precipitate obtained was filtered off and washed with water (2 mL) and CH₃CN (4 mL). After drying, the title compound was obtained as off-white solid. Yield 127 mg (32%). LCMS [M+H]⁺ m/z 525.

Step 2: (2S)-2-[(3-chloro-5-{[(2,4-diamino-6-oxo-1,6-dihydropyrimidin-5 yl)carbamoyl]amino}pyridin-2-yl)formamido]pentanedioic acid. To the reaction vial, 1,5-diethyl (2S)-2-[(3-chloro-5-{[(2,4-diamino-6-oxo-1,6-dihydropyrimidin-5-yl)carbamoyl]amino}pyridin-2-yl)formamido]pentanedioate (127 mg, 0.24 mmol) was suspended in water (1 mL) and a 1N NaOH (1.45 mL, 1.45 mmol) was added. The mixture was stirred at rt for 3 h upon which it slowly turned into a clear solution. 1N HCl was added until the solution turned acidic (pH 3-4) and the mixture was stirred for a further 30 min before the precipitate was collected by filtration. The solid was sequentially washed with water (2 mL) and CH₃CN (4 mL). After drying, the title compound was obtained as white solid. Yield 54 mg (48%). LCMS [M+H]⁺ m/z 469; $^1$H NMR (400 MHz, DMSO-d₆) δ ppm 12.54 (br. s., 1H), 9.99 (br. s., 1H), 8.67 (d, J=7.9 Hz, 1H), 8.56 (br. s., 1H), 8.23 (d, J=1.6 Hz, 1H), 6.99 (br. s., 1H),

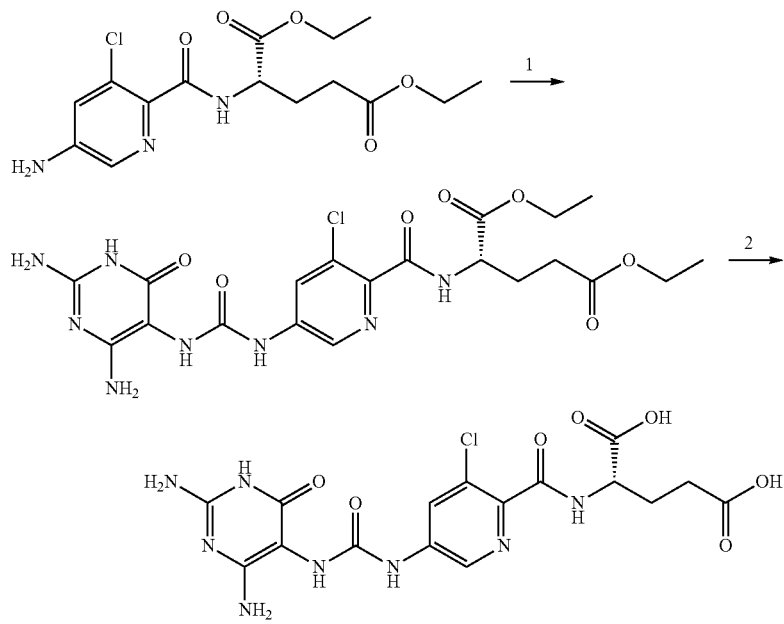

1) (i) 4-Nitrophenyl chloroformate, Et₃N, THF, rt; (ii) 2,5,6-triamino-3,4-dihydropyrimidin-4-one sulfate, aq NaOH, rt; 2) 1N NaOH, rt.

6.19 (br. s., 2H), 5.97 (br. s., 2H), 4.38 (td, J=8.5, 5.2 Hz, 1H), 2.26-2.37 (m, 2H), 2.01-2.14 (m, 1H), 1.87-2.00 (m, 1H).

Example 6: (2S)-2-[(5-{[(2,4-diamino-6-oxo-1,6-dihydropyrimidin-5-yl)carbamoyl]amino}-3-fluoropyridin-2-yl)formamido]pentanedioic acid

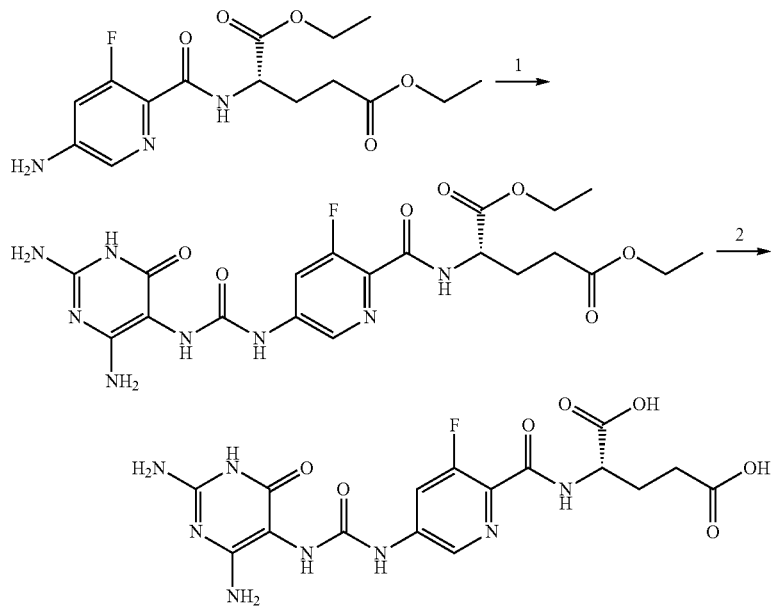

1) (i) 4-Nitrophenyl chloroformate, Et₃N, THF, rt; (ii) 2,5,6-triamino-3,4-dihydropyrimidin-4-one sulfate, aq NaOH, rt; 2) 1N NaOH, rt.

Step 1: 1,5-diethyl (2S)-2-[(5-{[(2,4-diamino-6-oxo-1,6-dihydropyrimidin-5-yl)carbamoyl]amino}-3-fluoropyridin-2-yl)formamido]pentanedioate. To a mixture of 4-nitrophenyl chloroformate (138 g, 0.67 mmol) in dry THF (4 mL) was added a mixture of 1,5-diethyl (2S)-2-[(5-amino-3-fluoropyridin-2-yl)formamido]pentanedioate (Intermediate 10, 213 mg, 0.62 mmol) and Et₃N (69 mg, 0.86 mmol). The resulting mixture was stirred at rt for 20 min. In the meantime, to the another round bottom flask 2,5,6-triamino-3,4-dihydropyrimidin-4-one sulfate (164 mg, 0.86 mmol) was dissolved in water (1 mL) and mixed with a 1N NaOH solution (1.87 mL, 1.9 mmol). The mixture changed color several times but eventually turned yellow. Into this yellow aq solution, the THF solution of activated 1,5-diethyl (2S)-2-({3-fluoro-5-[(4-nitrophenoxycarbonyl)amino]pyridin-2-yl}formamido)pentanedioate intermediate was added dropwise. After stirring at rt for 1 h the precipitate obtained was filtered off and washed with water (2 mL) and CH₃CN (4 mL). After drying, the product was obtained as a white solid. Yield 80 mg (26%). LCMS [M+H]⁺ m/z 509.

Step 2: (2S)-2-[(5-{[(2,4-diamino-6-oxo-1,6-dihydropyrimidin-5-yl)carbamoyl]amino}-3-fluoropyridin-2-yl)formamido]pentanedioic acid. To the reaction vial, 1,5-diethyl (2S)-2-[(5-{[(2,4-diamino-6-oxo-1,6-dihydropyrimidin-5-yl)carbamoyl]amino}-3-fluoropyridin-2-yl)formamido]pentanedioate (80 mg, 0.16 mmol) was suspended in water (1 mL) and a 1N NaOH (0.94 mL, 0.94 mmol) was added. The mixture was stirred at rt for 3 h during which it slowly turned into a clear solution. 1N HCl was added until the solution turned acidic (pH 3-4) and the mixture was stirred for further 30 min before the precipitate was collected by filtration. The solid was sequentially washed with water (2 mL) and CH₃CN (4 mL). After drying, the title compound was obtained as white solid. Yield 42 mg (59%). LCMS [M+H]⁺ m/z 453; ¹H NMR (400 MHz, DMSO-d₆) δ ppm 12.51 (br. s., 1H), 10.00 (br. s., 1H), 8.56 (d, J=8.2 Hz, 1H), 8.45 (br. s., 1H), 8.04 (d, J=13.9 Hz, 1H), 7.01 (br. s., 1H), 6.20 (br. s., 2H), 5.97 (br. s., 2H), 4.39 (td, J=8.4, 5.1 Hz, 1H), 2.25-2.37 (m, 2H), 2.05-2.17 (m, 1H), 1.90-2.03 (m, 1H).

Example 7: (2S)-2-((5-[2-(2,4-diamino-6-oxo-1,6-dihydropyrimidin-5-yl)acetamido]pyridin-2-yl)formamido)pentanedioic acid hydrochloride HATU (188 mg, 0.50 mmol) was added to a stirred mixture of 5-[2-(2,4-diamino-6-oxo-1,6-dihydropyrimidin-5-yl)acetamido]pyridine-2-carboxylic acid (Intermediate 9, 116 mg, 0.38 mmol), 1,5-diethyl (2S)-2-aminopentanedioate hydrochloride (101 mg, 0.42 mmol), Et₃N (0.320 mL, 2.30 mmoL) and DMSO (0.50 mL). The reaction was stirred in a sealed tube at rt for 2 h. Water (0.7 mL) was added and the mixture was stirred vigorously for 1 h. The intermediate ester was collected by filtration and washed with water (1 mL). [M+H]⁺ m/z 490. The material was dissolved in a mixture of MeOH (10 mL) and 1M HCl (0.5 mL) and the product was purified by acidic preparative HPLC. The pure fractions were combined and the solvents were removed under reduced pressure. The remaining material was dissolved in a mixture of water (1 mL) and 5M NaOH (0.2 mL) and the mixture was stirred for 30 min. The pH was adjusted to 3 with 12M HCl (50 μL) and 1M HCl and the product was collected by filtration, washed with water (0.5 mL) and dried under reduced pressure. The solid was added to water (4 mL) and 1M HCl (0.1 mL) and heated in a sealed tube at 80° C. for 2 min. The water was removed under reduced pressure. This gave 7.0 mg (4%) of the title compound. [M+H]⁺ m/z 434; ¹H NMR (400 MHz, DMSO-d₆) δ ppm 11.98 (br. s., 2H), 10.53 (s, 1H), 8.90 (dd, J=2.4, 0.6 Hz, 1H), 8.71 (d, J=8.2 Hz, 1H), 8.18 (br. s, 2H), 8.19 (dd, J=8.6, 2.4 Hz, 1H), 7.96-8.01 (m, 1H), 7.23 (br. s., 2H), 4.46 (td, J=8.7, 4.7 Hz, 1H), 3.42 (s, 2H), 2.23-2.34 (m, 2H), 2.07-2.19 (m, 1H), 1.94-2.06 (m, 1H).

Example 8: (2S)-2-({5-[2-(2,4-diamino-6-oxo-1,6-dihydropyrimidin-5-yl)acetamido]pyridin-2-yl}formamido)-3-phenylpropanoic acid HATU (138 mg, 0.36 mmol) was added to a stirred mixture of 5-[2-(2,4-diamino-6-oxo-1,6-dihydropyrimidin-5-yl)acetamido]pyridine-2-carboxylic acid (Intermediate 9, 85.0 mg, 0.28 mmol), methyl (2S)-2-amino-3-phenyl-propanoate-HCl (66.3 mg, 0.31 mmol), Et$_3$N (0.230 mL, 1.65 mmoL) and DMSO (0.50 mL). The reaction was stirred in a sealed tube for 90 min at rt. Water (0.50 mL) was added and the mixture was stirred vigorously for 30 min. The intermediate ester was collected by filtration and washed with water (1 mL). LCMS [M+H]$^+$ m/z 466. Water (0.30 mL) and 5M NaOH (0.30 mL) was added to the wet solid and the mixture was stirred for 30 min. Water (10 mL) and 1M HCl (2.0 mL) was added and the product was purified by acidic preparative HPLC. The pure fractions were combined and the solvents were removed under reduced pressure. The material was dissolved in a mixture of water (1.5 mL) and 5M NaOH (50 µL). The pH was adjusted to ~3 with 1M HCl. The product was collected by filtration, washed with water (1 mL) and dried under reduced pressure. This gave 8.0 mg (6%) of the title compound. LCMS [M+H]$^+$ m/z 452; $^1$H NMR (400 MHz, DMSO-d$_6$) δ ppm 10.40 (s, 1H), 10.04 (br. s., 1H), 8.80 (dd, J=2.4, 0.6 Hz, 1H), 8.57 (d, J=8.2 Hz, 1H), 8.16 (dd, J=8.6, 2.4 Hz, 1H), 7.90-7.95 (m, 1H), 7.14-7.29 (m, 5H), 6.17 (br. s., 2H), 5.98 (br. s., 2H), 4.70 (td, J=7.8, 5.7 Hz, 1H), 3.31 (br. s., 2H), 3.17-3.21 (m, 2H).

Example 9: (2S)-2-((5-[2-(2,4-diamino-6-oxo-1,6-dihydropyrimidin-5-yl)acetamido]pyridin-2-yl)formamido)-4-(1H-1,2,3,4-tetrazol-5-yl)butanoic acid HATU (94.2 mg, 0.25 mmol) was added to a stirred mixture of 5-[2-(2,4-diamino-6-oxo-1,6-dihydropyrimidin-5-yl)acetamido]pyridine-2-carboxylic acid (Intermediate 9, 58.0 mg, 0.19 mmol), methyl (2S)-2-amino-4-[1-(2-cyanoethyl)-1H-1,2,3,4-tetrazol-5-yl]butanoate hydrochloride (Intermediate 2, 57.6 mg, 0.21 mmol), Et$_3$N (0.400 mL, 2.87 mmoL) and DMSO (0.50 mL). The reaction was stirred in a sealed tube for 90 min at rt. Water (0.50 mL) and 1M HCl (3 mL) were added. The pH was adjusted to 3 with 1M NaOH and the mixture was stirred vigorously for 30 min. The intermediate ester was collected by filtration and washed with water (1 mL). LCMS [M+H]$^+$ m/z 525. The material was dissolved in a mixture of water (8 mL) and 1M HCl (0.50 mL) and the product was purified by acidic preparative HPLC. The pure fractions were combined and the solvents were removed under reduced pressure. The resulting material was dissolved in a mixture of water (1.0 mL) and 5M NaOH (0.20 mL) and the reaction was stirred for 2 h. The pH was adjusted to 3 with 1M HCl and the product was collected by filtration, washed with water (0.10 mL) and dried under reduced pressure. This gave 5.0 mg (6%) of the title compound. LCMS [M+H]$^+$ m/z 458; $^1$H NMR (400 MHz, DMSO-d$_6$) δ ppm 10.40 (s, 1H), 9.96 (br. s., 1H), 8.86 (dd, J=2.4, 0.4 Hz, 1H), 8.82 (d, J=8.1 Hz, 1H), 8.18 (dd, J=8.6, 2.4 Hz, 1H), 7.97 (br. d, J=8.5 Hz, 1H), 6.08 (br. s., 2H), 5.95 (br. s, 2H), 4.49 (td, J=8.5, 4.7 Hz, 1H), 3.32 (s, 2H), 2.87-3.01 (m, 2H), 2.20-2.43 (m, 2H).

Example 10: (2S)-2-((5-[2-(2,4-diamino-6-oxo-1,6-dihydropyrimidin-5-yl)acetamido]-3-fluoropyridin-2-yl)formamido)pentanedioic acid

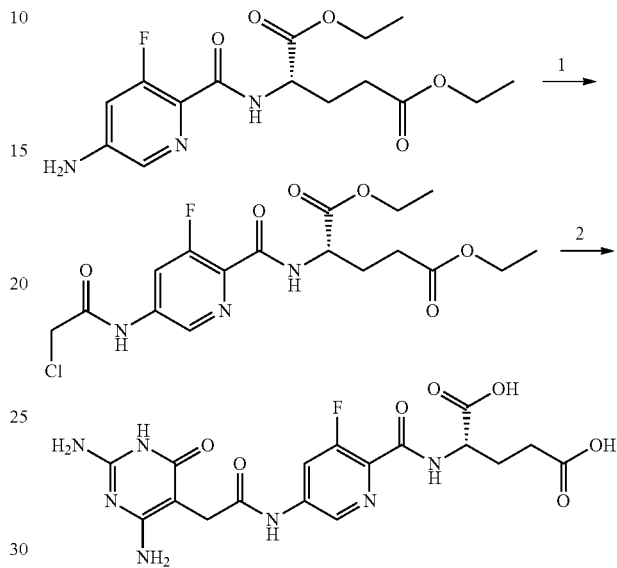

1) 2-Chloroacetyl chloride, Et$_3$N, DCM, rt; 2) 2,4-diamino-1H-pyrimidin-6-one, NaHCO$_3$, NaI, DMF, rt.

Step 1: 1,5-diethyl (2S)-2-{[5-(2-chloroacetamido)-3-fluoropyridin-2-yl]formamido}pentanedioate. 2-Chloroacetyl chloride (22.0 µL, 0.28 mmol) was added to a stirred mixture of 1,5-diethyl (2S)-2-[(5-amino-3-fluoropyridin-2-yl)formamido]pentanedioate (Intermediate 10, 92.0 mg, 0.27 mmol), Et$_3$N (21.0 µL, 0.30 mmol) and DCM (3 mL) at rt The reaction was stirred for 3 min and the product was washed with diluted Na$_2$CO$_3$. The organic phase was dried over Na$_2$SO$_4$ and removed under reduced pressure. This gave 95 mg (84%) of the desired intermediate. [M+H]$^+$ m/z 418.

Step 2: (2S)-2-({5-[2-(2,4-diamino-6-oxo-1,6-dihydropyrimidin-5-yl)acetamido]-3-fluoropyridin-2-yl}formamido)pentanedioic acid. 2,6-diamino-3,4-dihydropyrimidin-4-one (43.2 mg, 0.34 mmol), NaHCO$_3$ (28.8 mg, 0.34 mmol) and NaI (187 mg, 1.25 mmol) was added to a stirred solution of 1,5-diethyl (2S)-2-{[5-(2-chloroacetamido)-3-fluoropyridin-2-yl]formamido}pentanedioate (95 mg, 0.23 mmol) in DMF (1 mL). The reaction was stirred in a sealed tube at rt overnight. MeOH (3 mL) and 1M HCl (0.1 mL) was added to the mixture and the product was purified by acidic preparative HPLC. The pure fractions were combined and the solvents were removed under reduced pressure. [M+H]$^+$ m/z 508. The material was dissolved in a mixture of water (1 mL) and 5M NaOH (0.2 mL) and the mixture was stirred for 30 min. The pH was adjusted to 3 with 1M HCl and the product was collected by filtration, washed with water (1 mL) and dried under reduced pressure. This gave 26 mg (25%) of the title compound. [M+H]$^+$ m/z 452; $^1$H NMR (400 MHz, DMSO-d$_6$) δ ppm 12.40 (br. s., 2H), 10.68 (s, 1H), 10.02 (br. s., 1H), 8.64 (d, J=8.1 Hz, 1H), 8.62 (dd, J=1.9, 1.3 Hz, 1H), 8.12 (dd, J=13.4, 1.9 Hz, 1H), 6.16 (br.

s, 2H), 5.95 (br. s, 2H), 4.36-4.46 (m, 1H), 3.34 (s, 2H), 2.26-2.34 (m, 2H), 2.04-2.16 (m, 1H), 1.90-2.03 (m, 1H).

Example 11: (2S)-3-cyclopentyl-2-[(5-{[(2,4-di-amino-6-oxo-1,6-dihydropyrimidin-5-yl)carbamoyl]amino}pyridin-2-yl)formamido]propanoic acid Step 1: 5-{[(2,4-diamino-6-oxo-1,6-dihydropyrimidin-5-yl)carbamoyl]amino}pyridine-2-carboxylic acid (Intermediate 1.60 mg, 0.2 mmol) and methyl 2-amino-3-cyclopentyl-propanoate hydrochloride (49 mg, 0.24 mmol) were dissolved in DMSO (2 mL). EDCl (56 mg, 0.29 mmol) and HOBt (88 mg, 0.66 mmol) were then added and the reaction mixture was stirred at rt for 18 h. The reaction mixture was filtered, washed with DMSO (1 mL) and purified with acidic Preparative HPLC to obtain the title compound. LCMS [M+H]$^+$ 459.

Step 2: 1 M NaOH (1 mL) was added to the solid obtained in Step 1 and the reaction was stirred for 15 min before 2 M HCl was added to obtain a pH to 2-4. The precipitated product was filtered and washed with water (1 mL) to generate the title compound as a white solid (9 mg, 10%, 2 steps). LCMS [M+H]+ 445; 1H NMR (400 MHz, DMSO-$d_6$) δ ppm 12.76 (br. s., 1H) 10.11 (br. s., 1H) 9.21 (br. s., 1H) 8.71 (s, 1H) 8.49 (d, J=8.5 Hz, 1H) 8.08 (d, J=7.3 Hz, 1H) 7.92 (d, J=8.5 Hz, 1H) 6.89 (br. s., 1H) 6.31 (br. s., 2H) 6.01 (br. s., 2H) 4.38-4.49 (m, 1H) 1.67-1.96 (m, 6H) 1.51-1.62 (m, 2H) 1.38-1.51 (m, 2H) 1.01-1.18 (m, 2H).

Example 12: (2S)-2-cyclohexyl-2-[(5-{[(2,4-di-amino-6-oxo-1,6-dihydropyrimidin-5-yl)carbamoyl]amino}pyridin-2-yl)formamido]acetic acid Prepared according to General Procedure A from 5-{[(2,4-diamino-6-oxo-1,6-dihydropyrimidin-5-yl)carbamoyl]amino}pyridine-2-carboxylic acid (Intermediate 1.60 mg, 0.20 mmol) and methyl (2S)-2-amino-2-cyclohexyl-acetate-HCl (47 mg, 0.23 mmol) to generate the title compound as a white solid (9 mg, 10%, 2 steps). LCMS [M+H]$^+$ 445; $^1$H NMR (400 MHz, DMSO-$d_6$) δ ppm 12.96 (br. s., 1H), 10.18 (br. s., 1H), 9.20 (br. s., 1H), 8.68 (br. s., 1H), 8.28 (d, J=8.8 Hz, 1H), 8.11 (d, J=8.2 Hz, 1H), 7.92 (d, J=8.8 Hz, 1H), 6.89 (br. s., 1H), 6.35 (br. s., 2H), 6.07 (br. s., 2H), 4.37 (dd, J=8.5, 6.0 Hz, 1H), 1.78-1.97 (m, 1H), 1.53-1.76 (m, 5H), 0.94-1.31 (m, 5H).

Example 13: (2S)-2-({5-[2-(2,4-diamino-6-oxo-1,6-dihydropyrimidin-5-yl)acetamido]pyridin-2-yl}formamido)-3-methylbutanoic acid HATU (179 mg, 0.47 mmol) was added to a stirred mixture of 5-[2-(2,4-diamino-6-oxo-1,6-dihydropyrimidin-5-yl)acetamido]pyridine-2-carboxylic acid (Intermediate 9, 110 mg, 0.36 mmol), methyl (2S)-2-amino-3-methylbutanoate hydrochloride (66.7 mg, 0.40 mmol), Et$_3$N (0.300 mL, 2.16 mmoL) and DMSO (0.50 mL). The reaction was stirred in a sealed tube for 90 min at rt. Water (0.7 mL) was added and the mixture was stirred vigorously for 1 h. The intermediate ester was collected by filtration and washed with water (1 mL). LCMS [M+H]$^+$ m/z 418. The obtained material was dissolved in a mixture of MeOH (5 mL) and TFA (0.3 mL) and the product was purified by acidic preparative HPLC. The pure fractions were combined and the solvents were removed under reduced pressure. The material was dissolved in a mixture of water (1 mL) and 5M NaOH (0.2 mL) and the reaction was stirred for 30 min. The pH was adjusted to 3 with 12M HCl (60 µL) and 1M HCl and the product was collected by filtration, washed with water (0.5 mL) and dried under reduced pressure. This gave 14 mg (10%) of the title compound. LCMS [M+H]$^+$ m/z 404; $^1$H NMR (400 MHz, DMSO-$d_6$) δ ppm 10.43 (s, 1H), 9.98 (br. s., 1H), 8.82 (dd, J=2.4, 0.7 Hz, 1H), 8.33 (d, J=8.8 Hz, 1H), 8.22 (dd, J=8.5, 2.4 Hz, 1H), 7.97-8.01 (m, 1H), 6.10 (br. s., 2H), 5.96 (s, 2H), 4.38 (dd, J=8.8, 5.2 Hz, 1H), 3.32 (s, 2H), 2.15-2.29 (m, 1H), 0.90-0.95 (m, 6H).

Example 14: (2S)-2-[(5-{[(2,4-diamino-6-oxo-1,6-dihydropyrimidin-5-yl)carbamoyl]amino}pyridin-2-yl)formamido]-4-phenylbutanoic acid Prepared according to General Procedure A from 5-{[(2,4-diamino-6-oxo-1,6-dihydropyrimidin-5-yl)carbamoyl]amino}pyridine-2-carboxylic acid (Intermediate 1.52 mg, 0.17 mmol) and ethyl (2S)-2-amino-4-phenylbutanoate hydrochloride -(62 mg, 0.26 mmol) to yield the title compound as a white solid (7 mg, 8%, 2 steps). LCMS [M+H]$^+$ m/z 439; 1H NMR (400 MHz, DMSO-$d_6$) δ ppm 10.26 (br. s., 1H), 9.31 (br. s., 1H), 8.73 (s, 1H), 8.66 (d, J=8.2 Hz, 1H), 8.08 (d, J=7.9 Hz, 1H), 7.93 (d, J=8.5 Hz, 1H), 7.12-7.34 (m, 5H), 6.92 (br. s., 1H), 6.49 (br. s., 2H), 6.14 (br. s., 2H), 4.42 (td, J=8.0, 5.8 Hz, 1H), 2.54-2.74 (m, 2H), 2.06-2.23 (m, 2H).

Example 15: (2S)-2-[(5-{[(2,4-diamino-6-oxo-1,6-dihydropyrimidin-5-yl)carbamoyl]amino}pyridin-2-yl)formamido]-2-phenylacetic acid Prepared according to General Procedure A from 5-{[(2,4-diamino-6-oxo-1,6-dihydropyrimidin-5-yl)carbamoyl]amino}pyridine-2-carboxylic acid (Intermediate 1.60 mg, 0.2 mmol) and methyl (2S)-2-amino-2-phenylacetate hydrochloride (59 mg, 0.29 mmol) to generate the title compound as a white solid (7 mg, 8%, 2 steps). LCMS [M+H]$^+$ m/z 439; $^1$H NMR (400 MHz, DMSO-$d_6$) δ ppm 10.09 (br. s., 1H), 9.18 (br. s., 1H), 8.80 (d, J=7.6 Hz, 1H), 8.69 (br. s., 1H), 8.05-8.14 (m, 1H), 7.90 (d, J=8.8 Hz, 1H), 7.27-7.49 (m, 5H), 6.88 (br. s., 1H), 6.30 (br. s., 2H), 6.03 (br. s., 2H), 5.52 (d, J=7.6 Hz, 1H).

Example 16: (2S)-4-[(benzenesulfonyl)carbamoyl]-2-[(5-{[(2,4-diamino-6-oxo-1,6-dihydropyrimidin-5-yl)carbamoyl]amino}pyridin-2-yl)formamido]butanoic acid Prepared according to General Procedure A from 5-{[(2,4-diamino-6-oxo-1,6-dihydropyrimidin-5-yl)carbamoyl]amino}pyridine-2-carboxylic acid (Intermediate 1.60 mg, 0.20 mmol) and methyl (2S)-2-amino-4-[(benzenesulfonyl)carbamoyl]butanoate hydrochloride (99 mg, 0.29 mmol) to generate the title compound as a white solid (12 mg, 11%, 2 steps). LCMS [M+H]$^+$ m/z 574; $^1$H NMR (400 MHz, DMSO-$d_6$) δ ppm 12.07 (br. s., 1H), 10.01 (br. s., 1H), 9.14 (br. s., 1H), 8.71 (d, J=1.6 Hz, 1H), 8.60 (d, J=8.2 Hz, 1H), 8.05 (d, J=7.3 Hz, 1H), 7.86-7.95 (m, 3H), 7.65-7.73 (m, 1H), 7.56-7.64 (m, 2H), 6.84 (br. s., 1H), 6.22 (br. s., 2H), 5.98 (br. s., 2H), 4.33 (td, J=8.9, 4.6 Hz, 1H), 2.22-2.40 (m, 2H), 1.97-2.10 (m, 1H), 1.83-1.96 (m, 1H).

Example 17; (2S)-2-[(5-{[(2,4-diamino-6-oxo-1,6-dihydropyrimidin-5-yl)carbamoyl]amino}pyridin-2-yl)formamido]hexanedioic acid Prepared according to General Procedure A from 5-{[(2,4-diamino-6-oxo-1,6-dihydropyrimidin-5-yl)carbamoyl]

amino}pyridine-2-carboxylic acid (Intermediate 1.80 mg, 0.26 mmol) and 1,6-dimethyl (2S)-2-aminohexanedioate hydrochloride (88 mg, 0.39 mmol) to generate the title compound as a white solid (8 mg, 7%, 2 steps). LCMS [M+H]$^+$ m/z 449; $^1$H NMR (400 MHz, DMSO-d$_6$) δ ppm 12.79 (br. s., 1H), 12.07 (br. s., 1H), 10.81 (br. s., 1H), 9.23 (br. s., 1H), 8.71 (br. s., 1H), 8.53 (d, J=8.2 Hz, 1H), 8.04-8.16 (m, 1H), 7.89-7.96 (m, 1H), 6.77-7.21 (m, 3H), 6.49 (br. s., 2H), 4.42 (td, J=8.3, 4.9 Hz, 1H), 2.19-2.29 (m, 2H), 1.73-1.93 (m, 1H), 1.45-1.61 (m, 2H).

Example 18: (2S)-2-[(6-cyclopropoxy-5-{[(2,4-diamino-6-oxo-1,6-dihydropyrimidin-5-yl)carbamoyl]amino}pyridin-2-yl)formamido]pentanedioic acid and after the completion it was diluted with water (20 mL), sat NaHCO$_3$ (5 mL) and EtOAc (25 mL). The organic layer was separated and discarded. The aq layer was acidified using 1N HCl (pH 4-5) and then extracted with DCM (3×30 mL). The combined organic layer was washed with brine, dried (Na$_2$SO$_4$) and concentrated to provide crude product which was used in the next step without purification. Yield 180 mg (79%). LCMS [M+H]$^+$ m/z 225.

Step 2: 1,5-diethyl (2S)-2-[(6-cyclopropoxy-5-nitropyridin-2-yl)formamido]pentanedioate. 6-Cyclopropoxy-5-nitropyridine-2-carboxylic acid (180 mg, 0.81 mmol), Et$_3$N (243 mg, 2.41 mmol) and TBTU (393 mg, 1.22 mmol) were dissolved in THF (4 mL). The reaction mixture stirred at rt for 10 min. 1,5-Diethyl (2S)-2-aminopentanedioate·HCl (288 mg, 1.21 mmol) was added and stirring was continued

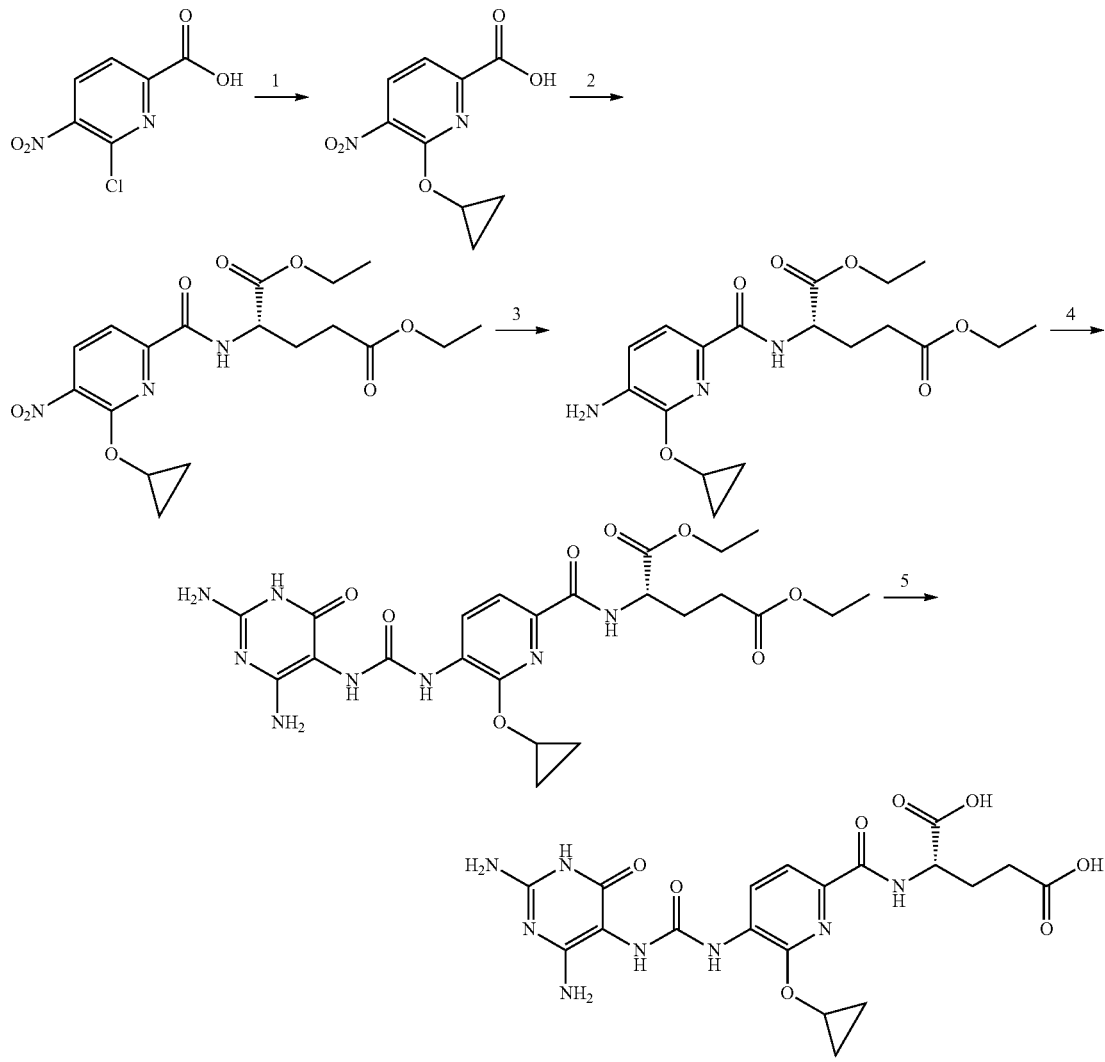

1) Cyclopropanol, Cs$_2$CO$_3$, DMSO, rt; 2) 1,5-diethyl (2S)-2-aminopentanedioate·HCl, TBTU, Et$_3$N, THF, rt; 3) SnCl$_2$·2H$_2$O, EtOH, 90° C; 4) (i) Et$_3$N, THF, rt; (ii) NAOH, rt; 5) 1N NAOH, rt.

Step 1: 6-cyclopropoxy-5-nitropyridine-2-carboxylic acid. In a reaction tube 6-chloro-5-nitropyridine-2-carboxylic acid (203 mg, 1.0 mmol), cyclopropanol (70 mg, 1.2 mmol) and dry powdered Cs$_2$CO$_3$ (1042 mg, 3.2 mmol) were mixed in DMSO (2 mL) and the resulting mixture was stirred at rt for 12 h. The reaction was monitored by LCMS overnight. After completion of the reaction, volatiles were removed and the residue was diluted with water (20 mL) and extracted with DCM (3×30 mL). The combined organic phases were dried over Na$_2$SO$_4$ and evaporated to offer crude compound which was used without purification in the next step. Yield 276 mg (84%). LCMS [M+H]$^+$ m/z 410.

Step 3: 1,5-diethyl (2S)-2-[(5-amino-6-cyclopropoxypyridin-2-yl)formamido]pentanedioate. SnCl$_2$.2H$_2$O (914 mg, 4.04 mmol) was added into a solution of 1,5-diethyl (2S)-2-[(6-cyclopropoxy-5-nitropyridin-2-yl)formamido]pentanedioate (276 mg, 0.67 mmol) in EtOH (10 mL). The reaction mixture was heated to 90° C. for 1 h. After completion, the mixture was cool to rt and volatiles were removed. The residue was then diluted with water water (10 mL) and DCM (20 mL). Sat NaHCO$_3$ was added until the solution turned basic (pH 8-9). The precipitate was filtered and the layers were separated. The aq layer was further extracted with DCM (2×20 mL). The combined organic layer was washed with brine, dried over sodium sulfate and concentrated under reduced pressure to provide crude product which was purified by flash column chromatography (silica gel, 5% MeOH in DCM) to offer pure compound as off-white solid. Yield 194 mg (76%). LCMS [M+H]$^+$ m/z 380.

Step 4: 1,5-diethyl (2S)-2-[(6-cyclopropoxy-5-{[(2,4-diamino-6-oxo-1,6-dihydropyrimidin-5-yl)carbamoyl]amino}pyridin-2-yl)formamido]pentanedioate. To a solution of 4-nitrophenyl chloroformate (124 mg, 0.61 mmol) in dry THF (2 mL) was added a mixture of 1,5-diethyl (2S)-2-[(5-amino-6-cyclopropoxypyridin-2-yl)formamido]pentanedioate (194 mg, 0.51 mmol) and Et$_3$N (62 mg, 0.61 mmol). The resulting mixture was stirred at rt for 20 min. In the meantime, to a another round bottom flask 2,5,6-triamino-3,4-dihydropyrimidin-4-one sulfate (135 mg, 0.56 mmol) was dissolved in water (1 mL) and mixed with a 1N NaOH solution (1.53 mL, 1.53 mmol). The mixture changed color several times but eventually turned yellow. Into this yellow aq solution, THF solution of activated 1,5-diethyl (2S)-2-[(5-amino-6-cyclopropoxypyridin-2-yl)formamido]pentanedioate intermediate was added dropwise. After stirring at rt for 1 h the precipitate obtained was filtered off and washed with water (2 mL) and CH$_3$CN (4 mL). After drying the title compound was obtained. Yield 36 mg (13%). LCMS [M+H]$^+$ m/z 547.

Step 5: (2S)-2-[(6-cyclopropoxy-5-{[(2,4-diamino-6-oxo-1,6-dihydropyrimidin-5-yl)carbamoyl]amino}pyridin-2-yl)formamido]pentanedioic acid. To the reaction vial 1,5-diethyl (2S)-2-[(6-cyclopropoxy-5-{[(2,4-diamino-6-oxo-1,6-dihydropyrimidin-5-yl)carbamoyl]amino}pyridin-2-yl)formamido]pentanedioate (36 mg, 0.07 mmol) was suspended in water (1 mL) and a 1N NaOH (0.394 mL, 0.39 mmol) was added. The mixture was stirred at rt for 3 h during which it slowly turned into a clear solution. 1N HCl was added until the solution turned acidic (pH 3-4) and the mixture was stirred for a further 30 min before the precipitate was collected by filtration. The solid was sequentially washed with water (2 mL) and CH$_3$CN (4 mL). After drying, the title compound was obtained. Yield 22 mg (68%). LCMS [M+H]$^+$ m/z 491; $^1$H NMR (400 MHz, DMSO-d$_6$) δ ppm 12.56 (br. s., 1H), 10.05 (br. s., 1H), 8.50-8.53 (m, 1H), 8.45 (d, J=7.9 Hz, 1H), 8.27 (br. s., 1H), 7.60 (d, J=8.2 Hz, 2H), 6.21 (br. s., 2H), 5.95 (br. s., 2H), 4.66 (tt, J=6.2, 3.0 Hz, 1H), 4.43 (td, J=8.1, 5.2 Hz, 1H), 2.28-2.36 (m, 2H), 2.08-2.19 (m, 1H), 1.94-2.06 (m, 1H), 0.70-0.93 (m, 4H).

Example 19: (2S)-2-((3-chloro-5-[2-(2,4-diamino-6-oxo-1,6-dihydropyrimidin-5-yl)acetamido]pyridin-2-yl)formamido)pentanedioic acid

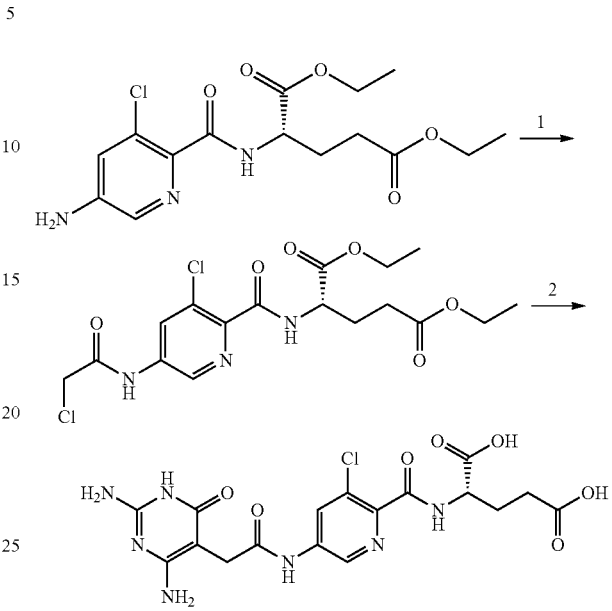

1) 2-Chloroacetyl chloride, Et$_3$N, DCM, rt; 2) 2,4-Diamino-1H-pyrimidin-6-one, NaHCO$_3$, NaI, DMF, rt.

Step 1: 1,5-diethyl (2S)-2-{[3-chloro-5-(2-chloroacetamido)pyridin-2-yl]formamido}pentanedioate. 2-Chloroacetyl chloride (35.0 µL, 0.44 mmol) was added to a stirred mixture of 1,5-diethyl (2S)-2-[(5-amino-3-chloropyridin-2-yl)formamido]pentanedioate (Intermediate 4, 145 mg, 0.41 mmol), Et$_3$N (62.0 µL, 0.45 mmol) and DCM (5 mL) at rt. The reaction was stirred for 5 min. and the product was washed with diluted Na$_2$CO$_3$. The organic phase was dried over Na$_2$SO$_4$ and removed under reduced pressure. This gave 130 mg (74%) of the desired intermediate. [M+H]$^+$ m/z 434.

Step 2: (2S)-2-({3-chloro-5-[2-(2,4-diamino-6-oxo-1,6-dihydropyrimidin-5-yl)acetamido]pyridin-2-yl}formamido)pentanedioic acid. 2,6-diamino-3,4-dihydropyrimidin-4-one (41.5 mg, 0.33 mmol), NaHCO$_3$ (27.7 mg, 0.33 mmol) and NaI (179 mg, 1.20 mmol) was added to a stirred solution of diethyl (2S)-2-[[3-chloro-5-[(2-chloroacetyl)amino]pyridine-2-carbonyl]amino]pentanedioate (130 mg, 0.30 mmol) in DMF (1 mL). The reaction was stirred in a sealed tube at rt overnight. MeOH (3 mL) and 1M HCl (0.4 mL) was added to the mixture and the product was purified by acidic preparative HPLC. The pure fractions were combined and the solvents were removed under reduced pressure. [M+H]$^+$ m/z 524 (intermediate ester). The material was dissolved in a mixture of water (1.6 mL) and 5M NaOH (0.2 mL) and the reaction was stirred for 30 min. The pH was adjusted to 2 with 1M HCl and the product was collected by filtration, washed with water (1 mL) and dried under reduced pressure. This gave 25 mg (18%) of the title compound. [M+H]$^+$ m/z 468; $^1$H NMR (400 MHz, DMSO-d$_6$) δ ppm 12.38 (br. s., 2H), 10.47 (s, 1H), 9.99 (br. s., 1H), 8.75 (d, J=8.1 Hz, 1H), 8.70 (d, J=2.2 Hz, 1H), 8.29 (d, J=2.1 Hz, 1H), 6.12 (br. s., 2H), 5.97 (br. s., 2H), 4.35-4.45 (m, 1H), 3.32 (s, 2H), 2.27-2.38 (m, 2H), 2.03-2.15 (m, 1H), 1.85-1.98 (m, 1H).

Example 20: (2S)-2-({5-[2-(2,4-diamino-6-oxo-1,6-dihydropyrimidin-5-yl)acetamido]-3-methylpyridin-2-yl}formamido)pentanedioic acid

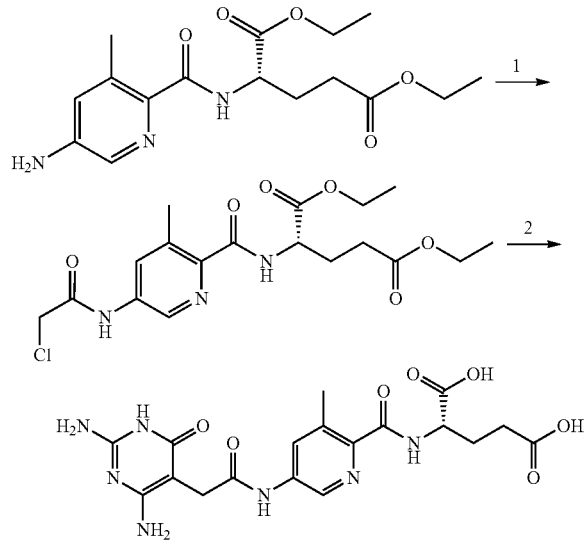

1) 2-Chloroacetyl chloride, Et₃N, DCM, rt; 2) 2,4-Diamino-1H-pyrimidin-6-one, NaHCO₃, NaI, DMF, rt.

Step 1: 1,5-diethyl (2S)-2-{[5-(2-chloroacetamido)-3-methylpyridin-2-yl]formamido}pentanedioate. 2-Chloroacetyl chloride (45.0 μL, 0.57 mmol) was added to a stirred mixture of 1,5-diethyl (2S)-2-[(5-amino-3-methylpyridin-2-yl)formamido]pentanedioate (Intermediate 6, 174 mg, 0.52 mmol), Et₃N (79.0 μL, 0.57 mmol) and DCM (5 mL) at rt. The reaction was stirred for 5 min and the product was washed with diluted Na₂CO₃. The organic phase was dried over Na₂SO₄ and removed under reduced pressure. This gave 160 mg (75%) of the desired intermediate. [M+H]⁺ m/z 414

Step 2: (2S)-2-({5-[2-(2,4-diamino-6-oxo-1,6-dihydropyrimidin-5-yl)acetamido]-3-methylpyridin-2-yl}formamido)pentanedioic acid. 2,6-diamino-3,4-dihydropyrimidin-4-one (53.6 mg, 0.43 mmol), NaHCO₃ (35.7 mg, 0.43 mmol) and NaI (232 mg, 1.55 mmol) was added to a stirred solution of 1,5-diethyl (2S)-2-{[5-(2-chloroacetamido)-3-methylpyridin-2-yl]formamido}pentanedioate (160 mg, 0.39 mmol) in DMF (1 mL). The reaction was stirred in a sealed tube at rt overnight. MeOH (3 mL) and 1M HCl (0.4 mL) was added to the mixture and the product was purified by acidic preparative HPLC. The pure fractions were combined and the solvents were removed under reduced pressure. [M+H]⁺ m/z 504 (intermediate ester). The resulting material was dissolved in a mixture of water (1.6 mL) and 5M NaOH (0.2 mL) and the reaction was stirred for 30 min. The pH was adjusted to ~2 with 1M HCl and the product was collected by filtration, washed with water (1 mL) and dried under reduced pressure. This gave 25 mg (14%) of the title compound. [M+H]⁺ m/z 448; ¹H NMR (400 MHz, DMSO-d₆) δ ppm 12.35 (br. s., 2H), 10.28 (s, 1H), 9.98 (br. s., 1H), 8.67 (dd, J=2.4, 0.3 Hz, 1H), 8.65 (d, J=8.1 Hz, 1H), 7.93 (dd, J=2.3, 0.6 Hz, 1H), 6.10 (br. s., 2H), 5.95 (br. s, 2H), 4.41 (td, J=8.6, 4.8 Hz, 1H), 3.31 (s, 2H), 2.53 (s, 3H), 2.26-2.34 (m, 2H), 2.05-2.16 (m, 1H), 1.89-2.03 (m, 1H).

Example 21: (2S)-2-((5-[2-(2,4-diamino-6-oxo-1,6-dihydropyrimidin-5-yl)acetamido]-6-ethenylpyridin-2-yl)formamido)pentanedioic acid

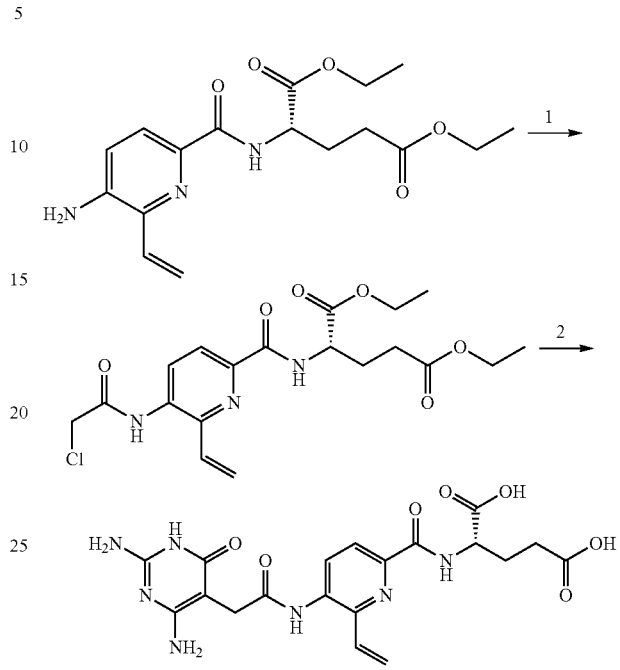

1) 2-Chloroacetyl chloride, Et₃N, DCM, rt; 2) 2,4-Diamino-1H-pyrimidin-6-one, NaHCO₃, NaI, DMF, rt.

Step 1: 1,5-diethyl (2S)-2-{[5-(2-chloroacetamido)-6-ethenylpyridin-2-yl]formamido}pentanedioate. 2-Chloroacetyl chloride (43.0 μL, 0.53 mmol) was added to a stirred mixture of 1,5-diethyl (2S)-2-[(5-amino-6-ethenylpyridin-2-yl)formamido]pentanedioate (Intermediate 5, 155 mg, 0.44 mmol), Et₃N (74.0 μL, 0.57 mmol) and DCM (5 mL) at rt. The reaction was stirred for 5 min and the product was washed with diluted Na₂CO₃. The organic phase was dried over Na₂SO₄ and removed under reduced pressure. This gave 116 mg (61%) of the desired intermediate. [M+H]⁺ m/z 426

Step 2: (2S)-2-({5-[2-(2,4-diamino-6-oxo-1,6-dihydropyrimidin-5-yl)acetamido]-6-ethenylpyridin-2-yl}formamido)pentanedioic acid. 2,6-diamino-3,4-dihydropyrimidin-4-one (37.8 mg, 0.30 mmol), NaHCO₃ (25.2 mg, 0.30 mmol) and NaI (163 mg, 1.09 mmol) was added to a stirred solution of 1,5-diethyl (2S)-2-{[5-(2-chloroacetamido)-6-ethenylpyridin-2-yl]formamido}pentanedioate (116 mg, 0.27 mmol) in DMF (1 mL). The reaction was stirred in a sealed tube at rt overnight. MeOH (3 mL) and 1M HCl (0.4 mL) was added to the mixture and the product was purified by acidic preparative HPLC. The pure fractions were combined and the solvents were removed under reduced pressure. [M+H]⁺ m/z 516 (intermediate ester). The material was dissolved in a mixture of water (1.6 mL) and 5M NaOH (0.2 mL) and the reaction was stirred for 30 min. The pH was adjusted to 2 with 1M HCl and the product was collected by filtration, washed with water (1 mL) and dried under reduced pressure. This gave 11 mg (9%) of the title compound. [M+H]⁺ m/z 460; ¹H NMR (400 MHz, DMSO-d₆) δ ppm 12.42 (br. s., 2H), 10.23 (br. s., 1H), 10.13 (s, 1H), 8.75 (d, J=8.1 Hz, 1H), 8.30 (d, J=8.5 Hz, 1H), 7.89 (d, J=8.4 Hz, 1H), 7.18 (dd, J=16.7, 10.7 Hz, 1H), 6.67 (dd, J=16.7, 2.2 Hz, 1H), 6.15 (br. s., 2H), 6.10 (br. s, 2H), 5.56-5.62 (m, 1H), 4.48 (td, J=8.6, 4.8 Hz, 1H), 3.34 (s, 2H under the water peak), 2.27-2.36 (m, 2H), 2.11-2.23 (m, 1H), 1.97-2.10 (m, 1H).

Example 22: (2S)-2-[(5-{[(2,4-diamino-6-oxo-1,6-dihydropyrimidin-5-yl)carbamoyl]amino}pyridin-2-yl)formamido]butanedioic acid Prepared according to general procedure A from 5-{[(2,4-diamino-6-oxo-1,6-dihydropyrimidin-5-yl)carbamoyl]amino}pyridine-2-carboxylic acid (Intermediate 1.60 mg, 0.20 mmol) and 1,4-dimethyl (2S)-2-aminobutanedioate hydrochloride (58 mg, 0.29 mmol) to generate the title compound as a white solid (10 mg, 12%, 2 steps). LCMS [M+H]$^+$ m/z 421; $^1$H NMR (400 MHz, DMSO-d$_6$) δ ppm 12.55 (br. s, 1H), 10.38 (br. S., 1H), 9.26 (br. S., 1H), 8.63-8.83 (m, 2H), 8.09 (d, J=6.9 Hz, 1H), 7.93 (d, J=8.8 Hz, 1H), 6.93 (br. s., 1H), 6.58 (br. s., 2H), 6.23 (br. s., 2H), 4.78 (dt, J=8.4, 5.6 Hz, 1H), 2.78-2.92 (m, 2H).

Example 23: (2S)-2-[(4S)-4-carboxy-4-[(5-{[(2,4-diamino-6-oxo-1,6-dihydropyrimidin-5-yl)carbamoyl]amino}pyridin-2-yl)formamido]butanamido]pentanedioic acid Prepared according to general procedure A from 5-{[(2,4-diamino-6-oxo-1,6-dihydropyrimidin-5-yl)carbamoyl]amino}pyridine-2-carboxylic acid (Intermediate 1.60 mg, 0.20 mmol) and 1,5-diethyl (2S)-2-[(4S)-4-amino-5-methoxy-5-oxopentanamido]pentanedioate hydrochloride (Intermediate 14, 75 mg, 0.20 mmol) to generate the title compound as a white solid (2 mg, 2%, 2 steps). LCMS [M+H]$^+$ m/z 564; $^1$H NMR (400 MHz, DMSO-d$_6$) δ ppm 12.57 (br. s., 3H), 11.11 (br. s., 1H), 9.40-9.71 (m, 1H), 8.73 (br. s., 1H), 8.61 (d, J=8.2 Hz, 1H), 8.04-8.17 (m, 2H), 7.93 (d, J=8.5 Hz, 1H), 6.59-7.56 (m, 5H), 4.43 (td, J=8.5, 3.9 Hz, 1H), 4.08-4.26 (m, 1H), 2.11-2.31 (m, 5H), 1.86-2.04 (m, 2H), 1.64-1.78 (m, 1H).

Example 24: (2S)-2-[(5-{[(2,4-diamino-6-oxo-1,6-dihydropyrimidin-5-yl)carbamoyl]amino}-3-fluoropyridin-2-yl)formamido]-4-(1H-1,2,3,4-tetrazol-5-yl)butanoic acid Prepared according to general procedure A from methyl (2S)-2-amino-4-[1-(2-cyanoethyl)-1H-1,2,3,4-tetrazol-5-yl]butanoate hydrochloride (Intermediate 2, 45 mg, 0.14 mmol) and 5-{[(2,4-diamino-6-oxo-1,6-dihydropyrimidin-5-yl)carbamoyl]amino}-3-fluoropyridine-2-carboxylic acid (Intermediate 3, 54 mg, 0.19 mmol) to generate the title compound as a white solid (22 mg, 33%, 2 steps). The tetrazole protecting group was removed in the same step as the ester hydrolyzation after stirring at rt for 18 h. LCMS [M+H]$^+$ m/z 477; $^1$H NMR (400 MHz, DMSO-d$_6$) δ ppm 15.98 (br. s., 1H), 12.91 (br. s., 1H), 10.00 (br. s., 1H), 9.49 (br. s., 1H), 8.68 (d, J=8.2 Hz, 1H), 8.38-8.59 (m, 1H), 8.04 (d, J=13.3 Hz, 1H), 6.97 (br. s., 1H), 6.20 (br. s., 2H), 6.00 (br. s., 2H), 4.43-4.52 (m, 1H), 2.84-3.03 (m, 2H), 2.13-2.42 (m, 2H).

Example 25: (2R)-2-[(4S)-4-carboxy-4-[(5-{[(2,4-diamino-6-oxo-1,6-dihydropyrimidin-5-yl)carbamoyl]amino}pyridin-2-yl)formamido]butanamido]pentanedioic acid Prepared according to general procedure A from 5-{[(2,4-diamino-6-oxo-1,6-dihydropyrimidin-5-yl)carbamoyl]amino}pyridine-2-carboxylic acid (Intermediate 1.60 mg, 0.20 mmol) and 1,5-dimethyl (2R)-2-[(4S)-4-amino-5-methoxy-5-oxopentanamido]pentanedioate hydrochloride (Intermediate 13, 80 mg, 0.23 mmol) to generate the title compound as a white solid (11 mg, 10%, 2 steps). LCMS [M+H]$^+$ m/z 564; $^1$H NMR (400 MHz, DMSO-d$_6$) δ ppm 12.51 (br. s., 3H), 10.08 (br. s., 1H), 9.15 (br. s., 1H), 8.71 (br. s., 1H), 8.53-8.64 (m, 1H), 8.03-8.19 (m, 2H), 7.92 (d, J=8.5 Hz, 1H), 6.87 (br. s., 1H), 6.28 (br. s., 2H), 6.02 (br. s., 2H), 4.43 (td, J=8.4, 4.4 Hz, 1H), 4.04-4.26 (m, 1H), 2.07-2.31 (m, 5H), 1.83-2.06 (m, 2H), 1.63-1.78 (m, 1H).

Example 26: (2S)-2-((5-[2-(2,4-diamino-6-oxo-1,6-dihydropyrimidin-5-yl)acetamido]-6-phenoxypyridin-2-yl)formamido)pentanedioic acid

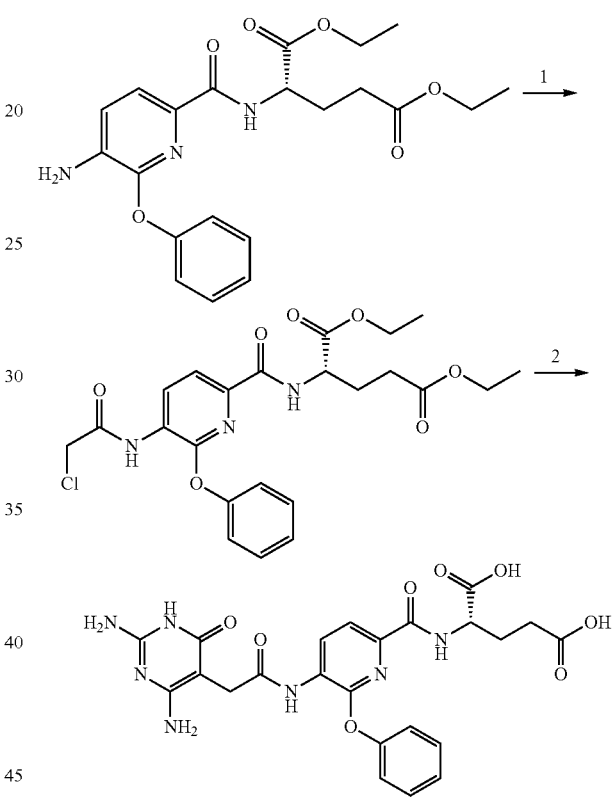

1) 2-Chloroacetyl chloride, Et$_3$N, DCM, rt; 2) 2,4-Diamino-1H-pyrimidin-6-one, NaHCO$_3$, NaI, DMF, rt.

Step 1: 1,5-diethyl (2S)-2-{[5-(2-chloroacetamido)-6-phenoxypyridin-2-yl]formamido}pentanedioate. 2-Chloroacetyl chloride (25.0 µL, 0.32 mmol) was added to a stirred mixture of 1,5-diethyl (2S)-2-{[5-(2-chloroacetamido)-6-phenoxypyridin-2-yl]formamido}pentanedioate (Intermediate 7, 120 mg, 0.29 mmol), Et$_3$N (44.0 µL, 0.32 mmol) and DCM (5 mL) at rt. The reaction was stirred for 5 min and the product was washed with diluted Na$_2$CO$_3$. The organic phase was dried over Na$_2$SO$_4$ and removed under reduced pressure. This gave 95 mg (67%) of the desired intermediate. [M+H]$^+$ m/z 492.

Step 2: (2S)-2-({5-[2-(2,4-diamino-6-oxo-1,6-dihydropyrimidin-5-yl)acetamido]-6-phenoxypyridin-2-yl}formamido)pentanedioic acid. 2,6-diamino-3,4-dihydropyrimidin-4-one (26.8 mg, 0.21 mmol), NaHCO$_3$ (17.9 mg, 0.21 mmol) and NaI (116 mg, 0.77 mmol) was added to a stirred solution of 1,5-diethyl (2S)-2-{[5-(2-chloroacetamido)-6-phenoxypyridin-2-yl]formamido}pentanedioate (95.0 mg, 0.19 mmol) in DMF (1 mL). The reaction was stirred in a sealed tube at rt overnight. MeOH (3 mL) and 1M HCl (0.4 mL) was added to the mixture and the product was purified by acidic preparative HPLC. The pure fractions were combined and the solvents were removed under reduced pressure. [M+H]+ m/z 582 (intermediate ester). The material was dissolved in a mixture of water (1.6 mL) and 5M NaOH (0.2 mL) and the reaction was stirred for 30 min. The pH was adjusted to 2 with 1M HCl and the product was collected by filtration, washed with water (1 mL) and dried under reduced pressure. This gave 11 mg (11%) of the title compound [M+H]+ m/z 526; $^1$H NMR (400 MHz, DMSO-$d_6$) δ ppm 11.82-13.60 (m, 2H), 10.20 (br. s., 1H), 10.15 (s, 1H), 8.77 (d, J=8.2 Hz, 1H), 7.71-7.79 (m, 2H), 7.41-7.48 (m, 2H), 7.32-7.38 (m, 2H), 7.21-7.28 (m, 1H), 6.14 (br. s., 2H), 6.11 (br. s, 2H), 4.35 (td, J=7.9, 5.1 Hz, 1H), 3.38 (s, 2H), 2.10-2.20 (m, 2H), 1.96-2.07 (m, 1H), 1.74-1.86 (m, 1H).

Example 27; (2S)-2-((5-[2-(2,4-diamino-6-oxo-1,6-dihydropyrimidin-5-yl)acetamido]-6-phenylpyridin-2-yl)formamido)pentanedioic acid

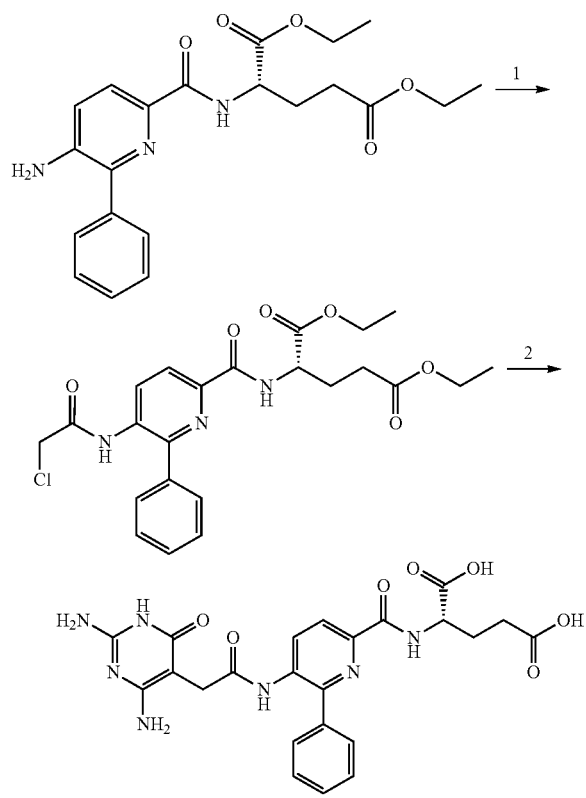

1) 2-Chloroacetyl chloride, Et$_3$N, DCM, rt; 2) 2,4-Diamino-1H-pyrimidin-6-one, NaHCO$_3$, NaI, DMF, rt.

Step 1: 1,5-diethyl (2S)-2-{[5-(2-chloroacetamido)-6-phenylpyridin-2-yl]formamido}pentanedioate. 2-Chloroacetyl chloride (27.0 μL, 0.34 mmol) was added to a stirred mixture of 1,5-diethyl (2S)-2-[(5-amino-6-phenylpyridin-2-yl)formamido]pentanedioate (Intermediate 8, 122 mg, 0.31 mmol), Et$_3$N (47.0 μL, 0.34 mmol) and DCM (5 mL) at rt. The reaction was stirred for 5 min. and the product was washed with diluted Na$_2$CO$_3$. The organic phase was dried over Na$_2$SO$_4$ and removed under reduced pressure. This gave 101 mg (69%) of the desired intermediate. [M+H]+m/z 476.

Step 2: (2S)-2-({5-[2-(2,4-diamino-6-oxo-1,6-dihydropyrimidin-5-yl)acetamido]-6-phenylpyridin-2-yl}formamido)pentanedioic acid. 2,6-diamino-3,4-dihydropyrimidin-4-one (29.4 mg, 0.23 mmol), NaHCO$_3$ (19.6 mg, 0.23 mmol) and NaI (127 mg, 0.85 mmol) was added to a stirred solution of 1,5-diethyl (2S)-2-{[5-(2-chloroacetamido)-6-phenylpyridin-2-yl]formamido}pentanedioate (101 mg, 0.21 mmol) in DMF (1 mL). The reaction was stirred in a sealed tube at rt overnight. MeOH (3 mL) and 1M HCl (0.4 mL) was added to the mixture and the product was purified by acidic preparative HPLC. The pure fractions were combined and the solvents were removed under reduced pressure. [M+H]+ m/z 566 (Intermediate ester). The material was dissolved in a mixture of water (1.6 mL) and 5M NaOH (0.2 mL) and the reaction was stirred for 30 min. The pH was adjusted to 2 with 1M HCl and the product was collected by filtration, washed with water (0.5 mL). 1 Drop HCl was added to the filtrate and more product was collected. The materials were dried under vacuum. This gave 11 mg (10%) of the title compound. [M+H]+ m/z 510; $^1$H NMR (400 MHz, DMSO-$d_6$) δ ppm 12.30 (br. s., 2H), 9.94 (br. s., 1H), 8.97 (s, 1H), 8.71 (d, J=8.5 Hz, 1H), 8.58 (d, J=8.4 Hz, 1H), 8.00 (d, J=8.5 Hz, 1H), 7.57-7.63 (m, 2H), 7.42-7.52 (m, 3H), 6.15 (br. s., 2H), 6.03 (br. s, 2H), 4.49 (td, J=8.6, 4.9 Hz, 1H), 3.20 (s, 2H), 2.23-2.33 (m, 2H), 2.09-2.20 (m, 1H), 1.92-2.05 (m, 1H).

Example 28: (2S)-2-[(4S)-4-carboxy-4-({5-[2-(2,4-diamino-6-oxo-1,6-dihydropyrimidin-5-yl)acetamido]pyridin-2-yl}formamido)butanamido]pentanedioic acid HATU (105 mg, 0.276 mmol) was added to a stirred mixture of 5-[2-(2,4-diamino-6-oxo-1,6-dihydropyrimidin-5-yl)acetamido]pyridine-2-carboxylic acid (Intermediate 9, 70 mg, 0.23 mmol), 1,5-diethyl (2S)-2-[(4S)-4-amino-5-methoxy-5-oxopentanamido]pentanedioate hydrochloride (Intermediate 14, 96.9 mg, 0.25 mmol), Et$_3$N (0.193 mL, 1.39 mmoL) and DMSO (2 mL). The reaction was stirred in a sealed tube at rt for 2 h. MeOH (2 mL) and 12M HCl (0.2 mL) was added and the product was purified by acidic preparative HPLC. The pure fractions were combined and the solvents were removed under reduced pressure. [M+H]+ m/z 633 (intermediate ester). The material was dissolved in a mixture of water (1.5 mL) and 5M NaOH (0.3 mL) and the reaction was stirred for 30 min. The pH was adjusted to 2 with 1M HCl and the product was collected by filtration, washed with water (0.3 mL) and dried under reduced pressure and in a vacuum oven (40° C. overnight). This gave 20 mg (13%) of the title compound. [M+H]+ m/z 563; $^1$H NMR (400 MHz, DMSO-$d_6$) δ ppm 12.56 (br. s., 2H), 10.43 (s, 1H), 10.07 (br. s., 1H), 8.82-8.88 (m, 1H), 8.67 (d, J=7.9 Hz, 1H), 8.19 (dd, J=8.7, 2.4 Hz, 1H), 8.10 (d, J=7.7 Hz, 1H), 7.94-8.01 (m, 1H), 6.16 (br. s., 2H), 5.95 (br. s, 2H), 4.39 (td, J=8.3, 4.3 Hz, 1H), 4.11-4.21 (m, 1H), 3.32 (s, 2H), 2.06-2.30 (m, 5H), 1.85-2.04 (m, 2H), 1.66-1.80 (m, 1H).

Example 29: (2S)-2-({5-[2-(2,4-diamino-6-oxo-1,6-dihydropyrimidin-5-yl)acetamido]-6-methoxypyridin-2-yl}formamido)pentanedioic acid

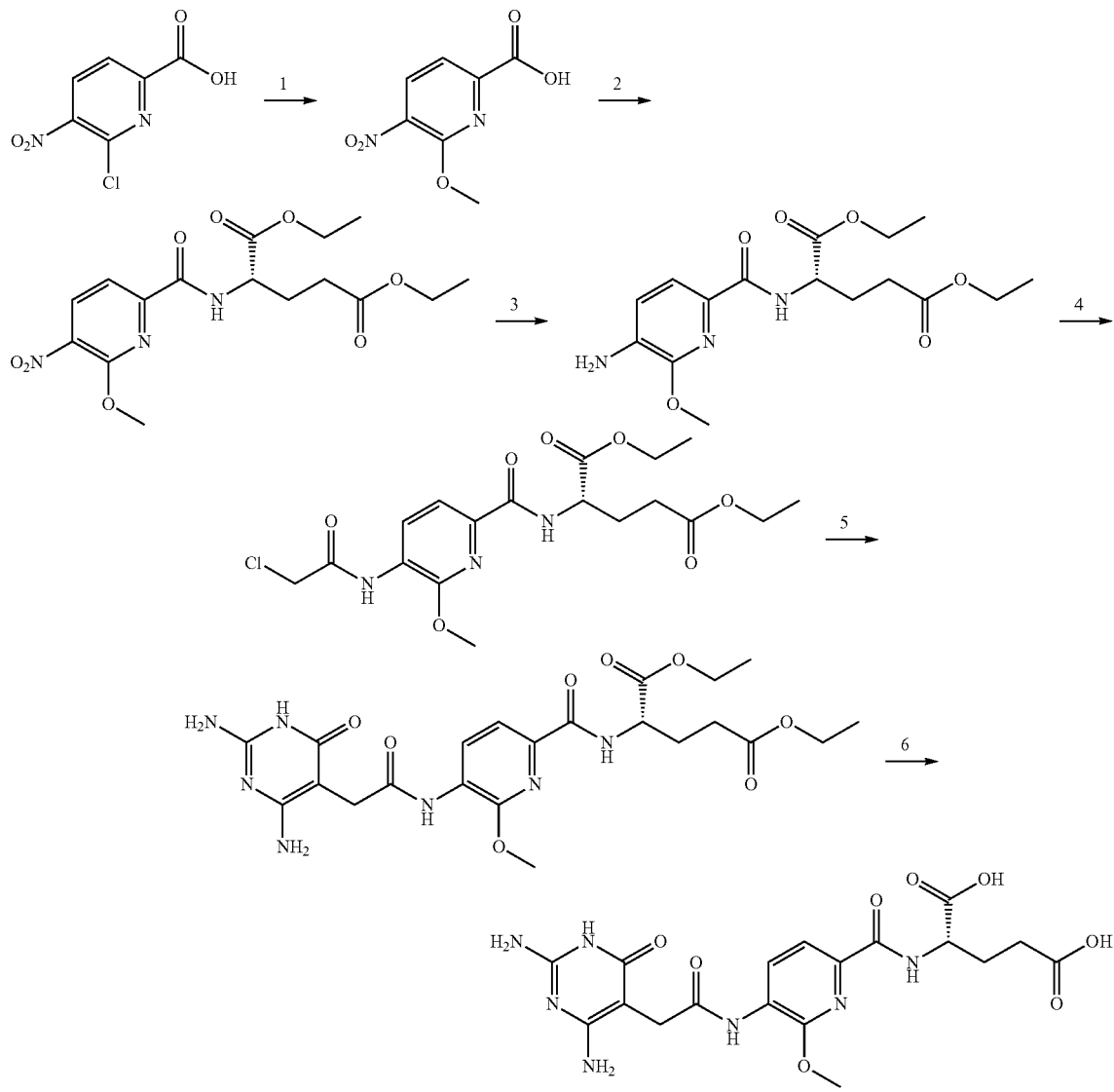

1) NaOMe, NaI, rt; 2) 1,5-diethyl (2S)-2-aminopentanedioate·HCl, TBTU, Et₃N, THF, rt; 3) SnCl₂·2H₂O, EtOH, 90° C.; 4) 2-Chloroacetyl chloride, Et₃N, DCM, rt; 5) 2,4-diamino-1H-pyrimidin-6-one, NaHCO₃, NaI, DMF, rt; 6) 1N NaOH, rt.

Step 1: 6-methoxy-5-nitropyridine-2-carboxylic acid. In a reaction tube under N₂ atmosphere 6-chloro-5-nitropyridine-2-carboxylic acid (150 mg, 0.74 mmol) was dissolved in MeOH (3 mL) and 25 wt % NaOMe in MeOH (50 µL, 2.2 mmol) was added. The resulting mixture was stirred at rt for 12 h. The reaction was monitored by LCMS and after completion, the volatiles were removed and the residue was diluted with water (20 mL), sat NaHCO₃ (5 mL) and EtOAc (25 mL). The organic layer was separated and discarded. The aq layer was acidified using 1N HCl (pH 4-5) and then extracted with DCM (3×30 mL). The combined organic layer was washed with brine (10 mL), dried (Na₂SO₄), and concentrated to provide crude compound which was used in the next step without purification. Yield 130 mg (88%). LCMS [M+H]⁺ m/z 199.

Step 2: 1,5-diethyl (2S)-2-[(6-methoxy-5-nitropyridin-2-yl)formamido]pentanedioate. 6-Methoxy-5-nitropyridine-2-carboxylic acid (130 mg, 0.66 mmol), Et₃N (146 mg, 1.9 mmol) and TBTU (321 mg, 0.984 mmol) were dissolved in THF (4 mL). The reaction mixture was stirred at rt for 10 min. 1,5-Diethyl (2S)-2-aminopentanedioate-HCl (236 mg, 0.94 mmol) was added and stirring was continued overnight. After completion of the reaction, the volatiles were removed and the residue was diluted with water and extracted with DCM (3×30 mL). The combined organic phases were dried over Na₂SO₄ and evaporated to offer crude product which was used without purification in the next step. Yield 180 mg (71%). LCMS [M+H]⁺ m/z 384.

Step 3: 1,5-diethyl 2-[(5-amino-6-cyclopropoxypyridin-2-yl)formamido]pentanedioate. SnCl₂.2H₂O (634 mg, 2.8 mmol) was added into a solution of 1,5-diethyl (2S)-2-[(6-methoxy-5-nitropyridin-2-yl)formamido]pentanedioate (180 mg, 0.47 mmol) in EtOH (10 mL). The reaction mixture was heated to 90° C. for 1 h. After completion, the mixture was cooled to rt and the volatiles were removed. The residue was then diluted with water (10 mL) and DCM (20 mL). Sat NaHCO$_3$ was added until the solution turned basic (pH 8-9). The precipitate was filtered and the layers were separated. The aq layer was further extracted with DCM (2×20 mL). The combined organic layers was washed with brine and were dried (Na$_2$SO$_4$) and concentrated under reduced pressure to provide crude product which was purified by flash column chromatography (silica gel, 5% DCM in MeOH) to offer pure product as off-white solid. Yield 120 mg (72%). LCMS [M+H]$^+$ m/z 354.

Step 4: 1,5-diethyl (2S)-2-{[5-(2-chloroacetamido)-6-methoxypyridin-2-yl]formamido}pentanedioate. 2-Chloroacetyl chloride (42 mg, 0.37 mmol) was added to a stirred mixture of 1,5-diethyl (2S)-2-[(5-amino-6-cyclopropoxy-pyridin-2-yl)formamido]pentanedioate (120 mg, 0.34 mmol), Et$_3$N (41 mg, 0.41 mmol) and DCM (4 mL) at rt. The reaction was stirred for 5 min and the product was washed with dilute NaHCO$_3$. The organic phase was dried over Na$_2$SO$_4$ and removed under reduced pressure to provide crude product which was used without purification in the next step. Yield 140 mg (95%), [M+H]$^+$ m/z 430.

Step 5: 1,5-diethyl (2S)-2-({5-[2-(2,4-diamino-6-oxo-1,6-dihydropyrimidin-5-yl)acetamido]-6-methoxypyridin-2-yl}formamido)pentanedioate. 2,4-Diamino-1H-pyrimidin-6-one (45 mg, 0.36 mmol), NaHCO$_3$ (30 mg, 0.36 mmol) and NaI (193 mg, 1.3 mmol) was added to a stirred solution of 1,5-diethyl (2S)-2-{[5-(2-chloroacetamido)-6-methoxy-pyridin-2-yl]formamido}pentanedioate (140 mg, 0.32 mmol) in DMF (1 mL). The reaction was stirred in a sealed tube at rt overnight. MeOH (3 mL) and 1M HCl (0.4 mL) were added to the mixture and the product was purified by acidic preparative HPLC. The pure fractions were combined and the solvents were removed to give pure product. Yield 96 mg (56%), [M+H]$^+$ m/z 520.

Step 6: (2S)-2-({5-[2-(2,4-diamino-6-oxo-1,6-dihydropyrimidin-5-yl)acetamido]-6-methoxypyridin-2-yl}formamido)pentanedioic acid. To the reaction vial 1,5-diethyl (2S)-2-({5-[2-(2,4-diamino-6-oxo-1,6-dihydropyrimidin-5-yl)acetamido]-6-methoxypyridin-2-yl}formamido)pentanedioate (0.096 g, 0.19 mmol) was suspended in water (1 mL) and a 1N NaOH (1.1 mL, 1.1 mmol) was added. The mixture was stirred at rt for 30 min. 1N HCl was added until the solution turned acidic (pH 3-4) and the mixture was stirred for a further 30 min before the precipitate was collected by filtration. The solid was sequentially washed with water (2 mL) and CH$_3$CN (4 mL). After drying, the title compound was obtained. Yield 45 mg (52%), [M+H]$^+$ m/z 464; $^1$H NMR (400 MHz, DMSO-d$_6$) δ ppm 12.50 (br. s., 1H), 10.20 (br. s., 1H), 9.66 (s, 1H), 8.59 (d, J=8.2 Hz, 1H), 8.46 (d, J=8.2 Hz, 1H), 7.60 (d, J=7.9 Hz, 1H), 6.15 (br. s. 2H), 6.07 (br. s., 2H), 4.44 (td, J=8.5, 4.9 Hz, 1H), 4.05 (s, 3H), 3.34 (s, 2H), 2.27-2.36 (m, 2H), 2.09-2.20 (m, 1H), 1.96-2.06 (m, 1H).

Example 30: (2S)-2-((5-[2-(2,4-diamino-6-oxo-1,6-dihydropyrimidin-5-yl)acetamido]-3-(trifluoromethyl)pyridin-2-yl)formamido)pentanedioic acid

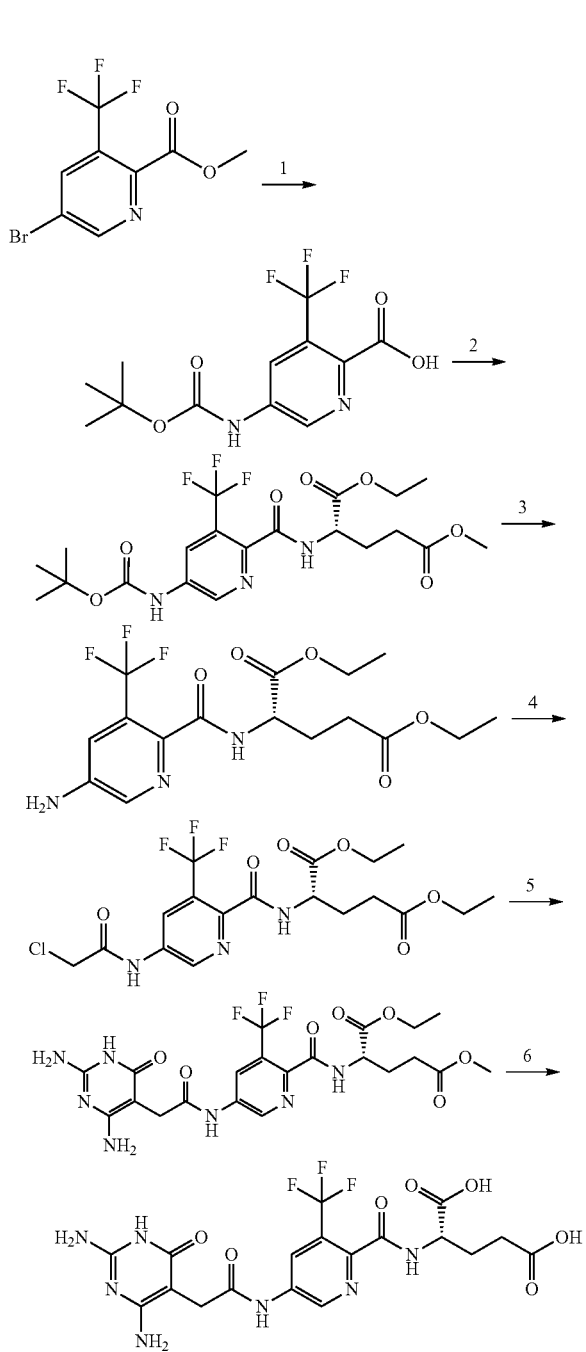

1) (i) tert-Butyl carbamate, Cs$_2$CO$_3$, XPhos, Pd(OAc)$_2$, dioxane, 90° C.;
(ii) 1N NaOH, rt; 2) 1,5-diethyl (2S)-2-aminopentanedioate•HCl, TBTU, Et$_3$N, THF, rt; 3) DCM, TFA, rt; 4) 2-chloroacetyl chloride, Et$_3$N, DCM, rt; 5) 2,4-diamino-1H-pyrimidin-6-one, NaHCO$_3$, NaI, DMF, rt; 6) 1N NaOH, rt.

Step 1: 5-{[(tert-butoxy)carbonyl]amino}-3-(trifluoromethyl)pyridine-2-carboxylic acid. In a sealed tube under N$_2$ atmosphere methyl 5-bromo-3-(trifluoromethyl)pyridine-2-carboxylate (250 mg, 0.64 mmol), t-butyl carbamate (123 mg, 0.77 mmol), dry powdered Cs$_2$CO$_3$ (344 mg, 0.77 mmol), XPhos (40 mg, 0.06 mmol), and Pd(OAc)$_2$ (9 mg, 0.03 mmol). Dry dioxane (4 mL) was then added and the mixture was heated to 90° C. for 3 h. The reaction was monitored by LCMS and after the complete consumption of aryl bromide heating discontinued and the reaction mixture was allowed cool to rt. 1N NaOH (3 mL) was then added and stirring continued for an additional h. The reaction mixture was then diluted with water and EtOAc (25 mL). The organic layer was separated and discarded. The aq layer was acidified using 1N HCl (pH 4-5) and then extracted with DCM (3×30 mL). The combined organic layer was washed with brine (10 mL), dried ($Na_2SO_4$), and concentrated to provide crude product which was used in the next step without purification. Yield 226 mg (83%). LCMS [M+H]$^+$ m/z 307.

Step 2: 1,5-diethyl (2S)-2-{[5-nitro-3-(trifluoromethyl) pyridin-2-yl]formamido}pentanedioate. 5-{[(Tert-butoxy) carbonyl]amino}-3-(trifluoromethyl)pyridine-2-carboxylic acid (226 mg, 0.74 mmol), triethylamine (164 mg, 2.2 mmol) and TBTU (361 mg, 1.1 mmol) were dissolved in THF (4 mL). The reaction mixture was stirred at rt for 10 min. 1,5-diethyl (2S)-2-aminopentanedioate-HCl (265 mg, 1.1 mmol) was added and stirring was continued overnight. After completion of the reaction, the volatiles were removed and the residue was diluted with water and extracted with DCM (3×30 mL). The combined organic phases were dried over $Na_2SO_4$ and evaporated to offer crude product which was used without purification in the next step. Yield 328 mg (90%). LCMS [M+H]$^+$ m/z 492.

Step 3: 1,5-diethyl (2S)-2-{[5-amino-3-(trifluoromethyl) pyridin-2-yl]formamido}pentanedioate. The crude residue of 1,5-diethyl (2S)-2-{[5-nitro-3-(trifluoromethyl)pyridin-2-yl]formamido}pentanedioate (328 mg, 0.67 mmol) was dissolved in 1:1 DCM:TFA (5 mL) and stirred at rt for 1 h. The resulting mixture was concentrated under reduced pressure and partitioned between sat aq $NaHCO_3$ (until pH 8-9) and DCM (40 mL). The layers were separated and the organic layer was washed with brine (10 mL), dried ($Na_2SO_4$), concentrated, and purified by silica gel chromatography (6% MeOH in DCM) to provide pure product as white solid. Yield 250 mg (95%). LCMS [M+H]$^+$ m/z 392.

Step 4: 1,5-diethyl (2S)-2-{[5-(2-chloroacetamido)-3-(trifluoromethyl)pyridin-2-yl]formamido}pentanedioate. 2-Chloroacetyl chloride (87 mg, 0.77 mmol) was added to a stirred mixture of 1,5-diethyl (2S)-2-{[5-amino-3-(trifluoromethyl)pyridin-2-yl]formamido}pentanedioate (250 mg, 0.64 mmol), $Et_3N$ (77 mg, 0.77 mmol) and DCM (5 mL) at rt. The reaction was stirred for 5 min. and the product was washed with diluted $NaHCO_3$. The organic phase was dried over $Na_2SO_4$ and removed under reduced pressure to provide crude product which was used without purification in the next step. Yield 290 mg (96%). LCMS [M+H]$^+$ m/z 468.

Step 5: 1,5-diethyl (2S)-2-({5-[2-(2,4-diamino-6-oxo-1,6-dihydropyrimidin-5-yl)acetamido]-3-(trifluoromethyl)pyridin-2-yl}formamido)pentanedioate. 2,4-Diamino-1H-pyrimidin-6-one (86 mg, 0.68 mmol), $NaHCO_3$ (57 mg, 0.68 mmol) and NaI (367 mg, 2.5 mmol) was added to a stirred solution of 1,5-diethyl (2S)-2-{[5-(2-chloroacetamido)-3-(trifluoromethyl)pyridin-2-yl]formamido}pentanedioate (290 mg, 0.62 mmol) in DMF (1 mL). The reaction was stirred in a sealed tube at rt overnight. MeOH (3 mL) and 1M HCl (0.4 mL) were added to the mixture and the product was purified by acidic preparative HPLC. The pure fractions were combined and the solvents were removed to offer pure product as white solid. Yield 160 mg (46%). LCMS [M+H]$^+$ m/z 558.

Step 6: (2S)-2-({5-[2-(2,4-diamino-6-oxo-1,6-dihydropyrimidin-5-yl)acetamido]-3-(trifluoromethyl)pyridin-2-yl}formamido)pentanedioic acid. To the reaction vial 1,5-diethyl (2S)-2-({5-[2-(2,4-diamino-6-oxo-1,6-dihydropyrimidin-5-yl)acetamido]-3-(trifluoromethyl) pyridin-2-yl}formamido)pentanedioate (0.160 g, 0.28 mmol) was suspended in water (1 mL) and 1N NaOH (1.72 mL, 1.7 mmol) was added. The mixture was stirred at rt for 30 min. 1N HCl was added until the solution turned acidic (pH 3-4) and the mixture was stirred for a further 30 min before the precipitate was collected by filtration. The solid was sequentially washed with water (2 mL) and $CH_3CN$ (4 mL). After drying, the title compound was obtained. Yield 78 mg (54%). LCMS [M+H]$^+$ m/z 502; $^1$H NMR (400 MHz, DMSO-$d_6$) δ ppm 12.45 (br. s., 1H), 10.56 (s, 1H), 9.96 (br. s., 1H), 8.98 (d, J=2.2 Hz, 1H), 8.83 (d, J=7.9 Hz, 1H), 8.57 (d, J=2.2 Hz, 1H), 6.09 (br. s., 2H), 5.95 (br. s., 2H), 4.33-4.47 (m, 1H), 3.34 (s, 2H), 2.26-2.37 (m, 2H), 2.00-2.15 (m, 1H), 1.82-1.98 (m, 1H).

Example 31: (2S)-2-[(5-{[(2,4-diamino-6-oxo-1,6-dihydropyrimidin-5-yl)carbamoyl]amino}-3-fluoro-pyridin-2-yl)formamido]-3-methylbutanoic acid Prepared according to general procedure A from Intermediate 3. 5-{[(2,4-diamino-6-oxo-1,6-dihydropyrimidin-5-yl) carbamoyl]amino}-3-fluoropyridine-2-carboxylic acid (Intermediate 3) (72 mg; 0.223 mmol) was suspended in DMSO (2 mL) then sonicated for ca 1 h The fine suspension was treated with a solution of Hunig's base (193 µL; 1.12 mmol), EDCl (64 mg; 0.33 mmol), HOBt (45 mg; 0.334 mmol) and methyl (2S)-2-amino-3-methylbutanoate hydrochloride (52 mg; 0.297 mmol) in DMSO (1 mL) and then stirred overnight at room temperature. The resulting solution was filtered and the product purified by preparative HPLC to obtain methyl (2S)-2-[(5-{[(2,4-diamino-6-oxo-1,6-dihydropyrimidin-5-yl)carbamoyl]amino}-3-fluoropyridin-2-yl) formamido]-3-methylbutanoate as a colourless solid which was dissolved in 1M NaOH(aq) (1.2 mL) and stirred at room temperature for 2 h. The pH of the mixture was then adjusted by treatment with 2 M HCl(aq). The precipitated solid was filtered and washed with water (1 mL) to give the title compound. Yield 39 mg (42%). LCMS [M+H]+ m/z 423; $^1$H NMR (400 MHz, DMSO-$d_6$) δ ppm 12.95 (br s, 1H), 10.00 (br s, 1H), 8.45 (br s, 1H), 8.26 (d, J=7.7 Hz, 1H), 8.08 (d, J=14.7 Hz, 1H), 7.35-6.86 (br m, 2H), 6.20 (s, 2H), 5.97 (s, 2H), 4.33 (m, 1H), 2.20 (m, 1H), 0.93 (m, 6H).

Example 32; (2S)-2-((5-[2-(2,4-diamino-6-oxo-1,6-dihydropyrimidin-5-yl)acetamido]-3-fluoropyridin-2-yl)formamido)-4-(1H-1,2,3,4-tetrazol-5-yl)butanoic acid 5-{[(2,4-diamino-6-oxo-1,6-dihydropyrimidin-5-yl)carbamoyl]amino}pyridine-2-carboxylic acid (Intermediate 15, 60 mg, 0.19 mmol), methyl (2S)-2-amino-4-[1-(2-cyanoethyl)-1H-1,2,3,4-tetrazol-5-yl]butanoate hydrochloride (Intermediate 2 54 mg, 0.20 mmol) and Hünigs base (0.20 mL, 0.93 mmol) were dissolved in DMSO (2 mL). EDCl (54 mg, 0.28 mmol) and HOBt (38 mg, 0.28 mmol) were added and the reaction mixture was stirred at rt over night. MeOH (1 mL) was added and the mixture was purified with acidic preparative HPLC to obtain the intermediate ester. 1M NaOH (1 mL) and water (2 mL) was added to the material and the reaction was stirred for 1 hour at 35° C. 2M HCl was added until pH 2. The product was collected by filtration and washed with water (3 mL) to generate the title compound as a white solid (36 mg, 40%). LCMS [M+H]+ 476; 1H NMR (400 MHz, DMSO-$d_6$) δ ppm 16.00 (br. s., 1H), 12.91 (br.

s., 1H), 10.61 (s, 1H), 10.00 (br. s., 1H), 8.77 (d, J=8.1 Hz, 1H), 8.59-8.64 (m, 1H), 8.11 (dd, J=13.4, 1.9 Hz, 1H), 6.13 (br. s., 2H), 5.98 (br. s., 2H), 4.42-4.51 (m, 1H), 3.33 (s, 2H), 2.90-3.01 (m, 2H), 2.31-2.43 (m, 1H), 2.17-2.30 (m, 1H).

Example 33: (2S)-2-((5-[2-(2,4-diamino-6-oxo-1,6-dihydropyrimidin-5-yl)acetamido]-3-fluoropyridin-2-yl)formamido)-3-phenylpropanoic acid HATU (40 mg, 0.11 mmol) was added to a stirred mixture of 5-[2-(2,4-diamino-6-oxo-1,6-dihydropyrimidin-5-yl)acetamido]-3-fluoropyridine-2-carboxylic acid (Intermediate 15, 26 mg, 0.081 mmol), methyl (2S)-2-amino-3-phenylpropanoate hydrochloride (21 mg, 0.097 mmol), Et$_3$N (0.045 mL, 0.32 mmol) and DMSO (2 mL). The reaction was stirred in a sealed tube for 2 hours at rt. The intermediate ester was purified by acidic preparative HPLC. The pure fractions were combined and the solvents were removed in a rotavapor. LCMS [M+H]$^+$ m/z 484. The material was dissolved in a mixture of water (1 mL) and 5M NaOH (0.2 mL) and the reaction was stirred for 5 min. at rt. The pH was adjusted to 2 with 1M HCl and the product was collected by filtration, washed with water (1 mL) and MeCN (0.2 mL) and dried in a vacuum oven (40° C.) over night. This gave 16 mg (42%) of the title compound. LCMS [M+H]$^+$ m/z 470; $^1$H NMR (400 MHz, DMSO-d$_6$) δ ppm 12.98 (br. s., 1H), 10.69 (s, 1H), 10.18 (br. s., 1H), 8.57-8.61 (m, 1H), 8.54 (d, J=8.2 Hz, 1H), 8.10 (dd, J=13.5, 2.0 Hz, 1H), 7.15-7.30 (m, 5H), 6.35 (br. s., 2H), 6.07 (br. s., 2H), 4.61-4.70 (m, 1H), 3.34 (s, 2H), 3.10-3.23 (m, 2H).

Example 34: (2S)-2-((5-[2-(2,4-diamino-6-oxo-1,6-dihydropyrimidin-5-yl)acetamido]-3-fluoropyridin-2-yl)formamido)-3-methylbutanoic acid HATU (41 mg, 0.11 mmol) was added to a stirred mixture of 5-[2-(2,4-diamino-6-oxo-1,6-dihydropyrimidin-5-yl)acetamido]-3-fluoropyridine-2-carboxylic acid (Intermediate 15, 27 mg, 0.084 mmol), methyl (2S)-2-amino-3-methylbutanoate hydrochloride (17 mg, 0.10 mmol), Et$_3$N (0.047 mL, 0.34 mmol) and DMSO (2 mL). The reaction was stirred in a sealed tube for 3 hours at rt. The intermediate ester was purified by acidic preparative HPLC. The pure fractions were combined and the solvents were removed in a rotavapor. LCMS [M+H]$^+$ m/z 436. The material was dissolved in a mixture of water (1 mL) and 5M NaOH (0.2 mL) and the reaction was stirred for 5 min. at rt. The pH was adjusted to ~2 with 1M HCl and the product was collected by filtration, washed with water (1 mL) and MeCN (0.2 mL) and dried in a vacuum oven (40° C.) over night. This gave 6 mg (17%) of the title compound. LCMS [M+H]$^+$ m/z 422; $^1$H NMR (400 MHz, DMSO-d$_6$) δ ppm 12.93 (br. s., 1H), 10.63 (s, 1H), 10.01 (br. s., 1H), 8.55-8.60 (m, 1H), 8.32 (d, J=8.7 Hz, 1H), 8.14 (dd, J=13.4, 1.9 Hz, 1H), 6.14 (br. s., 2H), 5.99 (br. s., 2H), 4.33 (dd, J=8.6, 5.4 Hz, 1H), 3.33 (s, 2H), 2.12-2.26 (m, 1H), 0.86-0.98 (m, 6H).

Example 35: (2S)-2-[(5-{[(2,4-diamino-6-oxo-1,6-dihydropyrimidin-5-yl)carbamoyl]amino}-3-fluoropyridin-2-yl)formamido]-3-phenylpropanoic acid HATU (59 mg, 0.16 mmol) was added to a stirred mixture of 5-{[(2,4-diamino-6-oxo-1,6-dihydropyrimidin-5-yl)carbamoyl]amino}-3-fluoropyridine-2-carboxylic acid (Intermediate 3, 50 mg, 0.16 mmol), methyl (2S)-2-amino-3-phenylpropanoate hydrochloride (40 mg, 0.19 mmol), Et$_3$N (0.086 mL, 0.62 mmol) and DMSO (2 mL). The reaction was stirred in a sealed tube for 3 hours at rt. The intermediate ester was purified by acidic preparative HPLC. The pure fractions were combined and the solvents were removed in a rotavapor. LCMS [M+H]$^+$ m/z 485. The material was dissolved in a mixture of water (1 mL) and 5M NaOH (0.2 mL) and the reaction was stirred for 5 min. at rt. The pH was adjusted to 2 with 1M HCl and the product was collected by filtration, washed with water (1 mL) and dried in a vacuum oven (40° C.) over night. This gave 5 mg (7%) of the title compound. LCMS [M+H]$^+$ m/z 471; $^1$H NMR (400 MHz, DMSO-d$_6$) δ ppm 12.96 (br. s., 1H), 10.00 (br. s., 1H), 9.55 (br. s., 1H), 8.31-8.55 (m, 2H), 8.01 (d, J=13.7 Hz, 1H), 7.14-7.31 (m, 5H), 6.99 (br. s., 1H), 6.21 (br. s., 2H), 5.97 (br. s., 2H), 4.65 (td, J=7.9, 5.5 Hz, 1H), 3.09-3.23 (m, 2H).

TABLE 1

Chemical name and structural formula of Examples 1-35.

| Ex. | Chemical Name | Structural formula |
| --- | --- | --- |
| 1 | (2S)-2-[(5-{[(2,4-diamino-6-oxo-1,6-dihydropyrimidin-5-yl)carbamoyl]amino}pyridin-2-yl)formamido]pentanedioic acid | |
| 2 | (2S)-2-[(5-{[(2,4-diamino-6-oxo-1,6-dihydropyrimidin-5-yl)carbamoyl]amino}pyridin-2-yl)formamido]-3-phenylpropanoic acid | |

TABLE 1-continued

Chemical name and structural formula of Examples 1-35.

| Ex. | Chemical Name | Structural formula |
|---|---|---|
| 3 | (2S)-2-[(5-{[(2,4-diamino-6-oxo-1,6-dihydropyrimidin-5-yl)carbamoyl]amino}pyridin-2-yl)formamido]-3-methylbutanoic acid | |
| 4 | (2S)-2-[(5-{[(2,4-diamino-6-oxo-1,6-dihydropyrimidin-5-yl)carbamoyl]amino}pyridin-2-yl)formamido]-4-(1H-1,2,3,4-tetrazol-5-yl)butanoic acid | |
| 5 | (2S)-2-[(3-chloro-5-{[(2,4-diamino-6-oxo-1,6-dihydropyrimidin-5-yl)carbamoyl]amino}pyridin-2-yl)formamido]pentanedioic acid | |
| 6 | (2S)-2-[(5-{[(2,4-diamino-6-oxo-1,6-dihydropyrimidin-5-yl)carbamoyl]amino}-3-fluoropyridin-2-yl)formamido]pentanedioic acid | |
| 7 | (2S)-2-({5-[2-(2,4-diamino-6-oxo-1,6-dihydropyrimidin-5-yl)acetamido]pyridin-2-yl}formamido)pentanedioic acid hydrochloride | |
| 8 | (2S)-2-({5-[2-(2,4-diamino-6-oxo-1,6-dihydropyrimidin-5-yl)acetamido]pyridin-2-yl}formamido)-3-phenylpropanoic acid | |

TABLE 1-continued

Chemical name and structural formula of Examples 1-35.

| Ex. | Chemical Name | Structural formula |
|---|---|---|
| 9 | (2S)-2-({5-[2-(2,4-diamino-6-oxo-1,6-dihydropyrimidin-5-yl)acetamido]pyridin-2-yl}formamido)-4-(1H-1,2,3,4-tetrazol-5-yl)butanoic acid | |
| 10 | (2S)-2-({5-[2-(2,4-diamino-6-oxo-1,6-dihydropyrimidin-5-yl)acetamido]-3-fluoropyridin-2-yl}formamido)pentanedioic acid | |
| 11 | (2S)-3-cyclopentyl-2-[(5-{[(2,4-diamino-6-oxo-1,6-dihydropyrimidin-5-yl)carbamoyl]amino}pyridin-2-yl)formamido]propanoic acid | |
| 12 | (2S)-2-cyclohexyl-2-[(5-{[(2,4-diamino-6-oxo-1,6-dihydropyrimidin-5-yl)carbamoyl]amino}pyridin-2-yl)formamido]acetic acid | |
| 13 | (2S)-2-({5-[2-(2,4-diamino-6-oxo-1,6-dihydropyrimidin-5-yl)acetamido]pyridin-2-yl}formamido)-3-methylbutanoic acid | |
| 14 | (2S)-2-[(5-{[(2,4-diamino-6-oxo-1,6-dihydropyrimidin-5-yl)carbamoyl]amino}pyridin-2-yl)formamido]-4-phenylbutanoic acid | |

TABLE 1-continued

Chemical name and structural formula of Examples 1-35.

| Ex. | Chemical Name | Structural formula |
|---|---|---|
| 15 | (2S)-2-[(5-{[(2,4-diamino-6-oxo-1,6-dihydropyrimidin-5-yl)carbamoyl]amino}pyridin-2-yl)formamido]-2-phenylacetic acid | |
| 16 | (2S)-4-[(benzenesulfonyl)carbamoyl]-2-[(5-{[(2,4-diamino-6-oxo-1,6-dihydropyrimidin-5-yl)carbamoyl]amino}pyridin-2-yl)formamido]butanoic acid | |
| 17 | (2S)-2-[(5-{[(2,4-diamino-6-oxo-1,6-dihydropyrimidin-5-yl)carbamoyl]amino}pyridin-2-yl)formamido]hexanedioic acid | |
| 18 | (2S)-2-[(6-cyclopropoxy-5-{[(2,4-diamino-6-oxo-1,6-dihydropyrimidin-5-yl)carbamoyl]amino}pyridin-2-yl)formamido]pentanedioic acid | |
| 19 | (2S)-2-({3-chloro-5-[2-(2,4-diamino-6-oxo-1,6-dihydropyrimidin-5-yl)acetamido]pyridin-2-yl}formamido)pentanedioic acid | |
| 20 | (2S)-2-({5-[2-(2,4-diamino-6-oxo-1,6-dihydropyrimidin-5-yl)acetamido]-3-methylpyridin-2-yl}formamido)pentanedioic acid | |

TABLE 1-continued

Chemical name and structural formula of Examples 1-35.

| Ex. | Chemical Name | Structural formula |
| --- | --- | --- |
| 21 | (2S)-2-({5-[2-(2,4-diamino-6-oxo-1,6-dihydropyrimidin-5-yl)acetamido]-6-ethenylpyridin-2-yl}formamido)pentanedioic | |
| 22 | (2S)-2-[(5-{[(2,4-diamino-6-oxo-1,6-dihydropyrimidin-5-yl)carbamoyl]amino}pyridin-2-yl)formamido]butanedioic acid | |
| 23 | (2S)-2-[(4S)-4-carboxy-4-[(5-{[(2,4-diamino-6-oxo-1,6-dihydropyrimidin-5-yl)carbamoyl]amino}pyridin-2-yl)formamido]butanamido]-pentanedioic acid | |
| 24 | (2S)-2-[(5-{[(2,4-diamino-6-oxo-1,6-dihydropyrimidin-5-yl)carbamoyl]amino}-3-fluoropyridin-2-yl)formamido]-4-(1H-1,2,3,4-tetrazol-5-yl)butanoic acid | |
| 25 | (2R)-2-[(4S)-4-carboxy-4-[(5-{[(2,4-diamino-6-oxo-1,6-dihydropyrimidin-5-yl)carbamoyl]amino}pyridin-2-yl)formamido]butanamido]-pentanedioic acid | |
| 26 | (2S)-2-({5-[2-(2,4-diamino-6-oxo-1,6-dihydropyrimidin-5-yl)acetamido]-6-phenoxypyridin-2-yl}formamido)pentanedioic acid | |

TABLE 1-continued

Chemical name and structural formula of Examples 1-35.

| Ex. | Chemical Name | Structural formula |
|---|---|---|
| 27 | (2S)-2-({5-[2-(2,4-diamino-6-oxo-1,6-dihydropyrimidin-5-yl)acetamido]-6-phenylpyridin-2-yl}formamido)pentanedioic acid | |
| 28 | (2S)-2-[(4S)-4-carboxy-4-({5-[2-(2,4-diamino-6-oxo-1,6-dihydropyrimidin-5-yl)acetamido]pyridin-2-yl}formamido)butanamido]-pentanedioic acid | |
| 29 | (2S)-2-({5-[2-(2,4-diamino-6-oxo-1,6-dihydropyrimidin-5-yl)acetamido]-6-methoxypyridin-2-yl}formamido)pentanedioic acid | |
| 30 | (2S)-2-({5-[2-(2,4-diamino-6-oxo-1,6-dihydropyrimidin-5-yl)acetamido]-3-(trifluoromethyl)pyridin-2-yl}formamido)pentanedioic acid | |
| 31 | (2S)-2-[(5-{[(2,4-diamino-6-oxo-1,6-dihydropyrimidin-5-yl)carbamoyl]amino}-3-fluoropyridin-2-yl)formamido]-3-methylbutanoic acid | |
| 32 | (2S)-2-({5-[2-(2,4-diamino-6-oxo-1,6-dihydropyrimidin-5-yl)acetamido]-3-fluoropyridin-2-yl}formamido)-4-(1H-1,2,3,4-tetrazol-5-yl)butanoic acid | |

TABLE 1-continued

Chemical name and structural formula of Examples 1-35.

| Ex. | Chemical Name | Structural formula |
|---|---|---|
| 33 | (2S)-2-({5-[2-(2,4-diamino-6-oxo-1,6-dihydropyrimidin-5-yl)acetamido]-3-fluoropyridin-2-yl}formamido)-3-phenylpropanoic acid | |
| 34 | (2S)-2-({5-[2-(2,4-diamino-6-oxo-1,6-dihydropyrimidin-5-yl)acetamido]-3-fluoropyridin-2-yl}formamido)-3-methylbutanoic acid | |
| 35 | (2S)-2-[(5-{[(2,4-diamino-6-oxo-1,6-dihydropyrimidin-5-yl)carbamoyl]amino}-3-fluoropyridin-2-yl)formamido]-3-phenylpropanoic acid | |

Biological Assays

Biological Example 1: Inhibition of MTHFD2

To determine the $IC_{50}$ value of a compound, an 11-concentration dose-response curve with 3-fold difference in concentration between assay points was generated by using an acoustic dispenser (Echo 550 Liquid handler, Labcyte). Each assay point was run in duplicate and the assay was performed in a white 384-well ProxiPlate Plus (6008280, PerkinElmer). DMSO was used as negative control. The serial dilution in DMSO, from compound DMSO stock solution, was created by dispensing from a 384-well low dead volume microplate (LP-0200, Labcyte) and a 384-well polypropylene microplate 2.0 (PP-0200, Labcyte). A total of 2.5 μL MTHFD2 was preincubated with compound or DMSO for 10 min. The enzymatic reaction was initiated by adding 2.5 μL folitixorin (F680350, Toronto Research Chemicals). For background control, 5 μL buffer was added to the well. Final concentrations of the components in the assay were 3.4 nmol/L MTHFD2, 5 μmol/L folitixorin and 250 μmol/L $NAD^+$. The final concentrations of all reagents in a total assay volume of 5 μL per well were 50 mmol/L Tris-HCl at pH 8.0, 100 mmol/L NaCl, 5 mmol/L $MgCl_2$, 25 mmol/L $Na_3PO_4$ at pH 8.0, 0.005% (v/v) Tween-20, and 2 mmol/L 2-mercaptoethanol. After 15 min reaction time, 5 μL NAD(P)H-Glo detection reagent (G9061 or G9062, Promega) was dispensed in all wells and the plate was incubated for 60 min. Luminescence was measured on a plate reader (Envision, PerkinElmer or Sense, Hidex). The light signal produced is proportional to the amount of NAD(P)H in the sample. $IC_{50}$ values were determined by fitting a four parameter sigmoidal curve model using XLfit (IDBS). Reported $IC_{50}$ values are the mean of at least 3 independent measurements.

TABLE 2

MTHFD2 inhibition data obtained for the example compounds listed below, expressed as $IC_{50}$ values.

| Example Number | $IC_{50}$ (nM) |
|---|---|
| 1 | 24 |
| 2 | 68 |
| 3 | 19 |
| 4 | 12 |
| 5 | 15 |
| 6 | 10 |
| 7 | 154 |
| 8 | 312 |
| 9 | 53 |
| 10 | 49 |
| 11 | 46 |
| 12 | 17 |
| 13 | 103 |
| 14 | 36 |
| 15 | 23 |
| 16 | 11 |
| 17 | 32 |
| 18 | 3 |
| 19 | 72 |
| 20 | 913 |
| 21 | 298 |
| 22 | 195 |
| 23 | 43 |
| 24 | 3 |
| 25 | 30 |
| 26 | 14 |
| 27 | 65 |
| 28 | 92 |

TABLE 2-continued

MTHFD2 inhibition data obtained for the example compounds listed below, expressed as $IC_{50}$ values.

| Example Number | $IC_{50}$ (nM) |
|---|---|
| 29 | 44 |
| 30 | 1,102 |
| 31 | 8 |
| 32 | 13 |
| 33 | 92 |
| 34 | 60 |
| 35 | 5 |

Biological Example 2: Cancer Cell Viability Assay

HL-60 cells (human promyelocytic leukemia cells) were seeded in a 384-well plate at a density of 2,000 cells per well in 50 µL induction medium and treated with vehicle (DMSO) or an 11-point concentration range with 3-fold dilution in concentration of compound. Each assay point was run in duplicate. Wells without cells but with DMSO were used as negative controls. The cells were left to proliferate over a period of 96 h, in an incubator at 37° C. and 5% $CO_2$, followed by an addition of 10 µL 60 pg/mL resazurin sodium salt (199303, Sigma-Aldrich) dissolved in DPBS (14190, Gibco). After 4 h of incubation at 37° C. and 5% $CO_2$, the fluorescent signal was measured using an excitation wavelength of 544 nm and an emission wavelength of 595 nm in a Hidex Sense plate reader. Cell plates were incubated in boxes with damp paper tissues to avoid evaporation. All additions, except compound and DMSO, were done using the Multidrop Combi (Thermo Fisher Scientific). DMSO and compounds were pre-dispensed with an Echo 550 Liquid handler (Labcyte) in black, clear bottom, TC-treated and sterile 384-well plates (3764, Corning). Growth medium consisted of RPMI 1640 GlutaMAX (61870, Gibco), 10% (v/v) FBS (10500, Gibco), and 1% (v/v) P/S (15070, Gibco). Induction medium consisted of RPMI 1640 GlutaMAX (61870, Gibco), 5% (v/v) FBS (10500, Gibco), and 1% (v/v) P/S (15070, Gibco). $EC_{50}$ values were determined by fitting a four parameter sigmoidal curve model using XLfit (IDBS). Reported $EC_{50}$ values are the mean of at least 3 independent measurements.

TABLE 3

HL60 Cell proliferation inhibition data obtained for the example compounds listed below, expressed as $EC_{50}$ values.

| Example Number | $EC_{50}$ (nM) |
|---|---|
| 1 | 75 |
| 2 | 10 |
| 3 | 31 |
| 4 | 24 |
| 5 | 93 |
| 6 | 100 |
| 7 | 17 |
| 8 | 62 |
| 9 | 35 |
| 10 | 14 |
| 11 | 37 |
| 12 | 7 |
| 13 | 215 |
| 14 | 187 |
| 15 | 470 |
| 16 | 197 |
| 17 | 200 |
| 18 | 45 |

TABLE 3-continued

HL60 Cell proliferation inhibition data obtained for the example compounds listed below, expressed as $EC_{50}$ values.

| Example Number | $EC_{50}$ (nM) |
|---|---|
| 19 | 8 |
| 20 | 34 |
| 21 | 8,618 |
| 22 | 12,835 |
| 23 | 835 |
| 24 | 2 |
| 25 | 1,937 |
| 26 | 6,191 |
| 27 | 2,769 |
| 28 | 22 |
| 29 | 1,121 |
| 30 | 161 |
| 31 | 20 |
| 32 | 10 |
| 33 | 24 |
| 34 | 177 |
| 35 | 20 |

Biological Example 3: T Cell Viability Assay

Figure 1B:
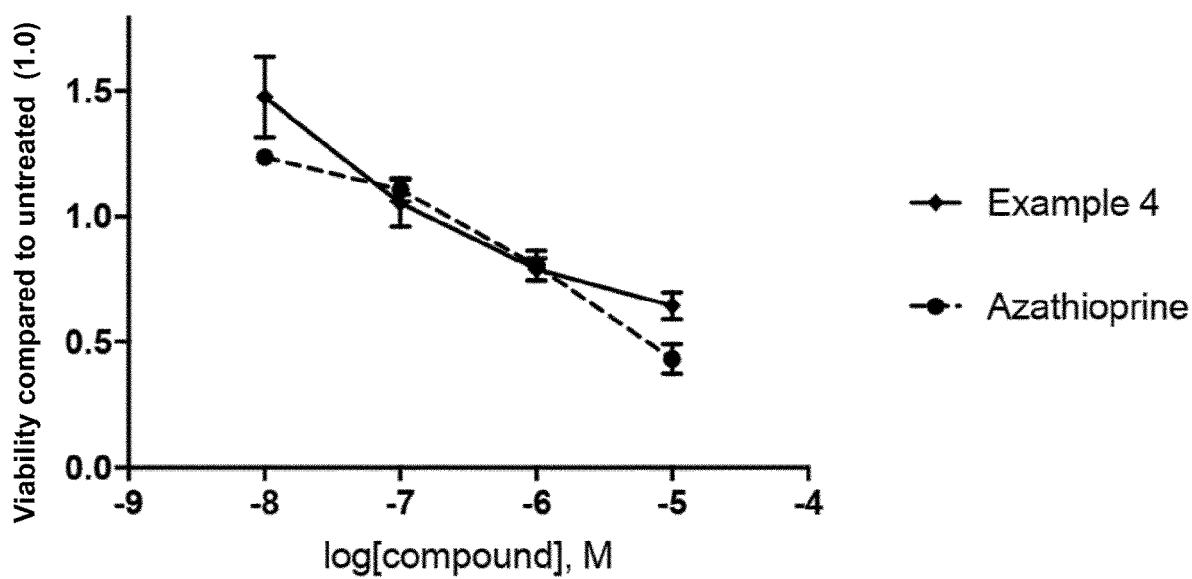

T lymphocytes from the peripheral blood of healthy donors were enriched using RosetteSep Human T Cell Enrichment Cocktail (StemCell Technologies) according to manufacturer's instructions. After enrichment, the blood was diluted 1:1 with PBS (Life Technologies) and layered on top of Ficoll-Paque Plus (GE Healthcare), then centrifuged 800 g, 30 min, no brakes. The purified T cells were collected at the interface between the plasma and the Ficoll-Paque, washed twice in PBS, then cultured in RPMI 1640 (Life Technologies) supplemented with 10% heat-inactivated human male AB plasma (Sigma-Aldrich), 100 units/mL penicillin and 100 pg/mL streptomycin (Gibco) at 37° C. and 5% $CO_2$. Per donor, half of the isolated T cells were activated in culture using Human T-Activator CD3/CD28 Dynabeads (Gibco) for 48 h. Test compounds were dissolved in DMSO, then dispensed in clear flat bottom TC-treated 96-well plates (Corning) using a D300e Digital Dispenser (Tecan) in triplicate wells for each concentration (10 µM, 1 µM, 100 nM, and 10 nM). After activation, both resting and activated cells were counted with 0.4% Trypan Blue solution (BioRad) using a TC20 Automated Cell Counter (BioRad), and seeded on the compound plates at a density per well of 60,000 cells for the activated cells, or 150,000 cells for the resting cells. T cell viability was determined after 3, 4 or 7 days incubation by adding 10 pg/mL resazurin (Sigma) and measuring conversion to resorufin at 595 nm after 4 h. Results obtained are shown in FIG. 1, as provided and described herein.

Biological Example 4: MTHFD2 Protein Expression Levels in T Cells

Figure 2:
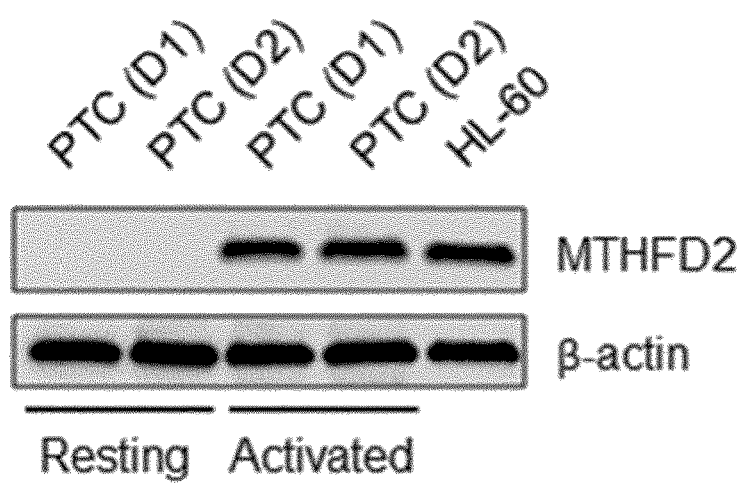
FIG. 2 is a Western blot image showing expression levels of MTHFD2 and actin in resting versus activated primary T cells (PTC) from 2 donors (D1 and D2) and HL-60 cancer cells.
Figure 3:
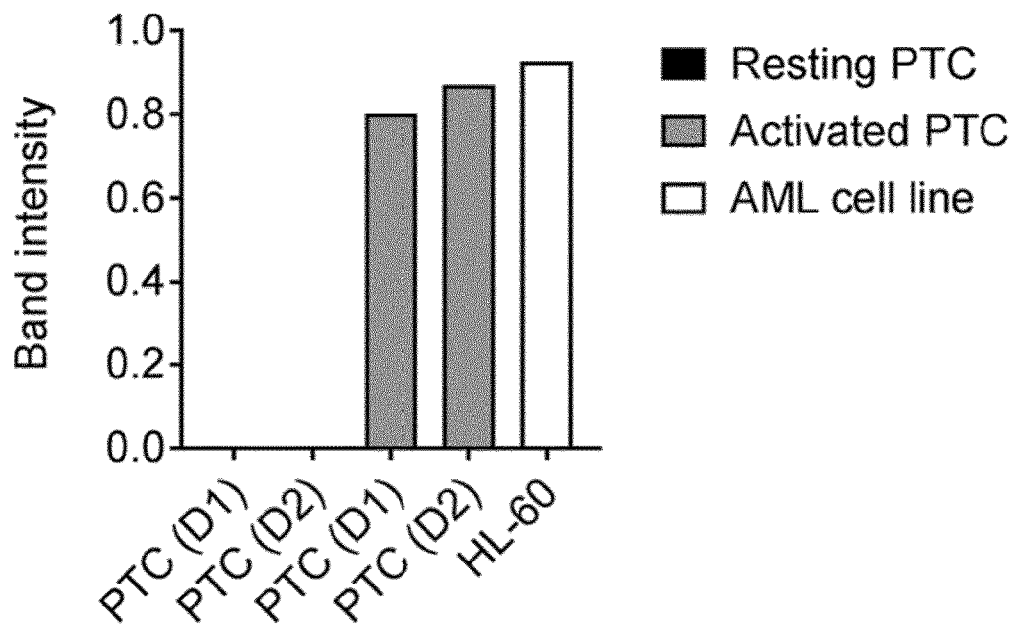
FIG. 3 is a bar chart representing the intensity of the MTHFD2 Western blot bands obtained for the resting and activated primary T cells from donors D1 and D2, respectively, and for the HL-60 cancer cells.

Whole cell lysates from resting and activated T cell were obtained by solubilizing the cells in ice-cold NP-40 lysis buffer: 100 mM Tris-HCl pH 8, 150 mM NaCl, 1% NP-40, complete Protease Inhibitors (Roche), Halt Phosphatase Inhibitors (Thermo Scientific). The samples were sonicated on ice for 3×10-second cycles at 100% amplitude and 50% pulse, and then centrifuged for 15 min at 4° C. The supernatant fraction was used for protein quantification using Pierce BCA Protein Assay Kit (Thermo Scientific). Per sample, 20 µg of protein were mixed with NuPage LDS sample buffer and NuPage sample reducing agent (Invitrogen), incubated at 70° C. for 10 min, loaded on a 4-15% Mini-PROTEAN TGX precast gel (BioRad), and separated in 1×TGS buffer for 75 min at 120 V. Proteins were blotted using the Trans-Blot Turbo Nitrocellulose Transfer Kit (Bio-Rad). The blot was blocked in Odyssey TBS blocking buffer (LI-COR Biosciences) at rt for 1 h, then incubated with primary antibodies against MTHFD2 (ab56772 Abeam, 1:500) and loading control 3-actin (ab6276 Abeam, 1:10,000) overnight at 4° C. After washing 3×10 min in 0.1% Tween20/TBS (TBS-T), the blots were incubated with IRDye 800CW donkey anti-mouse IgG secondary antibody solution 1:10,000 (LI-COR Biosciences) at rt for 1 h, washed 3×10 min in TBS-T, then imaged using an Odyssey Fc Imager (LI-COR Biosciences). Quantification of band intensities was performed using Image Studio software (LI-COR Biosciences). Results obtained are shown in FIGS. 2 and 3, as provided and described herein.

The invention claimed is:
1. A compound of formula I

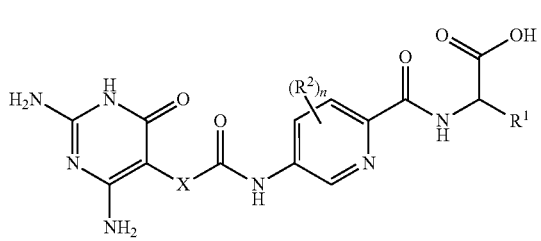

or a pharmaceutically-acceptable salt thereof, wherein:
$R^1$ represents
(i) $C_{1-6}$ alkyl, $C_{2-6}$ alkenyl or $C_{2-6}$ alkynyl each optionally substituted by one or more groups independently selected from oxy and $A^1$,
(ii) aryl optionally substituted by one or more groups independently selected from oxy and $A^2$,
(iii) heteroaryl optionally substituted by one or more groups independently selected from oxy and $A^3$,
(iv) heterocyclyl optionally substituted by one or more groups independently selected from oxy and $A^4$, or
(v) $-(CH_2)_2C(O)-G$;
each $R^2$ independently represents
(i) halo, $-NO_2$, $-CN$, $-R^{1a}$, $-OR^{1b}$, $-S(O)_pR^{1c}$, $-S(O)_qN(R^{1d})(R^{1e})$, $-N(R^{1f})S(O)_rR^{1g}$, $-N(R^{1h})(R^{1i})$, $-C(O)OR^{1j}$, or $C(O)N(R^{1k}k)(R^{1l})$,
(ii) aryl optionally substituted by one or more groups independently selected from oxy and $A^5$,
(iii) heteroaryl optionally substituted by one or more groups independently selected from oxy and $A^6$, or
(iv) heterocyclyl optionally substituted by one or more groups independently selected from oxy and $A^7$;
n represents 0 to 3;
X represents $-N(R^3)-$ or $-C(R^4)_2-$;
$R^3$ represents H or $C_{1-3}$ alkyl optionally substituted by one or more fluoro;
each $R^4$ independently represents H, fluoro or $C_{1-3}$ alkyl optionally substituted by one or more fluoro;
G represents $-OH$, or a mono- or poly-glutamic acid group;

each of $A^1$, $A^2$, $A^3$, $A^4$, $A^5$, $A^6$, and $A^7$ independently represents
(i) halo, $-NO_2$, $-CN$, $-R^{2a}$, $-OR^{2b}$, $-S(O)_pR^{2c}$, $-S(O)_qN(R^{2d})(R^{2e})$, $-N(R^{2f})S(O)_rR^{2g}$, $-N(R^{2h}h)(R^{2i})$, $-C(O)OR^{2j}$, or $-C(O)N(R^{2k})(R^{2l})$,
(ii) aryl optionally substituted by one or more groups independently selected from oxy and $B^1$,
(iii) heteroaryl optionally substituted by one or more groups independently selected from oxy and $B^2$, or
(iv) heterocyclyl optionally substituted by one or more groups independently selected from oxy and $B^3$;
each $R^{1a}$ and $R^{2a}$ independently represents
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $D^1$;
(ii) aryl optionally substituted by one or more groups independently selected from oxy and $D^2$,
(iii) heteroaryl optionally substituted by one or more groups independently selected from oxy and $D^3$, or
(iv) heterocyclyl optionally substituted by one or more groups independently selected from oxy and $D^4$;
each $R^{1b}$, $R^{1c}$, $R_{1d}$, $R^{1e}$, $R^{1f}$, $R^{1g}$, $R^{1h}$, $R^{1i}$, $R^{1j}$, $R^{1k}$, and $R^{1l}$ and $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ independently represents H or
(i) $C_{1-6}$ alkyl, $C_{2-6}$ alkenyl or $C_{2-6}$ alkynyl, wherein each such alkyl, alkenyl or alkynyl group is optionally substituted by one or more groups independently selected from oxy and $D^1$;
(ii) aryl optionally substituted by one or more groups independently selected from oxy and $D^2$,
(iii) heteroaryl optionally substituted by one or more groups independently selected from oxy and $D^3$, or
(iv) heterocyclyl optionally substituted by one or more groups independently selected from oxy and $D^4$;
each of $B^1$, $B^2$, and $B^3$ independently represents
(i) halo, $-NO_2$, $-CN$, $-R^{3a}$, $-OR^{3b}$, $-S(O)_pR^{3c}c$, $-S(O)_qN(R^{3d})(R^{3e})$, $-N(R^{3f})S(O)_rR^{3g}$, $-N(R^{3h})(R^{3i})$, $-C(O)OR^{3j}$, or $-C(O)N(R^{3k})(R^{3l})$,
(ii) aryl optionally substituted by one or more groups independently selected from oxy and $E^1$,
(iii) heteroaryl optionally substituted by one or more groups independently selected from oxy and $E^2$, or
(iv) heterocyclyl optionally substituted by one or more groups independently selected from oxy and $E^3$;
each $D^1$ independently represents
(i) halo, $-NO_2$, $-CN$, $-OR^{4b}$, $-S(O)_pR^{4c}$, $-S(O)_qN(R^{4d})(R^{4e})$, $-N(R^{4f})S(O)_rR^{4g}$, $-N(R^{4h})(R^{4i})$, $-C(O)OR^{4i}$, or $-C(O)N(R^{4k})(R^{4l})$,
(ii) aryl optionally substituted by one or more groups independently selected from oxy and $E^4$,
(iii) heteroaryl optionally substituted by one or more groups independently selected from oxy and $E^5$, or
(iv) heterocyclyl optionally substituted by one or more groups independently selected from oxy and E6;
each $D^2$, $D^3$, and $D^4$ independently represents
(i) halo, $-NO_2$, $-CN$, $-R^{4a}$, $-OR^{4b}$, $-S(O)_pR^{4c}$, $-S(O)_qN(R^{4d})(R^{4e})$, $-N(R^{4f})S(O)_rR^{4g}$, $-N(R^{4h})(R^{4i})$, $-C(O)OR^{4j}$, or $-C(O)N(R^{4k})(R^{4l})$,
(ii) aryl optionally substituted by one or more groups independently selected from oxy and $E^4$,
(iii) heteroaryl optionally substituted by one or more groups independently selected from oxy and $E^5$, or
(iv) heterocyclyl optionally substituted by one or more groups independently selected from oxy and $E^6$;

Each $R^{3a}$ and $R^{4a}$ independently represents $C_{1-3}$ alkyl optionally substituted with one or more fluoro;

each $R^{3b}b$, $R^{3c}$, $R^{3d}$, $R^{3e}$, $R^{3f}$, $R^{3g}R^{3h}$,$R^{3i}$, $R^{3j}$, $R^{3k}$, and $R^{3l}$, and $R^{4b}$, $R^{4c}$, $R^{4d}$, $R^{4e}$, $R^{4f}$, $R^{4g}$, $R^{4h}$, $R^{4i}$, $R^{4j}$, $R^{4k}$, and $R^{4l}$ independently represents H or $C_{1-3}$ alkyl optionally substituted with one or more fluoro;

each $E^1$, $E^2$, $E^3$, $E^4$, $E^5$, and $E^6$ independently represents halo, —$NO_2$, —CN, —$R^{5a}$, —$OR^{5b}$—$S(O)_pR^{5c}$, —$S(O)_qN(R^{5d})(R^{5e})$, —$N(R^{5f})S(O)_rR^{5g}$, —$N(R^{5h}h)(R^{5i})$, —$C(O)OR^{5j}$, or —$C(O)N(R^{5k}k)(R^{5l})$;

each $R^{5a}$ independently represents $C_{1-3}$ alkyl optionally substituted with one or more fluoro;

each $R^{5b}b$, $R^{5c}$, $R^{5d}$, $R^{5e}$, $R^{5f}$, $R^{5g}R^{5h}$, $R^{5i}$, $R^{5j}$, $R^{5k}$, and $R^{5l}$ independently represents H or $C_{1-3}$ alkyl optionally substituted with one or more fluoro; and each p, q and r independently represents 0, 1 or 2.

2. A compound as claimed in claim 1, wherein $R^1$ represents
(i) $C_{1-6}$ alkyl optionally substituted by one or more groups independently selected from oxy and $A^1$,
(ii) phenyl optionally substituted by one or more groups independently selected from $A^2$, or
(iii) —$(CH_2)_2C(O)$—G.

3. A compound as claimed in claim 1, wherein $R^1$ represents:
(i) $C_{1-6}$ alkyl optionally substituted by one or more groups independently selected from oxy and $A^1$, or
(ii) —$(CH_2)_2C(O)$—G.

4. A compound as claimed in claim 1, wherein G represents —OH or a mono-glutamic acid group.

5. A compound as claimed in claim 1, wherein each $A^1$ independently represents:
(i) —$R^{2a}$, —$N(R^{2f})S(O)_rR^{2g}$, —$C(O)OR^{2j}$ or —$C(O)N(R^{2k})(R^{2l})$,
(ii) phenyl optionally substituted by one or more groups independently selected from oxy and $B^1$, or
(iii) heteroaryl optionally substituted by one or more groups independently selected from oxy and $B^2$.

6. A compound as claimed in claim 1, wherein
$R^{2a}$ represents aryl optionally substituted by one or more groups independently selected from oxy and $D^2$;
$R^{2f}$ represents H;
$R^{2g}$ represents aryl optionally substituted by one or more groups independently selected from oxy and $D^2$;
$R^{2j}$ represents $C_{1-6}$ alkyl or H;
$R^{2k}$ represents H; and
$R^{2l}$ represents $C_{1-6}$ alkyl optionally substituted by one or more groups independently selected from oxy and $D^1$.

7. A compound as claimed in claim 1, wherein each $R^2$ independently represents, halo, —$R^{1a}$ or —$OR^{1b}$.

8. A compound as claimed in claim 1, wherein
each $R^{1a}$ independently represents $C_{1-6}$ alkyl or $C_{2-6}$ alkenyl each optionally substituted by one or more groups independently selected from oxy and fluoro; and
each $R^{1b}$ represents $C_{1-6}$ alkyl or phenyl.

9. A compound as claimed in claim 1, wherein n represents 0 or 1.

10. A compound as claimed in claim 1, wherein each $R^4$ represents H.

11. A compound as claimed in claim 1, wherein $R^3$ represents H.

12. A compound as claimed in claim 1, wherein X is —$C(R^4)2$—.

13. A compound as claimed in claim 1, wherein the compound of formula I is a compound of formula Ia

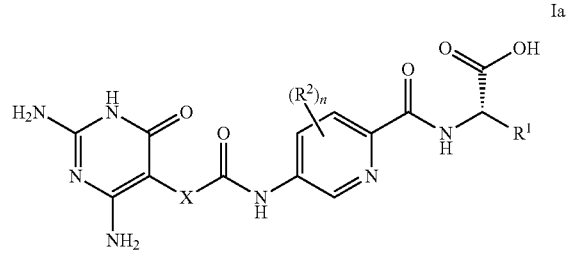

wherein $R^1$, $R^2$, X and n are as defined in claim 1.

14. A compound as claimed in claim 1, selected from
(2S)-2-[(5-{[(2,4-diamino-6-oxo-1,6-dihydropyrimidin-5-yl)carbamoyl]amino}pyridin-2-yl)formamido]pentanedioic acid, (2S)-2-[(5-{[(2,4-diamino-6-oxo-1,6-dihydropyrimidin-5-yl)carbamoyl]amino}pyridin-2-yl)formamido]-3-phenylpropanoic acid, (2S)-2-[(5-{[(2,4-diamino-6-oxo-1,6-dihydropyrimidin-5-yl)carbamoyl]amino}pyridin-2-yl)formamido]-3-methylbutanoic acid, (2S)-2-[(5-{[(2,4-diamino-6-oxo-1,6-dihydropyrimidin-5-yl)carbamoyl]amino}pyridin-2-yl)formamido]-4-(1 H-1,2,3,4-tetrazol-5-yl)butanoic acid, (2S)-2-[(3-chloro-5-{[(2,4-diamino-6-oxo-1,6-dihydropyrimidin-5 yl)carbamoyl]amino}pyridin-2-yl)formamido]pentanedioic acid, (2S)-2-[(5-{[(2,4-diamino-6-oxo-1,6-dihydropyrimidin-5-yl)carbamoyl]amino}-3-fluoropyridin-2-yl)formamido] pentanedioic acid, (2S)-2-({5-[2-(2,4-diamino-6-oxo-1,6-dihydropyrimidin-5-yl)acetamido]pyridin-2-yl}formamido)pentanedioic acid, (2S)-2-({5-[2-(2,4-diamino-6-oxo-1,6-dihydropyrimidin-5-yl)acetamido]pyridin-2-yl}formamido)-3-phenylpropanoic acid, (2S)-2-({5-[2-(2,4-diamino-6-oxo-1,6-dihydropyrimidin-5-yl)acetamido]pyridin-2-yl}formamido)-4-(1 H-1,2,3,4-tetrazol-5-yl)butanoic acid, (2S)-2-({5-[2-(2,4-diamino-6-oxo-1,6-dihydropyrimidin-5-yl)acetamido]-3-fluoropyridin-2-yl}formamido)pentanedioic acid, (2S)-3-cyclopentyl-2-[(5-{[(2,4-diamino-6-oxo-1,6-dihydropyrimidin-5-yl)carbamoyl]amino}pyridin-2-yl)formamido]propanoic acid, (2S)-2-cyclohexyl-2-[(5-{[(2,4-diamino-6-oxo-1,6-dihydropyrimidin-5-yl)carbamoyl]amino}pyridin-2-yl)formamido]acetic acid, (2S)-2-({5-[2-(2,4-diamino-6-oxo-1,6-dihydropyrimidin-5-yl)acetamido]pyridin-2-yl}formamido)-3-methylbutanoic acid, (2S)-2-[(5-{[(2,4-diamino-6-oxo-1,6-dihydropyrimidin-5-yl)carbamoyl]amino}pyridin-2-yl)formamido]-4-phenylbutanoic acid, (2S)-2-[(5-{[(2,4-diamino-6-oxo-1,6-dihydropyrimidin-5-yl)carbamoyl]amino}pyridin-2-yl)formamido]-2-phenylacetic acid, (2S)-4-[(benzenesulfonyl)carbamoyl]-2-[(5-{[(2,4-diamino-6-oxo-1,6-dihydropyrimidin-5-yl)carbamoyl] amino}pyridin-2-yl)formamido]butanoic acid, (2S)-2-[(5-{[(2,4-diamino-6-oxo-1,6-dihydropyrimidin-5-yl)carbamoyl]amino}pyridin-2-yl)formamidoThexanedioic acid, (2S)-2-[(6-cyclopropoxy-5-{[(2,4-diamino-6-oxo-1,6-dihydropyrimidin-5-yl)carbamoyl]amino}pyridin-2-yl)formamido]pentanedioic acid, (2S)-2-({3-chloro-5-[2-(2,4-diamino-6-oxo-1,6-dihydropyrimidin-5-yl)acetamido]pyridin-2-yl}formamido)pentanedioic acid, (2S)-2-({5-[2-(2,4-diamino-6-oxo-1,6-dihydropyrimidin-5-yl)acetamido]-3-methylpyridin-2-yl}formamido)pentanedioic acid, (2S)-2-({5-[2-(2,4-diamino-6-oxo-1,6-dihydropyrimidin-5-yl)acetamido]-6-ethenylpyridin-2-yl}formamido)pentanedioic acid, (2S)-2-[(5-{[(2,4-diamino-6-oxo-1,6-dihydropyrimidin-5-yl)carbamoyl]amino}pyridin-2-yl)formamido]butanedioic acid, (2S)-2-[(4S)-4-carboxy-4-[(5-{[(2,4-diamino-6-oxo-1,6-dihydropyrimidin-5-yl)carbamoyl]amino}pyridin-2-yl)formamido]butanamido]pentanedioic acid, (2S)-2-[(5-{[(2,4-diamino-6-oxo-1,6-dihydropyrimidin-5-yl)carbamoyl]amino}-3-fluoropyridin-2-yl)formamido]-4-(1H-1,2,3,4-tetrazol-5-yl)butanoic acid, (2R)-2-[(4S)-4-carboxy-4-[(5-{[(2,4-diamino-6-oxo-1,6-dihydropyrimidin-5-yl)carbamoyl]amino}pyridin-2-yl)formamido]butanamido]pentanedioic acid, (2S)-2-({5-[2-(2,4-diamino-6-oxo-1,6-dihydropyrimidin-5-yl)acetamido]-6-phenoxypyridin-2-yl}formamido)pentanedioic acid, (2S)-2-({5-[2-(2,4-diamino-6-oxo-1,6-dihydropyrimidin-5-yl)acetamido]-6-phenylpyridin-2-yl}formamido)pentanedioic acid, (2S)-2-[(4S)-4-carboxy-4-({5-[2-(2,4-diamino-6-oxo-1,6-dihydropyrimidin-5-yl)acetamido]pyridin-2-yl}formamido)butanamido]pentanedioic acid, (2S)-2-({5-[2-(2,4-diamino-6-oxo-1,6-dihydropyrimidin-5-yl)acetamido]-6-methoxypyridin-2-yl}formamido)pentanedioic acid, (2S)-2-({5-[2-(2,4-diamino-6-oxo-1,6-dihydropyrimidin-5-yl)acetamido]-3-(trifluoromethyl)pyridin-2-yl}formamido)pentanedioic acid, (2S)-2-[(5-{[(2,4-diamino-6-oxo-1,6-dihydropyrimidin-5-yl)carbamoyl]amino}-3-fluoropyridin-2-yl)formamido]-3-methylbutanoic acid, (2S)-2-({5-[2-(2,4-diamino-6-oxo-1,6-dihydropyrimidin-5-yl)acetamido]-3-fluoropyridin-2-yl}formamido)-4-(1 H-1,2,3,4-tetrazol-5-yl)butanoic acid, (2S)-2-({5-[2-(2,4-diamino-6-oxo-1,6-dihydropyrimidin-5-yl)acetamido]-3-fluoropyridin-2-yl}formamido)-3-phenylpropanoic acid, (2S)-2-({5-[2-(2,4-diamino-6-oxo-1,6-dihydropyrimidin-5-yl)acetamido]-3-fluoropyridin-2-yl}formamido)-3-methylbutanoic acid, and (2S)-2-[(5-{[(2,4-diamino-6-oxo-1,6-dihydropyrimidin-5-yl)carbamoyl]amino}-3-fluoropyridin-2-yl)formamido]-3-phenylpropanoic acid, or a pharmaceutically acceptable salt thereof.

15. A pharmaceutical composition comprising a compound as claimed in claim 1, and optionally one or more pharmaceutically-acceptable excipient.

\* \* \* \* \*